US007879880B2

(12) United States Patent  
Solomon et al.

(10) Patent No.: US 7,879,880 B2  
(45) Date of Patent: Feb. 1, 2011

(54) SUBSTITUTED ANILINE DERIVATIVES USEFUL AS HISTAMINE H3 ANTAGONISTS

(75) Inventors: Daniel M. Solomon, Edison, NJ (US); Robert G. Aslanian, Rockaway, NJ (US); Michael Y. Berlin, Flemington, NJ (US); Manuel de Lera Ruiz, Branchburg, NJ (US); Kevin D. McCormick, Basking Ridge, NJ (US); Mwangi W. Mutahi, Nyeri (KE); Wing C. Tom, Cedar Grove, NJ (US)

(73) Assignee: Schering Corporation, Kenilworth, NJ (US)

( * ) Notice: Subject to any disclaimer, the term of this patent is extended or adjusted under 35 U.S.C. 154(b) by 890 days.

(21) Appl. No.: 11/641,153

(22) Filed: Dec. 19, 2006

(65) Prior Publication Data

US 2007/0142394 A1 Jun. 21, 2007

Related U.S. Application Data

(60) Provisional application No. 60/752,637, filed on Dec. 21, 2005.

(51) Int. Cl.  
*A61K 31/5377* (2006.01)  
*A61K 31/496* (2006.01)  
*A61K 31/4545* (2006.01)  
*C07D 487/04* (2006.01)  
*C07D 413/14* (2006.01)  
*C07D 401/14* (2006.01)  
*C07D 401/12* (2006.01)

(52) U.S. Cl. .............. 514/318; 514/234.5; 514/253.01; 514/303; 514/316; 544/354; 544/360; 544/130; 546/118; 546/187; 546/193

(58) Field of Classification Search ................ 514/318, 514/234.5, 253.01, 303, 316; 544/354, 360, 544/130; 546/118, 187, 193  
See application file for complete search history.

(56) References Cited

U.S. PATENT DOCUMENTS

| | | | | |
|---|---|---|---|---|
| 4,166,853 | A * | 9/1979 | McCall | ........................ 514/313 |
| 5,869,479 | A | 2/1999 | Kreutner et al. | |
| 6,720,328 | B2 | 4/2004 | Aslanian et al. | |
| 6,849,621 | B2 | 2/2005 | Rosenblum et al. | |
| 7,122,544 | B2 * | 10/2006 | Kois et al. | ................ 514/235.8 |
| 7,220,735 | B2 * | 5/2007 | Ting et al. | ............... 514/210.21 |
| 2003/0045519 | A1 | 3/2003 | Aslanian et al. | |
| 2003/0109564 | A1 | 6/2003 | Rosenblum et al. | |
| 2003/0203926 | A1 * | 10/2003 | Kois et al. | .................. 514/275 |
| 2004/0019099 | A1 | 1/2004 | Aslanian et al. | |
| 2004/0048843 | A1 | 3/2004 | Ting et al. | |
| 2004/0097483 | A1 | 5/2004 | Zeng et al. | |
| 2004/0224953 | A1 | 11/2004 | Cowart et al. | |

FOREIGN PATENT DOCUMENTS

WO WO 02/32893 A2 4/2002

| | | | |
|---|---|---|---|
| WO | WO 03/103669 A1 | 12/2003 | |
| WO | WO 2004/000831 A1 | 12/2003 | |
| WO | WO 2004/089373 A1 | 10/2004 | |
| WO | WO 2004/101546 A1 | 11/2004 | |

OTHER PUBLICATIONS

Giron, D. J. Therm. Anal. Cal. 2001, 64, pp. 37-60.*  
Giron, D. J. Therm. Anal. Cal. 2002, 68, pp. 335-357.*

(Continued)

*Primary Examiner*—Rebecca L Anderson  
*Assistant Examiner*—Matthew P Coughlin  
(74) *Attorney, Agent, or Firm*—J. Eric Thies; Gerard M. Devlin

(57) ABSTRACT

Disclosed are compounds of the formula

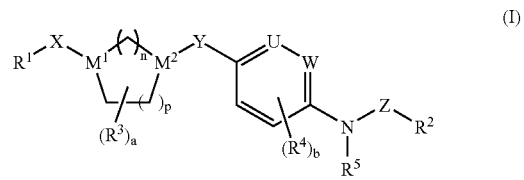

(I)

or a pharmaceutically acceptable salt thereof, wherein $M^1$ is

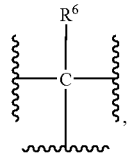

$M^2$ is N; X is a bond, optionally substituted alkylene, alkenylene, —O—, —$CH_2N(R^{12})$—, —$N(R^{12})CH_2$—, —$N(R^{12})$—, —NHC(O)—, —$OCH_2$—, —$CH_2O$—, or —$S(O)_{0-2}$—; and Y is —$(CH_2)_{1-2}$—, —C(=O)—, —C(=$NOR^{13}$)— or —$SO_{0-2}$—;

or $M^1$ is N; $M^2$ is N or CH; X is a bond, alkylene, alkenylene, —C(O)—, —NHC(O)—, —OC(O)— or —$S(O)_{1-2}$—; Y is —$(CH_2)_{1-2}$—, —C(=O)— or —$SO_{0-2}$—; and when $M^2$ is CH, Y is also Y is —O— or —C(=$NOR^{13}$)—;

Z is a bond or optionally substituted alkylene or alkenylene;

U and W are CH, or one is CH and one is N;

$R^1$ is optionally substituted alkyl, cycloalkyl, aryl, arylalkyl, heteroaryl, heterocycloalkyl;

$R^2$ is optionally substituted alkyl, alkenyl, aryl, arylalkyl, heteroaryl, heteroarylalkyl, cycloalkyl or heterocycloalkyl;

and the remaining variables are as defined in the specification; and compositions and methods of treating obesity, metabolic syndrome and a cognition deficit disorder, alone or in combination with other agents.

2 Claims, No Drawings

OTHER PUBLICATIONS

B. Rodriquez-Spong et al. Advanced Drug Delivery Reviews, 2004, 56, pp. 241-274.*

Souillac, et al., Characterization of Delivery Systems, Differential Scanning Calorimetry, pp. 217-218 (in Encyclopedia of Controlled Drug Delivery, 1999, John Wiley & Sons, pp. 212-227).*

Hancock et al., "Cognitive enhancing effects of drugs that target histamine receptors", *Cognitive Enhancing Drugs*, Edited by J. J. Buccafusco, Birkhauser, Basel pp. 97-114 (2004).

Leurs et al., "The Histamine $H_3$Receptor: From Gene Cloning to $H_3$ Receptor Drugs", *Nature Reviews Drug Discovery*, 4(2):107-120 (Feb. 2005).

Tashiro et al., "Roles of histamine in regulation of arousal and cognition: functional neuroimaging of histamine H1 receptors in human brain",*Life Sciences*, 72:409-414 (2002).

International Search Report for corresponding PCT Application No. PCT/US2006/048440 dated Jul. 13, 2007.

* cited by examiner

SUBSTITUTED ANILINE DERIVATIVES USEFUL AS HISTAMINE H3 ANTAGONISTS

This application claims the benefit of U.S. Provisional Application No. 60/752,637, filed Dec. 21, 2005, which is incorporated by reference herein in its entirety.

FIELD OF THE INVENTION

The present invention relates to substituted aniline derivatives useful as histamine $H_3$ antagonists. The invention also relates to pharmaceutical compositions comprising said compounds and their use in treating inflammatory diseases, allergic conditions, diabetes, obesity, an obesity-related disorder, metabolic syndrome, a cognition deficit disorder, cardiovascular and central nervous system disorders. The invention also relates to the use of a combination of histamine $H_3$ antagonists of this invention with histamine $H_1$ compounds for the treatment of inflammatory diseases and allergic conditions, as well to the use of a combination of an histamine $H_3$ antagonist of this invention with other actives useful for treating diabetes, obesity, an obesity-related disorder, metabolic syndrome or a cognition deficit disorder. Pharmaceutical compositions comprising a combination of at least one novel histamine $H_3$ antagonist compound of the invention with at least one histamine $H_1$ compound or at least one compound useful for treating diabetes, obesity, an obesity-related disorder, metabolic syndrome or a cognition deficit disorder are also contemplated.

BACKGROUND OF THE INVENTION

The histamine receptors, $H_1$, $H_2$, $H_3$ and $H_4$ have been characterized by their pharmacological behavior. The $H_1$ receptors are those that mediate the response antagonized by conventional antihistamines. $H_1$ receptors are present, for example, in the ileum, the skin, and the bronchial smooth muscle of humans and other mammals. The most prominent $H_2$ receptor-mediated responses are the secretion of gastric acid in mammals and the chronotropic effect in isolated mammalian atria. $H_4$ receptors are expressed primarily on eosinophils and mast cells and have been shown to be involved in the chemotaxis of both cell types.

In the periphery, $H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates norepinephrine outflow to resistance and capacitance vessels, causing vasodilation. In addition, in rodents, peripheral $H_3$ receptors are expressed in brown adipose tissue, suggesting that they may be involved in thermogenesis regulation.

$H_3$ receptors are also present in the CNS. $H_3$ receptor expression is observed in cerebral cortex, hippocampal formation, hypothalamus and other parts of the human and animal brain. $H_3$ receptors are expressed on histaminergic neurons and, as heteroreceptors, on neurons involved in other neurotransmitter systems, where $H_3$ receptor activation results in presynaptic inhibition of neurotransmitter release. In the particular case of histaminergic neurons, $H_3$ receptors have been implicated in the regulation of histamine hypothalamic tone, which in turn has been associated with the modulation of sleeping, feeding and cognitive processes in the human brain (see, for example, Leurs et al., Nature Reviews, Drug Discovery, 4, (2005), 107).

It is also known and has been described in the literature that histamine is involved in regulation of cognitive and memory processes in the human brain (see, for example, Life Sciences, 72, (2002), 409-414). Consequently, indirect modulation of histaminergic brain function through the central $H_3$ receptors may be a means to modulate these processes. Different classes of $H_3$ receptor ligands have been described and their use for neurological and psychiatric diseases has been suggested (see, e.g., US 20040224953, WO2004089373, WO2004101546). $H_3$ receptor antagonists may be useful in treating various neuropsychiatric conditions, where cognitive deficits are an integral part of the disease, specifically ADHD, schizophrenia and Alzheimer's disease (see, for example, Hancock, A.; Fox, G. in Drug Therapy (ed. Buccafusco, J. J.). (Birkhauser, Basel, 2003).

Imidazole $H_3$ receptor antagonists are well known in the art. More recently, non-imidazole $H_3$ receptor antagonists have been disclosed in U.S. Pat. Nos. 6,720,328 and 6,849,621, and in US Published Applications 2004/0097483, 2004/0048843 and 2004/0019099.

U.S. Pat. No. 5,869,479 discloses compositions for the treatment of the symptoms of allergic rhinitis using a combination of at least one histamine $H_1$ receptor antagonist and at least one histamine $H_3$ receptor antagonist.

SUMMARY OF THE INVENTION

The present invention provides compounds of formula (I):

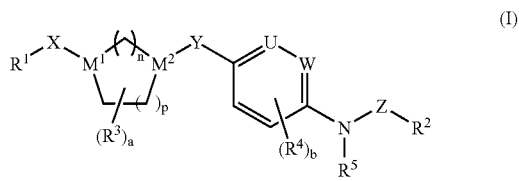

or a pharmaceutically acceptable salt thereof, wherein:

a is 0, 1 or 2;

b is 0, 1, 2, 3 or 4;

U and W are each CH, or one of U and W is CH and the other is N;

$M^1$, $M^2$, n, p, X and Y are as defined in (a), (b) or (c):

(a) $M^1$ is

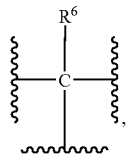

$M^2$ is N n is 1 or 2; p is 0, 1 or 2;

X is a bond, alkylene, alkenylene, —C(O)—, —C($R^8$)($R^9$)—, —C(=N—$OR^{10}$)—, —C(=N—$OR^{10}$)—CH($R^{11}$)—, —CH($R^{11}$)—C(N—$OR^{10}$)—, —O—, —$CH_2$N($R^{12}$)—, —N($R^{12}$)$CH_2$—, —N($R^{12}$)—, —NHC(O)—, —$OCH_2$—, —$CH_2$O—, —CH(OH)—, —S—, —S(O)— or —S(O)$_2$—; and Y is —$CH_2$—, —($CH_2$)$_2$—, —C(=O)—, —C(=N$OR^{13}$)—, —S—, —S(O)— or —$SO_2$—;

(b) $M^1$ is N $M^2$ is N;

n is 2; p is 1 or 2;

X is a bond, alkylene, alkenylene, —C(O)—, —NHC(O)—, —OC(O)—, —S(O)— or —S(O)$_2$—; and Y is —$CH_2$—, —($CH_2$)$_2$—, —C(=O)—, —S—, —S(O)— or —$SO_2$—;

(c) $M^1$ is N
$M^2$ is CH;
n is 1 or 2; p is 0, 1 or 2;
X is a bond, alkylene, alkenylene, —C(O)—, —NHC(O)—, —OC(O)—, —S(O)— or —S(O)$_2$—; and
Y is —O—, —CH$_2$—, —(CH$_2$)$_2$—, —C(=O)—, —C(=NOR$^{13}$)—, —S—, —S(O)— or —SO$_2$—;
Z is a bond, —CH(R$^{14}$)—(R$^{14a}$—(C$_1$-C$_4$)alkylene)- or —CH(R$^{14}$)—CH(R$^{14b}$)=CH(R$^{14b}$)—(R$^{14a}$—(C$_1$-C$_2$)alkylene)-;
$R^1$ is R$^{15}$-alkyl, R$^{15}$-cycloalkyl, R$^{15}$-aryl, R$^{15}$-arylalkyl, R$^{15}$-(6-membered heteroaryl), R$^{15}$-(6-membered heteroaryl)alkyl, R$^{15}$-(5-membered heteroaryl), R$^{15}$-(5-membered heteroaryl)alkyl, R$^{15}$-heterocycloalkyl, diphenylmethyl,

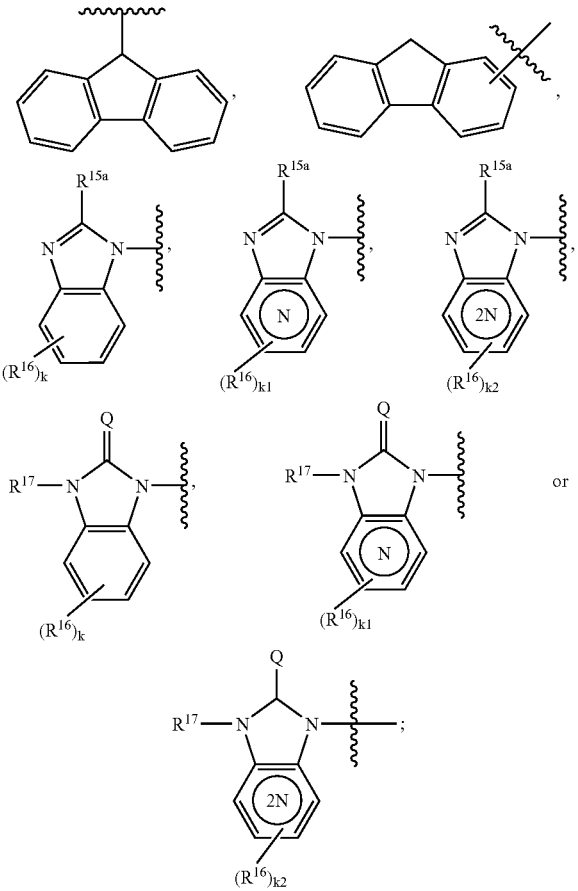

provided that when $R^1$ is attached to X by a nitrogen atom and $M^1$ is

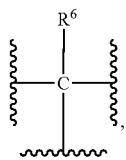

X is a bond or alkylene; and provided that when $R^1$ is attached to X by a nitrogen atom and $M^1$ is N, X is —(CH$_2$)$_{2-6}$—;
k is 0, 1, 2, 3 or 4;
k1 is 0, 1, 2 or 3;
k2 is 0, 1 or 2;
Q is O or S;

$R^2$ is R$^{18}$-alkyl, R$^{18}$-alkenyl, R$^{18}$-aryl, R$^{18}$-arylalkyl, R$^{18}$-heteroaryl, R$^{18}$-heteroarylalkyl, R$^{18}$-cycloalkyl or R$^{18}$-heterocycloalkyl;
each $R^3$ is independently selected from the group consisting of H, halo, alkyl, haloalkyl, —OH, alkoxy and —CN;
each $R^4$ is independently selected from the group consisting of H, alkyl, —OH, alkoxy, halo, —CF$_3$, —OCF$_3$, —NO$_2$, —CO$_2$R$^{19}$, —N(R$^{19}$)$_2$, —CON(R$^{19}$)$_2$, —NHC(O)R$^{19}$, —NHSO$_2$R$^{19}$, —SO$_2$N(R$^{19}$)$_2$ and —CN;
$R^5$ is H, alkyl, haloalkyl, R$^{21}$-cycloalkyl, R$^{21}$-aryl, R$^{21}$-heteroaryl or —C(O)R$^{20}$;
$R^6$ is H or alkyl; and when $R^1$ is attached to X by a carbon atom and X is a bond or alkylene, $R^6$ can also be R$^{21}$-cycloalkyl, R$^{21}$-aryl, R$^{21}$-heteroaryl, —NHC(O)R$^7$, —CN, hydroxyalkyl, alkoxyalkyl, —C(R$^7$)=N(OR$^7$), —C(O)R$^7$ or —N(R$^7$)$_2$;
$R^7$ is independently selected from the group consisting of H and alkyl;
$R^8$ and $R^9$, together with the carbon to which they are attached, form a 3- to 7-membered carbocyclic ring optionally substituted with 1 or 2 substituents independently selected from the group consisting of halo, alkyl and haloalkyl; or $R^8$ and $R^9$, together with the carbon to which they are attached, form a 3- to 7-membered heterocyclic ring comprising 2 to 6 carbon atoms and 1 or 2 heteroatoms independently selected from the group consisting of O, S and N, provided that there is no —)—O—, —S—S— or —O—S— bond, wherein said heterocyclic ring is optionally substituted with 1 or 2 substituents independently selected from the group consisting of halo, alkyl and haloalkyl; or $R^8$ and $R^9$ together are =CH$_2$;
$R^{10}$ is H, alkyl, haloalkyl, R$^{21}$-aryl, R$^{21}$-heteroaryl, R$^{21}$-cycloalkyl, R$^{21}$-heterocycloalkyl or R$^{21}$-arylalkyl;
$R^{11}$ is H or alkyl;
$R^{12}$ is independently selected from the group consisting of H, alkyl, —CH$_2$CF$_3$, R$^{21}$-aryl and R$^{21}$-heteroaryl;
$R^{13}$ is H, alkyl, haloalkyl, R$^{21}$-aryl or R$^{21}$-heteroaryl;
$R^{14}$ is H, alkyl or haloalkyl;
$R^{14a}$ is 1 to 3 substituents independently selected from the group consisting of H, halo, —OH, alkyl, haloalkyl, R$^{21}$-cycloalkyl, R$^{21}$-heterocycloalkyl, R$^{21}$-aryl, R$^{21}$-heteroaryl, alkoxy, —OCF$_3$, —OCHF$_2$, —NO$_2$, —CN and —N(R$^{11}$)$_2$;
$R^{14b}$ is H, fluoro, alkyl or haloalkyl;
$R^{15}$ is 1, 2, 3 or 4 substituents independently selected from the group consisting of H, halo, alkyl, haloalkyl, —OH, alkoxy, alkylthio, R$^{21}$-cycloalkyl, R$^{21}$-heterocycloalkyl, R$^{21}$-aryl, R$^{21}$-arylalkyl, R$^{21}$-heteroaryl, R$^{21}$-heteroarylalkyl, aryloxy, —OCF$_3$, —OCHF$_2$, —SCF$_3$, —NO$_2$, —CO$_2$R$^{12}$, —C(O)R$^{20}$, —N(R$^{12}$)$_2$, —CON(R$^{12}$)$_2$, —NHC(O)R$^{12}$, —NHSO$_2$R$^{12}$, —SO$_2$N(R$^{12}$)$_2$ and —CN; or two R$^{15}$ substituents on adjacent ring carbon atoms together are —O—CH$_2$—O—;
$R^{15a}$ is H, alkyl, haloalkyl, alkoxy, alkylthio, R$^{21}$-cycloalkyl, R$^{21}$-heterocycloalkyl, R$^{21}$-aryl, R$^{21}$-arylalkyl, R$^{21}$-heteroaryl, R$^{21}$-heteroarylalkyl, R$^{21}$-aryloxy, —OCF$_3$, —OCHF$_2$, —N(R$^{12}$)$_2$ or —SCF$_3$;
$R^{16}$ is independently selected from the group consisting of alkyl, halogen, haloalkyl and alkenyl;
$R^{17}$ is H, alkyl, hydroxy(C$_2$-C$_6$)alkyl-, haloalkyl-, haloalkoxyalkyl-, alkoxyalkyl-, R$^{21}$-aryl, R$^{21}$-arylalkyl-, R$^{21}$-heteroaryl, R$^{21}$-heteroarylalkyl-, R$^{21}$-cycloalkyl or R$^{21}$-cycloalkylalkyl, or R$^{21}$-heterocycloalkylalkyl;
$R^{18}$ is 1, 2 or 3 substituents independently selected from the group consisting of H, halo, alkyl, haloalkyl, —OH, alkoxy, R$^{21}$-aryl, R$^{21}$-aryloxy, —OCF$_3$, —OCHF$_2$, —NO$_2$, —CO$_2$R$^{19}$, —N(R$^{19}$)$_2$, —CON(R$^{19}$)$_2$, —NHC(O)R$^{19}$, —NHSO$_2$R$^{19}$, —SO$_2$N(R$^{19}$)$_2$ and —CN;

$R^{19}$ is independently selected from the group consisting of H, alkyl, haloalkyl, $R^{21}$-aryl, $R^{21}$-heteroaryl, $R^{21}$-cycloalkyl and $R^{21}$-heterocycloalkyl;

$R^{20}$ is alkyl, $R^{21}$-aryl or $R^{21}$-heteroaryl; and $R^{21}$ is 1, 2 or 3 substituents independently selected from the group consisting of H, alkyl, halo, alkoxy, —$CF_3$, —$N(R^{11})_2$ and -alkylene-$N(R^{11})_2$.

This invention further provides methods for treating: allergy; an allergy-induced airway (e.g., upper airway) response, including but not limited to, pruritis, sneezing, rhinorrhea and mucosal inflammation (see, for example, McLeod, *JPET*, 305 (2003) 1037); congestion, such as nasal congestion; hypotension; a cardiovascular disease; a disease of the gastrointestinal tract; hyper- and hypo-motility and acidic secretion of the gastrointestinal tract, such as GERD; metabolic syndrome; obesity; an obesity-related disorder; a sleeping disorder such as hypersomnia, somnolence, insomnia or narcolepsy; hypo- and hyperactivity of the central nervous system, such as agitation and depression of the CNS; diabetes, including Type I and Type II diabetes mellitus; a CNS disorder, such as migraine, Parkinson's disease, amyotrophic lateral sclerosis (ALS), or a cognition deficit disorder (e.g., attention deficit hyperactivity disorder (ADHD), Alzheimer's Disease (AD) or schizophrenia); (each of the above described diseases/disorders being a "Condition") comprising administering to a patient in need of such treatment an effective amount of at least one compound of formula (I).

The invention also provides pharmaceutical compositions comprising an effective amount of at least one compound of formula (I) and a pharmaceutically acceptable carrier. In one aspect, the compositions further comprise one or more additional agents useful for treating obesity, diabetes, an obesity-related disorder, metabolic syndrome or a cognition deficit disorder. In one aspect, the compositions further comprise one or more $H_1$ receptor antagonists. The compositions are useful for treating a Condition.

The invention further provides methods for treating obesity, an obesity-related disorder, metabolic syndrome or a cognition deficit disorder comprising administering to a patient in need of such treatment an effective amount of a combination of at least one compound of formula (I) and at least one other compound useful for treating obesity, an obesity-related disorder, metabolic syndrome or a cognition deficit disorder.

The invention also provides methods for treating obesity or an obesity-related disorder in a patient, comprising administering to the patient an effective amount of at least one compound of formula (I) and an anti-diabetic agent.

The present invention also provides methods for treating allergy, an allergy-induced airway response or congestion comprising administering to a patient in need of such treatment an effective amount of at least one compound of claim 1 and an effective amount of an $H_1$ receptor antagonist.

The present invention further provides methods for treating diabetes in a patient, comprising administering to the patient an effective amount of at least one compound of claim 1.

The invention also provides kits comprising a single package which contains: (i) a container containing a pharmaceutical composition comprising an effective amount of a compound of formula (I), and (ii) another container containing a pharmaceutical composition comprising an $H_1$ receptor antagonist. Also provided are kits comprising a single package which contains: (i) a container containing a pharmaceutical composition comprising an effective amount of a compound of formula (I), and (ii) another container containing a pharmaceutical composition comprising an effective amount of a separate compound useful for treating obesity, an obesity-related disorder, metabolic syndrome or a cognition deficit disorder.

DETAILED DESCRIPTION OF THE INVENTION

The present invention provides compounds of formula (I), pharmaceutical compositions comprising at least one compound of formula (I), and methods of using at least one compound of formula (I) to treat or prevent a Condition.

Definitions and Abbreviations

As used herein, the following terms have the following meanings, unless indicated otherwise:

A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

"Alkyl" (including, for example, the alkyl portions of arylalkyl and alkoxy) refers to straight and branched carbon chains and contains from one to six carbon atoms.

"Alkylene" refers to a divalent straight or branched alkyl chain, e.g., methylene (—$CH_2$—) or propylene (—$CH_2CH_2CH_2$—).

"Haloalkyl" or "haloalkoxy" refer to alkyl or alkoxy chains as defined above wherein one or more hydrogen atoms are replaced by halogen atoms, e.g., —$CF_3$, $CF_3CH_2CH_2$—, $CF_3CF_2$— or $CF_3O$—.

"Aryl" (including the aryl portion of arylalkyl) refers a carbocyclic group containing from 6 to 15 carbon atoms and having at least one aromatic ring (e.g., aryl is a phenyl or naphthyl ring), with all available substitutable carbon atoms of the carbocyclic group being intended as possible points of attachment.

"Arylalkyl" refers to an aryl group, as defined above, bound to an alkyl group, as defined above, wherein said alkyl group is the point of attachment.

"Cycloalkyl" refers to a non-aromatic mono- or multicyclic ring system comprising about 3 to about 10 carbon atoms, preferably about 5 to about 10 carbon atoms. Preferred cycloalkyl rings contain about 3 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantly and the like.

"Halogen" or "halo" refers to —F, —Cl, —Br, or —I.

"Heteroaryl" refers to cyclic groups, having 1 to 4 heteroatoms selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms. The rings do not contain adjacent oxygen and/or sulfur atoms. Examples include but are not limited to 5-membered rings such as isothiazolyl, isoxazolyl, oxazolyl, furazanyl, triazolyl, tetrazolyl, thiazolyl, thienyl, furanyl (furyl), pyrrolyl and pyrazolyl, and 6-membered rings such as pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide) and triazinyl, and bicyclic groups such as pteridinyl, indolyl (benzopyrrolyl), pyridopyrazinyl, isoquinolinyl, quinolinyl, naphthyridinyl. All available substitutable carbon and nitrogen atoms can be substituted as defined.

"Heterocycloalkyl" refers to a saturated carbocylic ring containing from 3 to 15 carbon atoms, preferably from 4 to 6 carbon atoms, which carbocyclic ring is interrupted by 1 to 3 hetero atoms selected from —O—, —S—, —SO—, —SO$_2$ or —NR$^{40}$— wherein R$^{40}$ represents H, C$_1$ to C$_6$ alkyl, arylalkyl, —C(O)R$^{30}$, —C(O)OR$^{30}$, or —C(O)N(R$^{30}$)$_2$ (wherein each R$^{30}$ is independently selected from the group consisting of H, alkyl, phenyl and benzyl). The rings do not contains adjacent oxygen and/or sulfur atoms. Examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl.

"Cycloalkylene" refers to a divalent cycloalkyl ring, e.g.

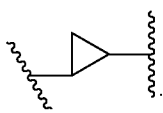

"Heterocycloalkylene" refers to a divalent heterocycloalkyl ring, e.g.

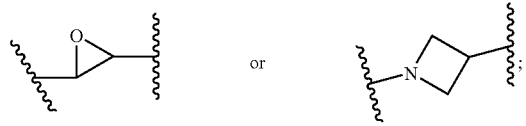

therefore, when R$^8$-alkylene is said to be interrupted by cycloalkylene or heterocycloalkylene, groups such as

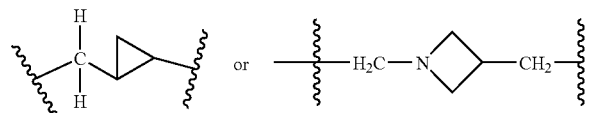

are contemplated.

for example in the structure

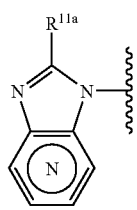

represents a nitrogen atom that is located at one of the 4 non-fused positions of the ring, i.e., positions 4, 5, 6 or 7 indicated below:

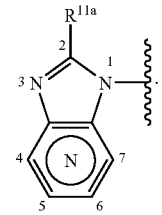

Similarly,

means that two nitrogens are located at any two of the 4 non-fused positions of the ring, e.g., the 4 and 6 positions, the 4 and 7 positions, or the 5 and 6 positions.

Also, as used herein, "upper airway" usually means the upper respiratory system, i.e., the nose, throat, and associated structures.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

A line drawn into a ring means that the indicated bond may be attached to any of the substitutable ring carbon atoms.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. The term "stable compound" or "stable structure" is meant to describe a compound that is sufficiently robust to survive isolation to a useful degree of purity from a reaction mixture, and formulation into an efficacious therapeutic agent.

When M is CH and an R$^4$ substituent is present on the ring (i.e., b is 1, 2 or 3), the R$^4$ substituent can replace the H on said carbon, e.g., the ring can be:

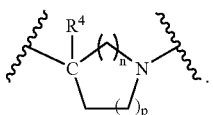

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyl-oxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N, N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$ alkyl, and the like.

Similarly, if a compound of formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)-ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of formula (I) incorporates an amine functional group, a prodrug can be formed by the replacement of a hydrogen atom in the amine group with a group such as, for example, R''-carbonyl, R''O-carbonyl, NR''R'''-carbonyl where R'' and R''' are each independently $(C_1-C_{10})$alkyl, $(C_3-C_7)$cycloalkyl, benzyl, or R''-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N- or di-N,N—$(C_1-C_6)$alkylamino morpholino, piperidin-1-yl or pyrrolidin-1-yl, and the like.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is water.

The compounds of formula (I) can form salts which are also within the scope of this invention. Reference to a compound of formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of formula (I), and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prod rug of enantiomers, stereoisomers, rotamers, tautomers, positional isomers, racemates or prodrugs of the inventive compounds.

Polymorphic forms of the compounds of formula (I), and of the salts, solvates, esters and prodrugs of the compounds of formula (I), are intended to be included in the present invention.

The phrase "at least one compound of formula (I)" means that one to three different compounds of formula (I) may be used in a pharmaceutical composition or method of treatment. In one embodiment one compound of formula (I) is used. Similarly, "at least one $H_1$ receptor antagonist" or "at least one other compound (or agent) for treating obesity, an obesity-related disorder, metabolic syndrome or a cognition deficit disorder" means that one to three different $H_1$ antagonists or other compounds may be used in a pharmaceutical composition or method of treatment. In one embodiment, one $H_1$ antagonist or one other compound for treating obesity, an obesity-related disorder, metabolic syndrome or a cognition deficit disorder is used in the combinations.

The term "obesity" as used herein, refers to a patient being overweight and having a body mass index (BMI) of 25 or greater. In one embodiment, an obese patient has a BMI of 25 or greater. In another embodiment, an obese patient has a BMI from 25 to 30. In another embodiment, an obese patient has a BMI greater than 30. In still another embodiment, an obese patient has a BMI greater than 40.

The term "obesity-related disorder" as used herein refers to any disorder which results from a patient having a BMI of 25 or greater. Non-limiting examples of an obesity-related disorder include edema, shortness of breath, sleep apnea, skin disorders and high blood pressure.

The term "metabolic syndrome" refers to a combination of risk factors for cardiovascular disease (CVD) identified in the National Cholesterol Education Program's Adult Treatment Panel III report. See for example the discussion by Grundy et al in *Circulation*, 109 (2004), 433-438. The components of metabolic syndrome are: 1) abdominal obesity; 2) atherogenic dyslipidemia; 3) raised blood pressure; 4) insulin resistance; 5) proinflammatory state; and 6) prothrombotic state.

Unless otherwise stated, the following abbreviations have the stated meanings:
Me=methyl; Et=ethyl; Bn=benzyl; Bu=butyl; Pr=propyl; Ph=phenyl; t-BOC=tert-butoxycarbonyl; Ac=acetyl; BINAP=2,2'-bis(diphenylphosphino)-1,1'binaphthyl; DCE=1,2-dichloroethane; DCM=dichloro-methane; DEAD=diethyl azodicarboxylate; DIPEA=N,N-diisopropylethylamine (Hunig's base); DMF=dimethylformamide; EDC=1-(3-dimethylaminopropyl)-3-ethylcarbodiimide; HOBT=1-hydroxybenzotriazole; NaBH(Oac)$_3$=sodium triacetoxyboro-hydride; PyBOP=benzotriazol-1-yloxytri-pyrrolidinophosphonium hexafluorophosphate; RT=room temperature; TFA=trifluoroacetic acid; THF=tetrahydrofuran; TEMPO=2,2,6,6-tetramethyl-1-piperidinyloxy, free radical; TLC=thin layer chromatography; MS=Mass Spectrometry; nM=nanomolar; Ki=Dissociation Constant for substrate/receptor complex.

The Compounds of Formula (I)

The invention provides compounds having the formula:

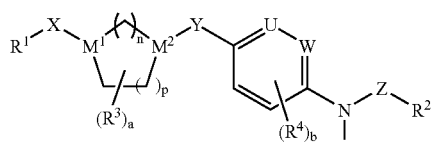

and pharmaceutically acceptable salts thereof, wherein $R^1$, $R^2$, $R^3$, $R^4$, $R^5$, $M^1$, $M^2$, U, V, W, X, Y, Z, a, b, n and p are defined above for the compounds of formula (I).

In one embodiment, $R^1$ is $R^{15}$-aryl, $R^{15}$-(6-membered heteroaryl),

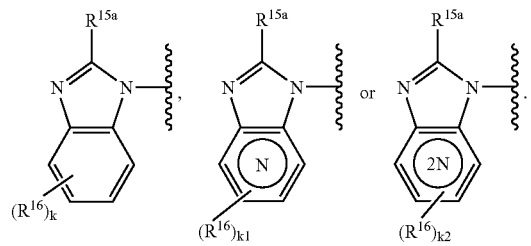

In another embodiment, $R^1$ is $R^{15}$-phenyl and $R^{15}$ is 1 to 4 substituents independently selected from the group consisting of H, halo, alkyl, haloalkyl or —CN.

In still another embodiment, $R^{15}$ is one or two substituents independently selected from H and halo.

In yet another embodiment, $R^{15}$ is one substituent selected from the group consisting of —CF$_3$, —CHF$_2$ and —CN.

In one embodiment, $R^1$ is $R^{15}$-pyridyl. In another embodiment, the 6-membered heteroaryl is 2-pyridyl.

In one embodiment, $R^{15}$ is 1-3 substituents independently selected from the group consisting of H, halo, alkyl, haloalkyl and —CN.

In another embodiment, $R^{15}$ is one or two substituents independently selected from the group consisting of H and halo.

In a further embodiment, $R^{15}$ is one substituent selected from the group consisting of —CF$_3$, —CHF$_2$ and —CN.

In one embodiment, $R^1$ is

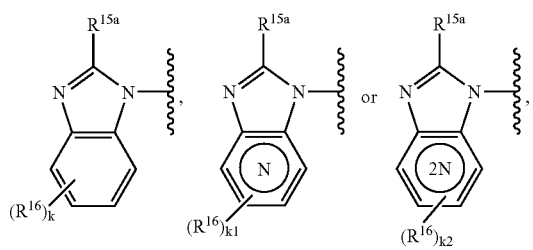

wherein $R^{15a}$ is $C_1$-$C_3$ alkyl, halo($C_1$-$C_3$)alkyl; $C_1$-$C_3$ alkoxy, $C_1$-$C_3$ alkylthio; $R^{21}$-phenyl or $R^{21}$-pyridyl; $R^{21}$ is 1-3 substituents independently selected from the group consisting of H, halo, alkyl, haloalkyl, —OCF$_3$, —CHF$_2$ or —CN; $R^{16}$ is as defined above; and k, k1 and k2 are each independently 0, 1 or 2.

In another embodiment, $R^1$ is

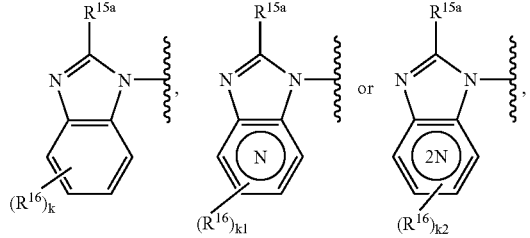

X is a bond and $M^1$ is

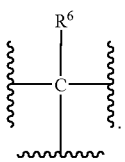

In still another embodiment, $R^1$ is

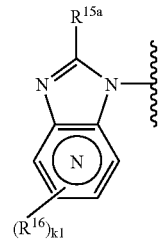

wherein $R^{15a}$ is (C$_1$-C$_3$)alkyl, C$_1$-C$_3$ alkoxy, C$_1$-C$_3$ alkylthio, $R^{21}$-phenyl or $R^{21}$-pyridyl; $R^{21}$ is 1 or 2 substituents independently selected from the group consisting of H, halo, alkyl and haloalkyl; $R^{16}$ is as defined above; and k1 is 0 or 1.

In another embodiment $R^1$ is

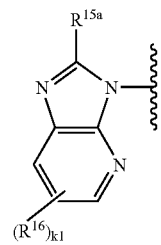

wherein $R^{15a}$ is —C$_2$F$_5$, —CF$_3$, C$_2$H$_5$—O—, CH$_3$—O—, C$_2$H$_5$—S—, CH$_3$—S—, $R^{21}$-phenyl or $R^{21}$-pyridyl; $R^{21}$ is 1 or 2 substituents independently selected from the group consisting of H, F, Cl, —CH$_3$, and —CF$_3$; k1 is 0 or 1; and $R^{16}$ is F, Cl or —CF$_3$.

In one embodiment, n is 1.
In another embodiment, p is 1.
In one embodiment, a and b are each independently 0 or 1.
In another embodiment, a and b are each 0.
In still another embodiment, both U and W are CH.
In one embodiment, $M^1$ is $$\begin{array}{c} R^6 \\ | \\ -C- \\ | \\ H \end{array}$$

wherein $R^6$ is H, —NHC(O)$R^7$ or —N($R^7$)$_2$; and $R^7$ is alkyl.

In another embodiment, $M^1$ is $$\begin{array}{c} R^6 \\ | \\ -C- \\ | \\ H \end{array}$$

wherein $R^6$ is H.

In one embodiment, $M^2$ is preferably N.
In another embodiment, $R^5$ is H or alkyl.
X is preferably a single bond, —NHC(O)— or —C(N—O$R^{10}$)—, wherein $R^{10}$ is H or alkyl; more preferably, X is a single bond.
Y is preferably —O— or —C(=O)—, more preferably —C(=O)—.
Preferred compounds are those wherein $M^1$, $M^2$, n, p, X and Y are as defined in (a) or (b), with (a) being more preferred for compounds wherein $R^1$ is <image showing three benzimidazole structures with $R^{15a}$, $(R^{16})_k$, $(R^{16})_{k1}$, $(R^{16})_{k2}$ substituents> and (b) being preferred for compounds wherein $R^1$ is $R^{15}$-aryl or $R^{15}$-(6-membered heteroaryl).

In a further embodiment, Z is a bond.
In one embodiment, $R^3$ and $R^4$ are each independently H, alkyl, fluoro or —OH.
In another embodiment, $R^2$ is $R^{18}$-heteroaryl or $R^{18}$-heterocycloalkyl.
In still another embodiment, $R^2$ is a 5 or 6 membered $R^{18}$-heteroaryl or a 4, 5 or 6-membered $R^{18}$-heterocycloalkyl.
In yet another embodiment, $R^2$ is $R^{18}$-pyridyl, $R^{18}$-pyrimidyl, $R^{18}$-pyradazinyl, $R^{18}$-tetrahydropyranyl, $R^{18}$-azetidinyl, $R^{18}$-oxazolyl and $R^{18}$-thiazolyl.
In a further embodiment, $R^2$ is $R^{18}$-pyridyl, $R^{18}$-pyrimidyl, $R^{18}$-pyradazinyl, $R^{18}$-oxazolyl or $R^{18}$-thiazolyl, and $R^{18}$ is 1 or 2 substituents independently selected from the group consisting of H, —CH$_3$, —NH$_2$ and —NHCH$_3$.
In one embodiment, $R^2$ is $R^{18}$-tetrahydropyranyl or $R^{18}$-azetidinyl, and $R^{18}$ is 1 or 2 substituents independently selected from the group consisting of H and —CH$_3$.

In another embodiment, $R^2$ is 2-amino pyridyl, 2-amino oxazolyl, 2-amino thiazolyl, 1-methyl-azetidinyl and tetrahydropyranyl.
In another embodiment, $R^2$ is 2-amino pyridyl.
In one embodiment, the compounds of formula (I) have the formula (IA):

<image showing formula (IA)>

(IA)

and pharmaceutically acceptable salts thereof,
wherein
 $M^1$ is CR$^6$ or N;
 $M^2$ is CH or N;
 X is a bond, alkylene, —C(O)—, —C(=N—O—R$^a$)—, —N(R$^{12}$)—, —CH$_2$N(R$^{12}$)—, —C(=CH$_2$)—, —NHC(O)—, —SO$_2$—, such that when $M^1$ is N, X is not —N(R$^{12}$)— or —CH$_2$N(R$^{12}$)—;
 Y is —C(O)— when $M^2$ is N, and Y is —C(O) or O when $M^2$ is CH;
 Z is a bond;
 $R^1$ is $R^{15}$-arylalkyl, $R^{15}$-aryl, $R^{15}$-cycloalkyl, $R^{15}$-heteroaryl, $R^{15}$-heterocycloalkyl, fluorenyl, <image showing benzimidazole, imidazopyridine, benzodioxole, and benzimidazolone ring structures with $R^{15a}$, $R^{16}$, $R^{17}$, Q substituents>

$R^2$ is $R^{18}$-arylalkyl, $R^{18}$-alkyl, $R^{18}$-aryl, $R^{18}$-heteroaryl, or $R^{18}$-heterocycloalkyl;
each $R^3$ is independently selected from the group consisting of H, halo, alkyl, haloalkyl, —OH, alkoxy and —CN;
each $R^4$ is independently selected from the group consisting of H, alkyl, —OH, alkoxy, halo, —CF$_3$, —OCF$_3$, —NO$_2$ and —CN;

$R^5$ is H, alkyl or —C(O)alkyl;
$R^6$ is —H, —$NH_2$, —NH-alkyl, —CN, -hydroxy-substituted alkyl, —NHC(O)-alkyl, or —C(alkyl)(=N—$R^a$);
$R^{12}$ is —H or alkyl;
$R^{15}$ is —H, —CN, —O-phenyl, —OH, alkoxy, halo, alkyl, -benzyl, —$NH_2$, —$NO_2$, —$CF_3$, —$OCF_3$, —S-alkyl, phenyl, —C(O)O-alkyl, —C(O)alkyl, or —S—$CF_3$;
$R^{15a}$ is —H, or -heteroaryl (2-benzofuranyl, 2-quinolinyl, pyridyl);
$R^{16}$ is —$CF_3$, or halo;
$R^{17}$ is —H, alkoxy, or $R^2$-heterocycloalkylalkyl (—$CH_2CH_2$—(N-morpholinyl));
$R^{18}$ is —H, halo, —$NO_2$, or —$NH_2$;
$R^{21}$ is —H, halo or alkyl;
Q is O or S;
$R^a$ is —H, alkyl, or —$CH_2CF_3$;
a is 0 or 1;
b is 0 or 1;
k is 0, 1 or 2; and
k1 is 0, 1 or 2.
In one embodiment, a is 0.
In another embodiment, a is 1.
In one embodiment, b is 0.
In another embodiment, b is 1.
In one embodiment, k is 0.
In another embodiment, k is 1.
In one embodiment, k1 is 0.
In another embodiment, k1 is 1.
In one embodiment, Q is O.
In one embodiment, $R^1$ is $R^{15}$-arylalkyl.
In another embodiment, $R^1$ is $R^{15}$-aryl.
In another embodiment, $R^1$ is $R^{15}$-cycloalkyl.
In still another embodiment, $R^1$ is $R^{15}$-heteroaryl.
In another embodiment, $R^1$ is $R^{15}$-heterocycloalkyl.
In yet another embodiment, $R^1$ is fluorenyl.
In one embodiment, $R^1$ is $R^{15}$-phenyl or $R^{15}$-naphthyl.
In another embodiment, $R^1$ is $R^{15}$-cyclohexyl or $R^{15}$-cyclopropyl.
In another embodiment, $R^1$ is $R^{15}$-isoxazolyl, $R^{15}$-pyridyl, $R^{15}$-pyrimidinyl or $R^{15}$-pyridazinyl.
In still another embodiment, $R^1$ is $R^{15}$-piperazinyl, $R^{15}$-piperidinyl or $R^{15}$-morpholinyl.
In yet another embodiment, $R^1$ is:

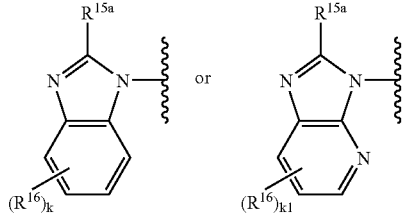

wherein $R^{15a}$ is benzofuranyl, quinolinyl or pyridyl, and $R^{16}$, k and k1 are as defined above for the compounds of formula (IA).
In one embodiment, $R^1$ is:

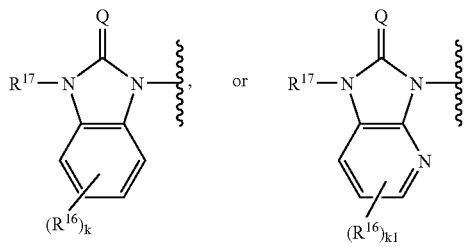

wherein $R^{17}$ is —H, alkoxy, or —$CH_2CH_2$—(N-morpholinyl), and $R^{16}$, k and k1 are as defined above for the compounds of formula (IA).
In one embodiment, $R^2$ is $R^{18}$-arylalkyl.
In another embodiment, $R^2$ is $R^{18}$-benzyl.
In another embodiment, $R^2$ is $R^{18}$-alkyl.
In still another embodiment, $R^2$ is $R^{18}$-aryl.
In another embodiment, $R^2$ is $R^{18}$-phenyl.
In yet another embodiment, $R^2$ is $R^{18}$-heteroaryl.
In one embodiment, $R^2$ is pyridyl.
In another embodiment, $R^2$ is —$NH_2$-substituted pyridyl.
In another embodiment, $R^2$ is 2-amino-pyridin-4-yl
In yet another embodiment, $R^2$ is pyrimidinyl.
In still another embodiment, $R^2$ is $R^{18}$-heterocycloalkyl.
In another embodiment, $R^2$ is tetrahydropyranyl.
In one embodiment, $R^{15a}$ is benzofuranyl, quinolinyl or pyridyl.
In one embodiment, $M^1$ is N.
In another embodiment, $M^1$ is $CR^6$.
In another embodiment, $M^1$ is CH.
In one embodiment, $M^2$ is N.
In another embodiment, $M^2$ is CH.
In one embodiment, X is a bond.
In another embodiment, X is alkylene.
In another embodiment, X is —$CH_2$—.
In still another embodiment, X is —$CH_2CH_2$—.
In another embodiment, X is —C(O)—.
In yet another embodiment, X is —C(=N—O—$R^a$)—.
In one embodiment, X is —C(=N—O—$CH_3$)—.
In another embodiment, X is —C(=N—OH)—.
In still another embodiment, X is —N($R^{12}$)—.
In yet another embodiment, X is NH.
In a further embodiment, X is —$CH_2$N($R^{12}$)—.
In another embodiment, X is —$CH_2$N($CH_3$)—.
In one embodiment, X is —C(=$CH_2$)—.
In another embodiment, X is —NHC(O)—.
In another embodiment, X is —$SO_2$—.
In one embodiment, Y is —C(O)— and $M^2$ is N.
In another embodiment, Y is —C(O)— and $M^2$ is CH.
In another embodiment, Y is —O— and $M^2$ is CH.
In one embodiment, $M^2$ is N, Y is —C(O)—.
In another embodiment, $M^1$ is N, $M^2$ is N, Y is —C(O)—.
In another embodiment, $M^1$ is CH, $M^2$ is N, Y is —C(O)—.
In still another embodiment, a is 0, b is 1, and $R^4$ is alkoxy or alkyl.
In yet another embodiment, $M^2$ is CH, Y is —C(O)—.
In a further embodiment, $M^2$ is CH, Y is —O—.
In another embodiment, $M^1$ is N, $M^2$ is CH, Y is —C(O)—.
In another embodiment, $M^1$ is N, $M^2$ is CH, Y is —O—.
In one embodiment, $M^1$ and $M^2$ are each N, X is —NHC(O)—, Y is —C(O)—, $R^1$ is phenyl, $R^2$ is 4-pyridyl and $R^5$ is methyl.
In another embodiment, $M^1$ and $M^2$ are each N, X is —NHC(O)—, Y is —C(O)—, $R^1$ is phenyl, $R^2$ is 4-pyridyl and R is H.
In one embodiment, $M^1$ is CH, $M^2$ is N, X is a bond, Y is —C(O)—, $R^1$ is phenyl, $R^2$ is 4-pyridyl and $R^5$ is methyl.
In another embodiment, $M^1$ is CH, $M^2$ is N, X is a bond, Y is —C(O)—, $R^1$ is phenyl, $R^2$ is 4-pyridyl and $R^5$ is H.
In another embodiment, $M^1$ is CH, $M^2$ is N, X is a bond, Y is —C(O)—, $R^1$ is phenyl, $R^2$ is 2-amino-pyridin-4-yl and $R^5$ is H.
In yet another embodiment, $M^1$ is CH, $M^2$ is N, X is —C(=$NOCH_3$), Y is —C(O)—, $R^1$ is phenyl, $R^2$ is 2-amino-pyridin-4-yl and $R^5$ is H.

Illustrative examples of the compounds of formula (I) include, but are not limited to, Compounds 1A-160A as set forth below in the Examples section.

Methods for Making the Compounds of Formula (I)

The compounds of this invention can be prepared via procedures known to those skilled in the art. Compounds described in this invention are typically prepared by preassembling the right portion of the molecule (CD fragment) and then building onto it the left portion of the molecule in a one-step (AB+CD) or two-step (B+CD, followed by A+BCD) approach (see Schemes 2-4, below).

The CD portion of the molecule is typically assembled as shown in Scheme 1:

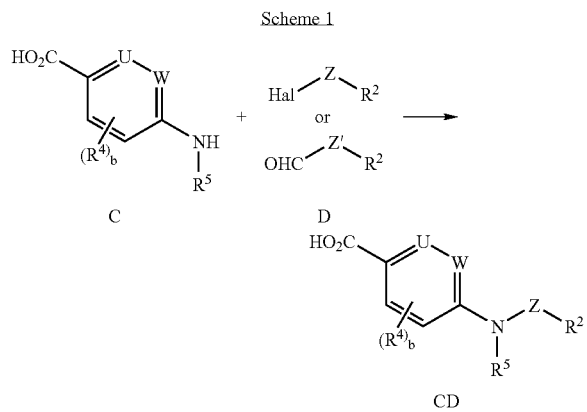

A typical reaction involves thermal reaction of the appropriately functionalized aniline C with halogen-substituted reagent D wherein $R^2$ is heteroaryl (Z is a single bond); the procedure is applicable to reaction of an aniline C with halogen-substituted aryl, cycloalkyl and heterocycloalkyl versions of fragment D. In cases, where linker Z is a $C_1$-$C_6$ alkyl or alkenyl moiety (Z'), a reductive amination or a nucleophilic substitution process between the aniline C and an appropriate aldehyde or alkyl halide reagent D leads to CD.

Where $M^2$ is nitrogen, construction of the link between the CD and the AB (or alternatively, B) fragments of the molecule is typically accomplished through amide coupling of the pre-installed carboxylic acid functionality of the C fragment and the corresponding secondary amine functionality of the B fragment. See Scheme 2:

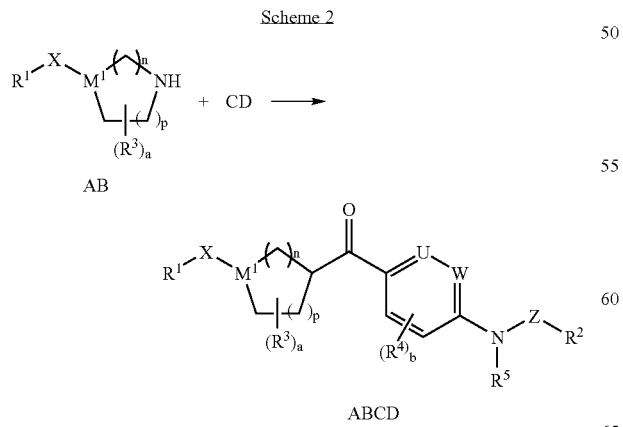

Pre-installation of a different functional group on the fragment C in place of the carboxylic acid functionality, e.g. a hydroxyl, halogen or sulfonyl moiety, allows formation of different types of Y moieties as the B—C links, as shown in Scheme 3:

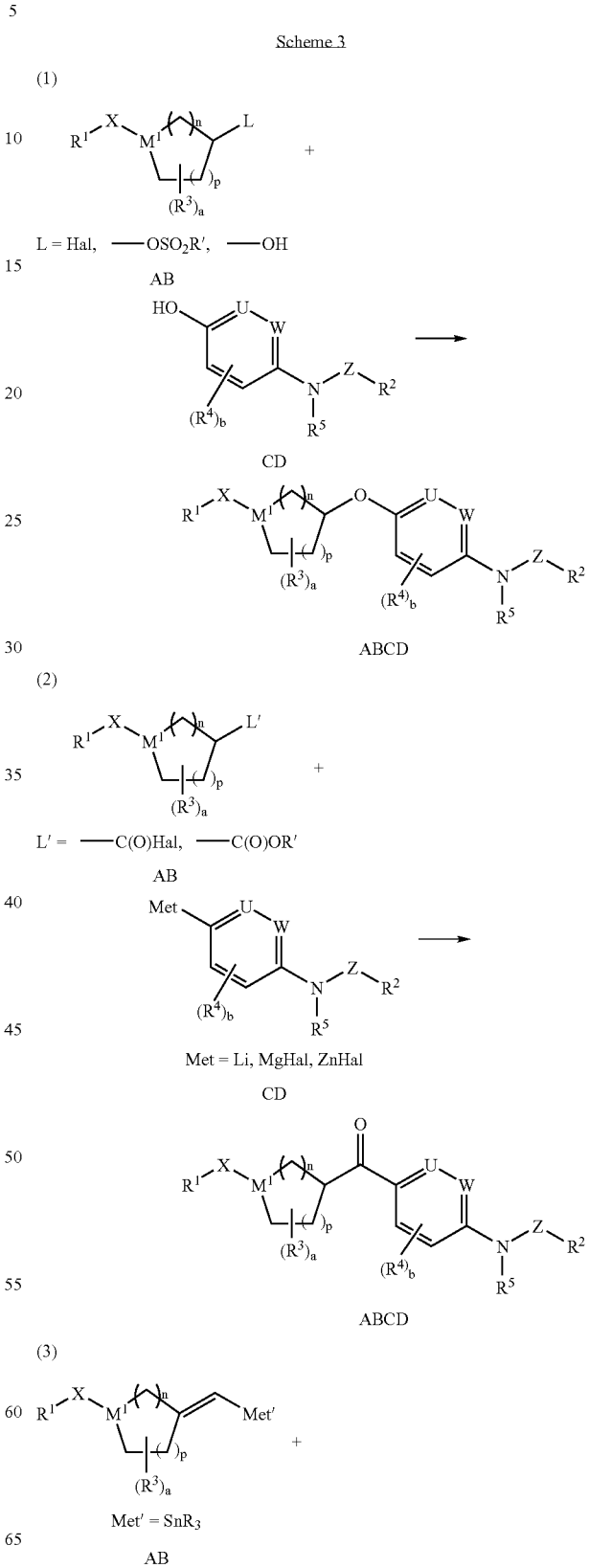

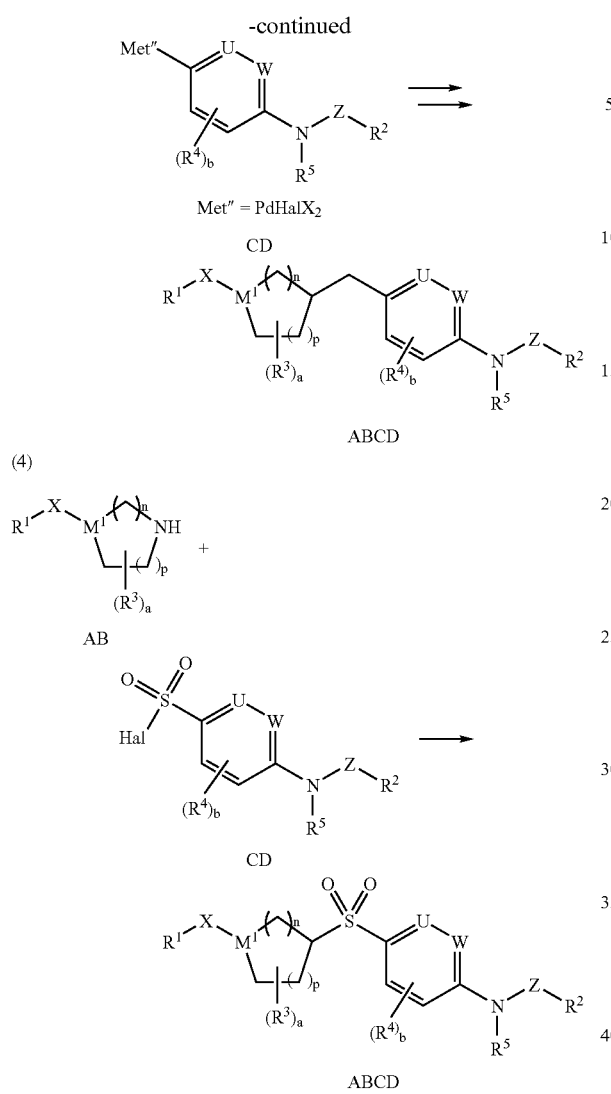

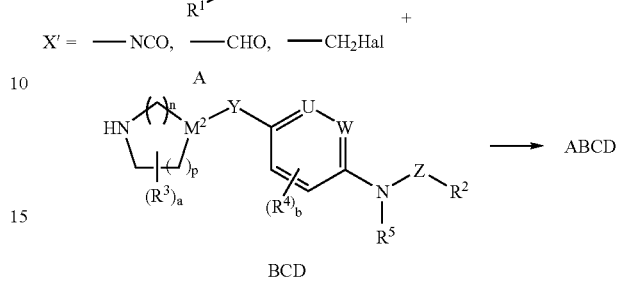

present in the BCD fragment. A non-limiting example of this approach (when $M^1$ is nitrogen) is shown in Scheme 4.

Suitable reactions for achieving B—C coupling include, but are not limited to, (1) a Mitsunobu reaction or nucleophilic substitution with a phenolate anion (i.e., Y is —O—, $M^2$=C); (2) metal-halogen exchange, followed by the addition of the corresponding C-arylmetal (e.g., catalyzed by a transition metal catalyst) species to the appropriate B-fragment electrophile (Y=—C(O)—, $M^2$=C), optionally followed by the reduction of the ketone (Y=$CH_2$, $M^2$=C); (3) transition-metal catalyzed coupling of the C-arylhalide with an appropriate vinyl metal species, derived from B (Y=$CH_2$, $M^2$=C), followed by the reduction of the double bond; or (4) reaction of the B-ring secondary amine with a C-ring sulfonyl chloride (Y=$SO_2$).

A variety of approaches to the construction of the corresponding AB fragments are known in the art. Synthetic approaches in most cases are dictated by the particular nature of the AB fragment. Some approaches to the AB fragments are illustrated by the specific examples below. In some instances, a stepwise approach to the construction of left side of the molecule (B+CD, followed by A+BCD) is more convenient. This approach is useful, if the A+BCD coupling process conditions are tolerated by the functionalities already Uses of the Compounds of Formula (I)

The compounds of formula (I) are useful for treating or preventing a Condition. Accordingly, the present invention provides methods for treating or preventing a Condition in a patient, comprising administering to the patient an effective amount of at least one compound of formula (I) or a pharmaceutically acceptable salt or solvate thereof.

In one embodiment, the compounds of formula (I) are useful for treating congestion, metabolic syndrome, obesity, an obesity-related disorder or a cognition deficit disorder.

In another embodiment, the compounds of formula (I) are useful for treating obesity or an obesity-related disorder.

In another embodiment, the compounds of formula (I) are useful for treating diabetes. There are two major forms of diabetes: Type I diabetes (also referred to as insulin-dependent diabetes or NIDDM) and Type II diabetes (also referred to as noninsulin dependent diabetes or NIDDM). In one embodiment, the compounds of formula (I) are useful for treating Type I diabetes. In another embodiment, the compounds of formula (I) are useful for treating Type II diabetes.

Combination Therapy

The present methods for treating or preventing a Condition can further comprise administering one or more additional therapeutic agents in addition to the at least one compound of formula (I). Additional therapeutic agents useful in the present methods include, but are not limited to, $H_1$ receptor antagonists, weight-loss agents, HMG-CoA reductase inhibitors, sterol absorption inhibitors, anti-diabetic agents, any agent useful for treating obesity, an obesity-related disorder, any agent useful for treating metabolic syndrome, any agent useful for treating a cognition deficit disorder, or any combination of two or more of these additional therapeutic agents.

In one embodiment, the compounds of formula (I) can be combined with an $H_1$ receptor antagonist (i.e., the compounds of formula (I) can be combined with an $H_1$ receptor antagonist in a pharmaceutical composition, or the compounds of formula (I) can be administered with an $H_1$ receptor antagonist).

Numerous chemical substances are known to have histamine $H_1$ receptor antagonist activity and can therefore be used in the methods of this invention. Representative $H_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

In one embodiment, said $H_1$ receptor antagonist is selected from: azatadine, brompheniramine, cetirizine, chlorpheniramine, carebastine, descarboethoxyloratadine, diphenhydramine, ebastine, fexofenadine, loratadine, or norastemizole. More preferably, said $H_1$ antagonist is selected from loratadine, descarboethoxyloratadine, fexofenadine or cetirizine.

In one embodiment, in the above combinations of $H_3$ and $H_1$ antagonists, nasal congestion is treated.

Weight-loss agents include appetite suppressants, metabolic rate enhancers and nutrient absorption inhibitors. Appetite suppressant agents useful for treating obesity or metabolic syndrome include cannabinoid receptor 1 ($CB_1$) antagonists or inverse agonists (e.g., rimonabant); NeuropeptideY (NPY1, NPY2, NPY4 and NPY5) antagonists; metabotropic glutamate subtype 5 receptor ($mGluR^5$) antagonists (e.g., 2-methyl-6-(phenylethynyl)-pyridine and 3[(2-methyl-1,4-thiazol-4-yl)ethynyl]pyridine); melanin-concentrating hormone receptor (MCH1R and MCH2R) antagonists; melanocortin receptor agonists (e.g., Melanotan-II and Mc4r agonists); serotonin uptake inhibitors (e.g., dexfenfluramine and fluoxetine); serotonin (5HT) transport inhibitors (e.g., paroxetine, fluoxetine, fenfluramine, fluvoxamine, sertaline and imipramine); norepinephrine (NE) transporter inhibitors (e.g., desipramine, talsupram and nomifensine); ghrelin antagonists; leptin or derivatives thereof; opioid antagonists (e.g., nalmefene, 3-methoxynaltrexone, naloxone and nalterxone); orexin antagonists; bombesin receptor subtype 3 (BRS3) agonists; Cholecystokinin-A (CCK-A) agonists; ciliary neurotrophic factor (CNTF) or derivatives thereof (e.g., butabindide and axokine); monoamine reuptake inhibitors (e.g., sibutramine); glucagons-like peptide 1 (GLP-1) agonists; topiramate; and phytopharm compound 57. Metabolic rate enhancers include acetyl-CoA carboxylase-2 (ACC2) inhibitors; beta adrenergic receptor 3 (β3) agonists; diacylglycerol acyltransferase inhibitors (DGAT1 and DGAT2); fatty acid synthase (FAS) inhibitors (e.g., Cerulenin); phosphodiesterase (PDE) inhibitors (e.g., theophylline, pentoxifylline, zaprinast, sildenafil, amrinone, milrinone, cilostamide, rolipram and cilomilast); thyroid hormone β agonists; uncoupling protein activators (UCP-1, 2 or 3) (e.g., phytanic acid, 4-[(E)-2-(5,6,7,8-tetramethyl-2-naphthalenyl)-1-propenyl]benzoic acid and retinoic acid); acyl-estrogens (e.g., oleoyl-estrone); glucocorticoid antagonists; 11-beta hydroxyl steroid dehydrogenase type 1 (11β HSD-1) inhibitors; melanocortin-3 receptor (Mc3r) agonists; and stearoyl-CoA desaturase-1 (SCD-1) compounds. Nutrient absorption inhibitors include lipase inhibitors (e.g., orlistat, lipstatin, tetrahydrolipstatin, teasaponin and diethylumbelliferyl phosphate); fatty acid transporter inhibitors; dicarboxylate transporter inhibitors; glucose transporter inhibitors; and phosphate transporter inhibitors.

Specific compounds for use in the combination for treating obesity and metabolic syndrome include rimonabant, 2-methyl-6-(phenylethynyl)-pyridine, 3[(2-methyl-1,4-thiazol-4-yl)ethynyl]pyridine, Melanotan-II, dexfenfluramine, fluoxetine, paroxetine, fenfluramine, fluvoxamine, sertaline, imipramine, desipramine, talsupram, nomifensine, leptin, nalmefene, 3-methoxynaltrexone, naloxone, nalterxone, butabindide, axokine, sibutramine, topiramate, phytopharm compound 57, Cerulenin, theophylline, pentoxifylline, zaprinast, sildenafil, amrinone, milrinone, cilostamide, rolipram, cilomilast, phytanic acid, 4-[(E)-2-(5,6,7,8-tetramethyl-2-naphthalenyl)-1-propenyl]benzoic acid, retinoic acid, oleoyl-estrone, orlistat, lipstatin, tetrahydrolipstatin, teasaponin and diethylumbelliferyl phosphate.

Preferred compounds for use in the combination for treating obesity and metabolic syndrome include rimonabant, dexfenfluramine, fenfluramine, phentermine, leptin, nalmefene, axokine, sibutramine, topiramate, phytopharm compound 57, oleoyl-estrone and orlistat.

Also preferred are combinations of at least one compound of formula (I) and one or more HMG-CoA reductase inhibitors and/or one or more substituted azetidinone or substituted β-lactam sterol absorption inhibitors for treating metabolic syndrome or obesity.

Typical HMG-CoA reductase inhibitors include statins such as lovastatin, simvastatin, pravastatin, atorvastatin, fluvastatin, resuvastatin, cerivastatin, rivastatin and pitavastatin. In one embodiment, the HMG-CoA reductase inhibitor is simvastatin.

As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5α-campestanol, 5α-sitostanol), and/or mixtures thereof, when administered in a therapeutically effective (sterol and/or 5α-stanol absorption inhibiting) amount to a mammal or human.

Non-limiting examples of suitable substituted azetidinones and methods of making the same include those disclosed in U.S. Pat. Nos. RE 37,721, 5,306,817, 5,561,227, 5,618,707, 5,624,920, 5,631,365, 5,656,624, 5,627,176, 5,633,246, 5,661,145, 5,688,785, 5,688,787, 5,688,990, 5,698,548, 5,728,827, 5,739,321, 5,744,467, 5,756,470, 5,767,115, 5,846,966, 5,856,473, 5,886,171, 5,919,672, 6,093,812, 6,096,883, 6,133,001, 6,207,822, 6,627,757, 6,632,933, U.S. Patent Publication Nos. 2003/0105028, 2004/0180860, 2004/0180861, and 2004/0198700, N-sulfonyl-2-azetidinones such as are disclosed in U.S. Pat. No. 4,983,597, ethyl 4-(2-oxoazetidin-4-yl)phenoxy-alkanoates such as are disclosed in Ram et al., Indian J. Chem. Sect. B. 29B, 12 (1990), p. 1134-7, and diphenyl azetidinones and derivatives disclosed in U.S. Patent Publication Nos. 2002/0039774, 2002/0128252, 2002/0128253 and 2002/0137689, and PCT Published Application Nos. WO 2002/066464, WO 04/000805, WO 04/005247, WO 04/000804, WO 04/000803, WO 04/014947, WO 04/087655, WO 05/009955, WO 05/023305, WO 05/021495, WO 05/021497, WO 05/044256, WO 05/042692, WO 05/033100, WO 05/030225, WO 05/047248, WO 05/046662, WO 05/061451, WO 05/061452, WO 05/062824, WO 05/02897, WO 05/000353, each of which is incorporated by reference herein.

An example of a suitable substituted azetidinone compound is represented by Formula (A) (ezetimibe) below:

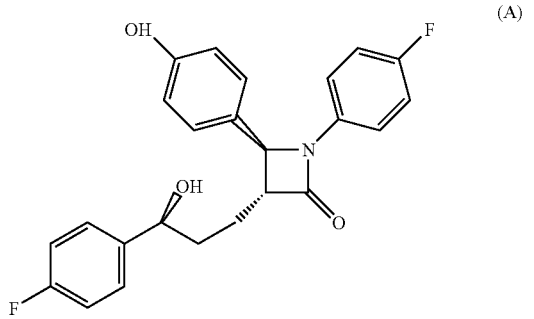

or pharmaceutically acceptable salts or solvates of the compound of Formula (A). The compound of Formula (A) can be in anhydrous or hydrated form. A product containing ezetimibe compound is commercially available as ZETIA® ezetimibe formulation from MSP Pharmaceuticals.

Typical compounds for use in combination with an $H_3$ antagonist of this invention for the treatment of a cognition deficit disorder are atomoxetine and dexmethylphenidate for the treatment of ADHD, olanzapine, risperidone or aripiprazole for treatment of schizophrenia, and donepezil, heptylphysostigmine, tacrine, rivastigmine or galantamine for the treatment of Alzheimer's Disease.

In one embodiment, the compounds of formula (I) can be co-administered with an anti-diabetic agent for treating diabetes.

Examples of anti-diabetic agents useful in the present methods for treating diabetes include sulfonylureas, insulin sensitizers (such as PPAR agonists, DPPIV inhibitors, PTP-1B inhibitors and glucokinase activators), α-glucosidase inhibitors, insulin secretagogues, hepatic glucose output lowering compounds, anti-obesity agents, antihypertensive agents, meglitinides, insulin and insulin-containing compositions.

In one embodiment, the anti-diabetic agent is an insulin sensitizer or a sulfonylurea.

Non-limiting examples of sulfonylureas include glipizide, tolbutamide, glyburide, glimepiride, chlorpropamide, acetohexamide, gliamilide, gliclazide, glibenclamide and tolazamide. Insulin sensitizers include PPAR-γ agonists described in detail above, preferably troglitazone, rosiglitazone, pioglitazone and englitazone; biguanidines such as mefformin and phenformin; DPPIV inhibitors such as sitagliptin, saxagliptin, denagliptin and vildagliptin; PTP-1B inhibitors; and glucokinase activators. α-Glucosidase inhibitors that can be useful in treating type II diabetes include miglitol, acarbose, and voglibose. Hepatic glucose output lowering drugs include Glucophage and Glucophage XR. Insulin secretagogues include sulfonylurea and non-sulfonylurea drugs such as GLP-1, exendin, GIP, secretin, glipizide, chlorpropamide, nateglinide, meglitinide, glibenclamide, repaglinide and glimepiride. Insulin includes all formulations of insulin, including long acting and short acting forms of insulin.

Non-limiting examples of anti-obesity agents useful in the present methods for treating diabetes include CB1 antagonists or inverse agonists such as rimonabant, neuropeptide Y antagonists, MCR4 agonists, MCH receptor antagonists, histamine H3 receptor antagonists or inverse agonists, leptin, appetite suppressants such as sibutramine, and lipase inhibitors such as xenical.

Non-limiting examples of antihypertensive agents useful in the present methods for treating diabetes include β-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

Non-limiting examples of meglitinides useful in the present methods for treating diabetes include repaglinide and nateglinide.

Non-limiting examples of insulin sensitizers include biguanides, such as mefformin and thiazolidinediones.

In one embodiment, the insulin sensitizer is a thiazolidinedione.

Non-limiting examples of antidiabetic agents that slow or block the breakdown of starches and certain sugars and are suitable for use in the compositions and methods of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of orally administrable insulin and insulin containing compositions include AL-401 from AutoImmune, and the compositions disclosed in U.S. Pat. Nos. 4,579,730; 4,849,405; 4,963,526; 5,642,868; 5,763,396; 5,824,638; 5,843,866; 6,153,632; 6,191,105; and International Publication No. WO 85/05029, each of which is incorporated herein by reference.

In one embodiment, the compounds of formula (I) can be co-administered with an anti-diabetic agent for treating obesity or an obesity-related disorder.

Anti-diabetic agents useful in the present methods for treating obesity or an obesity-related disorder include, but are not limited to the anti-diabetic agents listed above herein.

In the combination therapies of the present invention, the at least one compound of formula (I) and the one or more additional therapeutic agents can be administered simultaneously (at the same time, in a single dosage form or in separate dosage forms) or sequentially (first one and then another, etc. . . . over a period of time) in any order.

Pharmaceutical Compositions and Administration

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A.

Gennaro (ed.), *The Science and Practice of Pharmacy*, 20th Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

In one embodiment, the compound of formula (I) is administered orally.

In one embodiment, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

When the invention comprises a combination of $H_3$ antagonist and $H_1$ antagonist compounds, the two active components may be co-administered simultaneously or sequentially, or a single pharmaceutical composition comprising a $H_3$ antagonist and an $H_1$ antagonist in a pharmaceutically acceptable carrier can be administered. The components of the combination can be administered individually or together in any conventional dosage form such as capsule, tablet, powder, cachet, suspension, solution, suppository, nasal spray, etc. The dosage of the $H_1$ antagonist can be determined from published material, and may range from about 1 to about 1000 mg per dose. When used in combination, the dosage levels of the individual components are preferably lower than the recommended individual dosages because of the advantageous effect of the combination.

When separate $H_3$ and $H_1$ antagonist pharmaceutical compositions are to be administered, they can be provided in a kit comprising in a single package, one container comprising an $H_3$ antagonist in a pharmaceutically acceptable carrier, and a separate container comprising an $H_1$ antagonist in a pharmaceutically acceptable carrier, with the $H_3$ and $H_1$ antagonists being present in amounts such that the combination is therapeutically effective. A kit is advantageous for administering a combination when, for example, the components must be administered at different time intervals or when they are in different dosage forms.

Similarly, when the invention comprises a combination of $H_3$ antagonist and another compound for treating obesity, an obesity-related disorder, metabolic syndrome or a cognition deficit disorder, the two active components may be co-administered simultaneously or sequentially, or a single pharmaceutical composition comprising a $H_3$ antagonist and another compound in a pharmaceutically acceptable carrier can be administered. The components of the combination can be administered individually or together in any conventional dosage form such as capsule, tablet, powder, cachet, suspension, solution, suppository, nasal spray, etc. The dosage of the other compound for treating obesity, an obesity-related disorder, metabolic syndrome or a cognition deficit disorder can be determined from published material, and may range from about 1 to about 1000 mg per dose.

Kits

When separate pharmaceutical compositions comprising an $H_3$ antagonist and another compound for treating obesity, an obesity-related disorder, metabolic syndrome or a cognition deficit disorder are to be administered, they can be provided in a kit comprising in a single package, one container comprising an $H_3$ antagonist in a pharmaceutically acceptable carrier, and a separate container comprising a compound for treating obesity, an obesity-related disorder, metabolic syndrome or a cognition deficit disorder in a pharmaceutically acceptable carrier, with the $H_3$ antagonists and other compounds being present in amounts such that the combination is therapeutically effective. A kit is advantageous for administering a combination when, for example, the components must be administered at different time intervals or when they are in different dosage forms.

Compounds of formula (I) can be prepared by the general methods outlined above. Specifically exemplified compounds were prepared as described in the examples below, from starting materials known in the art or prepared as described below. These examples are being provided to further illustrate the present invention. They are for illustrative purposes only; the scope of the invention is not to be considered limited in any way thereby.

EXAMPLES

General Methods

The starting materials and reagents used in preparing compounds described are either available from commercial suppliers such as Aldrich Chemical Co. (Wisconsin, USA) and Acros Organics Co. (New Jersey, USA) or were prepared using methods well-known to those skilled in the art of organic synthesis. All commercially purchased solvents and reagents were used as received. LCMS analysis was performed using an Applied Biosystems API-100 mass spectrometer equipped with a Shimadzu SCL-10A LC column: Altech platinum C18, 3 um, 33 mm×7 mm ID; gradient flow: 0 minutes, 10% $CH_3CN$; 5 minutes, 95% $CH_3CN$; 7 minutes, 95% $CH_3CN$; 7.5 minutes, 10% $CH_3CN$; 9 minutes, stop. Flash column chromatography was performed using Selecto Scientific flash silica gel, 32-63 mesh. Analytical and preparative TLC was performed using Analtech Silica gel GF plates. Chiral HPLC was performed using a Varian PrepStar system equipped with a Chiralpak OD column (Chiral Technologies).

Example 1

Preparation of Compound 1A

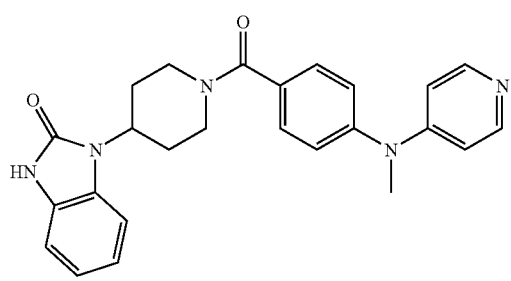

1A

Step 1:

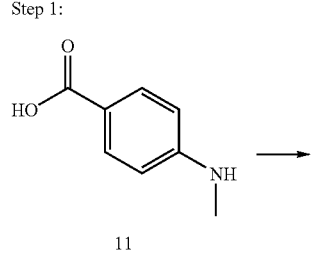

11

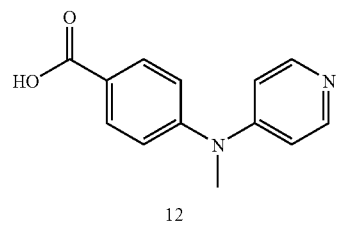

12

A mixture of amino acid 11 (1.0 g; 6.62 mmol) and 4-bromopyridine hydrochloride (1.54 g; 7.94 mmol) was heated until melted, and then the temperature was maintained for 1 h. The mixture was cooled to produce crude 12 as a brown solid, which was used directly without purification.

Step 2:

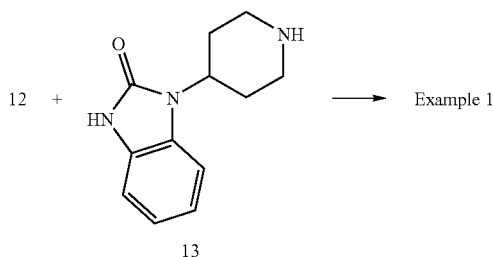

A mixture of crude 12 from Step 1, benzimidazolone 13 (1.43 g; 6.60 mmol), HOBT (1.34 g; 9.92 mmol) and EDC (1.90 g; 9.90 mmol) was stirred in DMF (20 ml) at room temperature overnight. DMF was removed under vacuum and the residue was partitioned between aqueous NaHCO$_3$ and CH$_2$Cl$_2$. The organic phase was separated, washed with brine, dried (Na$_2$SO$_4$) and concentrated. The residue was flash chromatographed (5% 2.3M NH$_3$ in MeOH/CH$_2$Cl$_2$) to produce 0.11 g of title compound as a white solid. MH$^+$ 428

Example 2

Preparation of Compound 2A

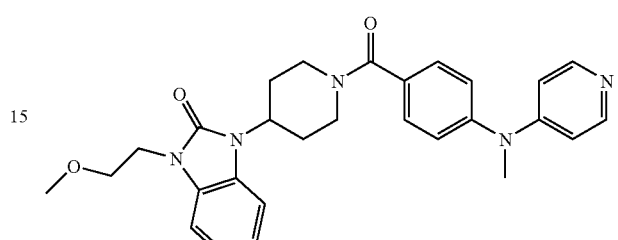

2A

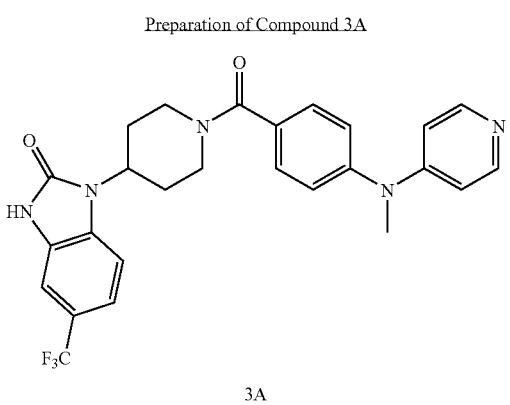

14

Example 2

Compound 14 was prepared as described in US 2004/0048843.

A mixture of crude 12 from Example 1, Step 1, amine 14 (1.82 g; 6.6 mmol), HATU (3.0 g; 7.89 mmol) and Et$_3$N (1.0 ml) in DMF (20 ml) was stirred at room temperature overnight. DMF was removed under vacuum, the residue was dissolved in MeOH and treated with diethylaminomethyl-polystyrene resin until basic. The mixture was filtered and concentrated. The residue was flash chromatographed (5% MeOH/CH$_2$Cl$_2$ with 1% NH$_4$OH) to provide 1.61 g of the title compound as a white solid. MH$^+$ 486

Example 3

Preparation of Compound 3A

3A

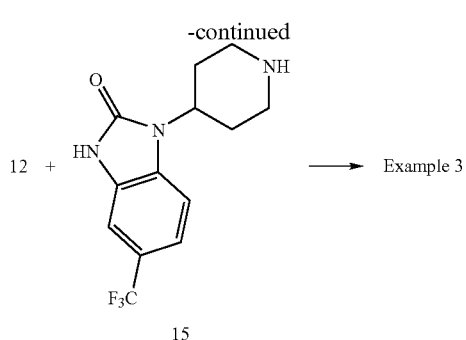

15

Compound 15 was prepared as described in US 2004/0048843.

Compounds 12 and 15 were converted into the title compound using the procedure described in Example 1, Step 2. MH+ 496

Example 4

Preparation of Compound 4A

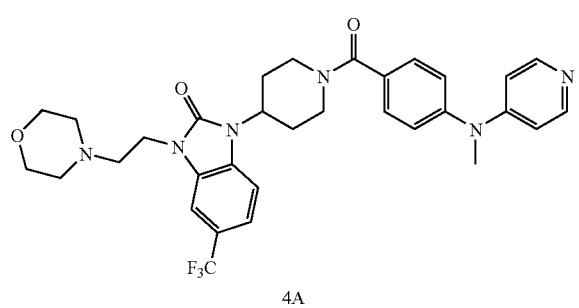

4A

Step 1:

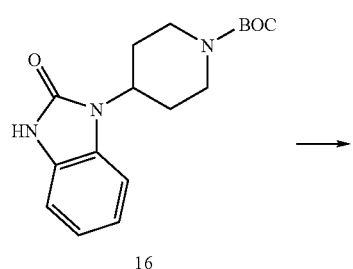

16

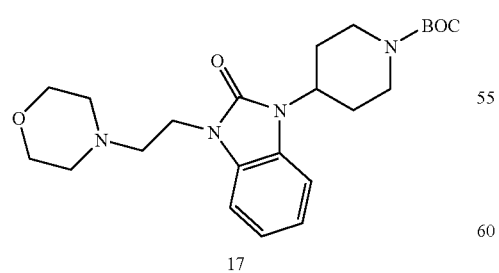

17

Compound 16 was prepared as described in US 2004/0048843.

A mixture of benzimidazolone 16 (5.74 g; 18.1 mmol), N-(2-chloroethyl-morpholine)hydrochloride (5.07 g; 27.3 mmol), NaOH (2.53 g; 63.3 mmol), K$_2$CO$_3$ (5.01 g; 36.3 mmol) and tetrabutylammonium hydrosulfate (1.24 g; 3.65 mmol) in toluene (100 ml) was refluxed overnight. The reaction mixture was allowed to cool and was filtered. The filtrate was concentrated and the residue was flash chromatographed (2% MeOH/CH$_2$Cl$_2$) to produce 5.71 g of compound 17 as a white foam.

Step 2:

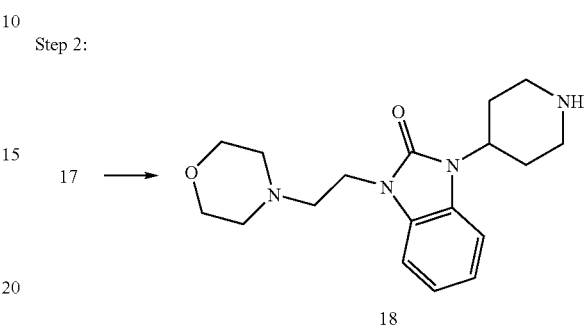

18

To a solution of compound 17 (7.81 g; 18.2 mmol) in CH$_2$Cl$_2$ (50 ml) was added 4.0M HCl solution in MeOH (28 ml, 109.9 mmol). The reaction mixture was stirred overnight and concentrated to produce 7.92 g of 18 as a hydrochloride salt.

Compound 18 was converted into the title compound using the procedure of Example 2. MH+ 541

Example 5

Preparation of Compound 5A

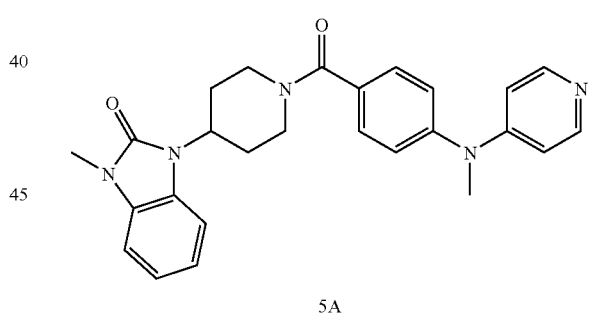

5A

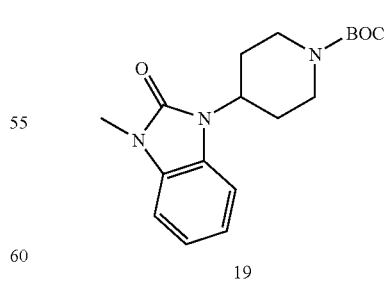

19

Compound 19 was prepared from compound 16 using the procedure described in US 2004/0048843.

Compound 19 was converted into the title compound using the procedure of Example 1, Step 2. MH+ 442

Example 6

Preparation of Compound 6A

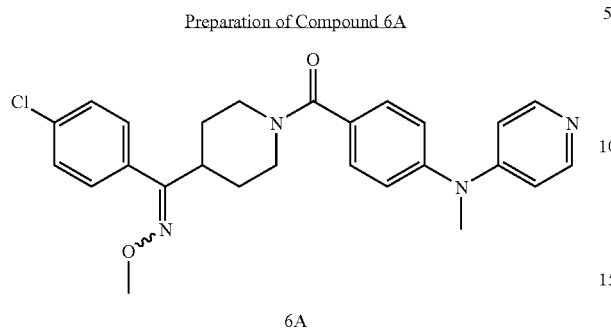

6A

Step 1:

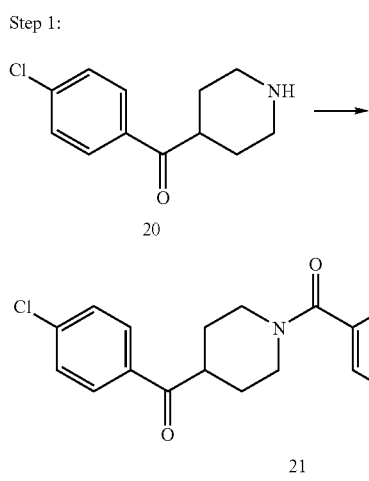

Compound 20 was converted into 21 using the procedure from Example 2.

Step 2:

To a solution of ketone 21 (160 mg; 0.37 mmol) in pyridine (20 ml) was added methoxylamine hydrochloride (62 mg; 0.74 mmol). The mixture was stirred overnight at 60° C., cooled and concentrated under vacuum. The residue was partitioned between aqueous $NaHCO_3$ and $CH_2Cl_2$, the organic phase was separated, washed with brine, dried ($Na_2SO_4$) and concentrated to produce 183 mg of the title compound (white solid) as a mixture of oxime isomers. $MH^+$ 463

Example 7

Preparation of Compound 7A

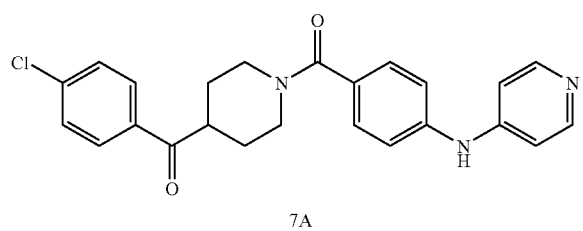

7A

Step 1:

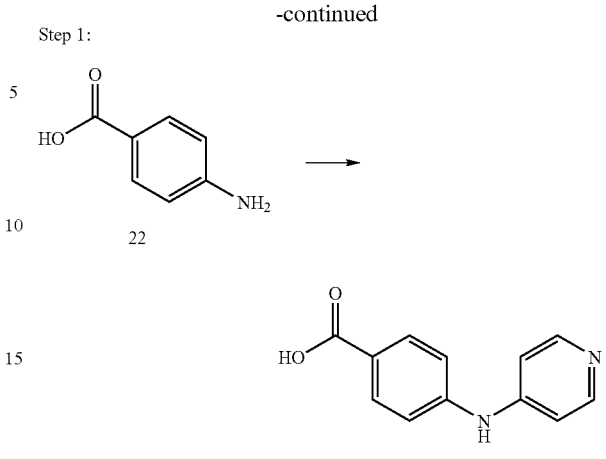

Using a procedure similar to Example 1, Step 1, 22 was used to prepare crude 23, to be used directly without purification.

Step 2:

Compound 23 was converted into the title compound using the procedure of Example 1, Step 2. $MH^+$ 420/

Example 8

Preparation of Compound 8A

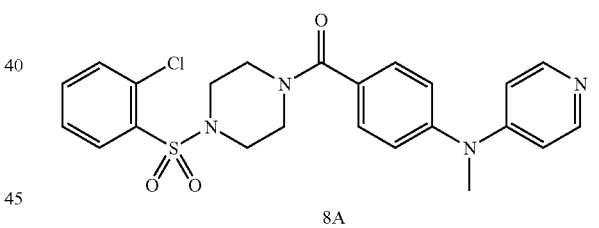

8A

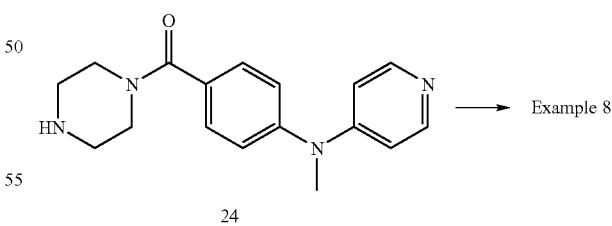

24

Compound 24 was prepared from acid 12 and N—BOC-piperazine using the procedure from Example 1, Step, followed by Example 4, Step 2.

A mixture of amine 24 (300 mg; 0.76 mmol), 2-chlorobenzenesulfonyl chloride (176 mg; 0.83 mmol) and $Et_3N$ (211 μl; 1.51 mmol) in $CH_2Cl_2$ was stirred for 3 h at room temperature. The mixture was subjected to aqueous work-up —$CH_2Cl_2$ extraction. The organic phase was concentrated to produce the title compound. $MH^+$ 428471

Example 9

Preparation of Compound 9A

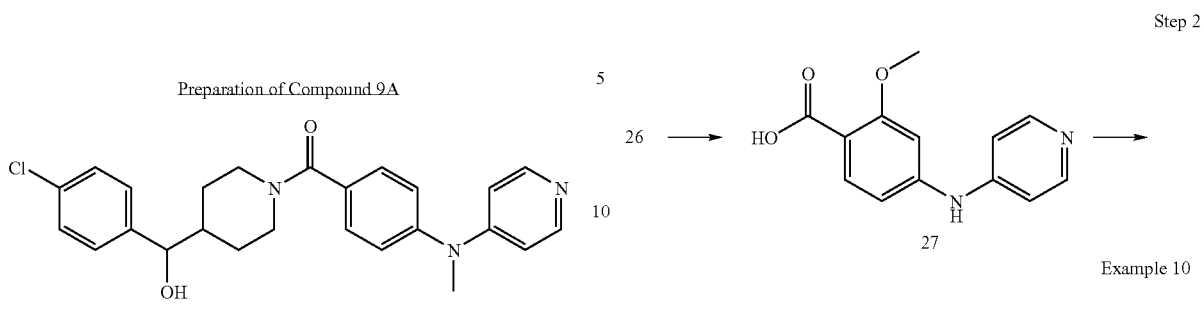

9A

The title compound was prepared in quantitative by yield by the NaBH$_4$ reduction in MeOH of the compound 21. MH$^+$ 436

Example 10

Preparation of Compound 10A

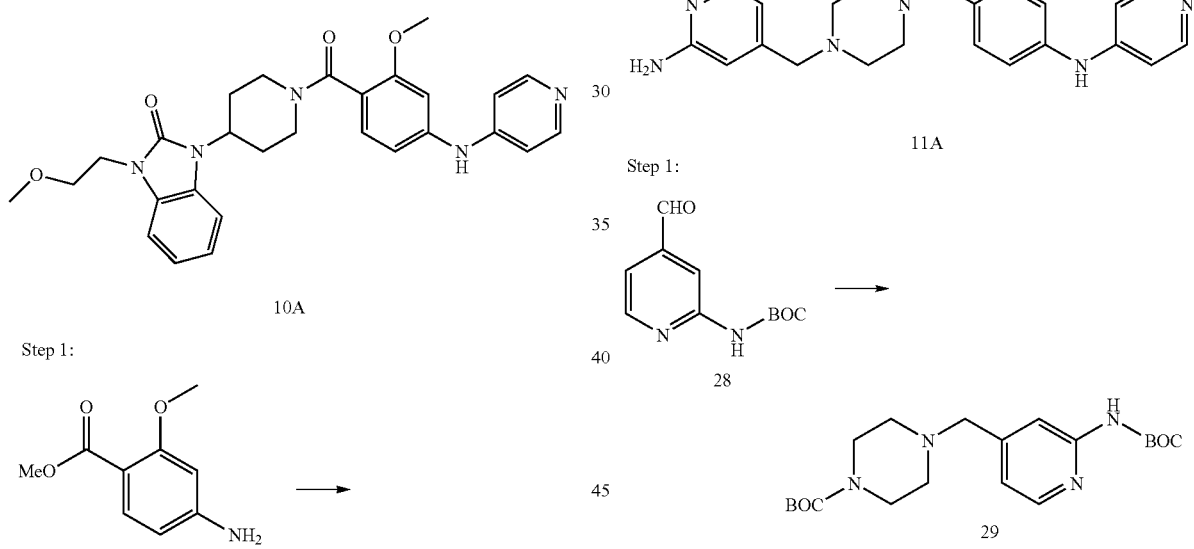

10A

Step 1:

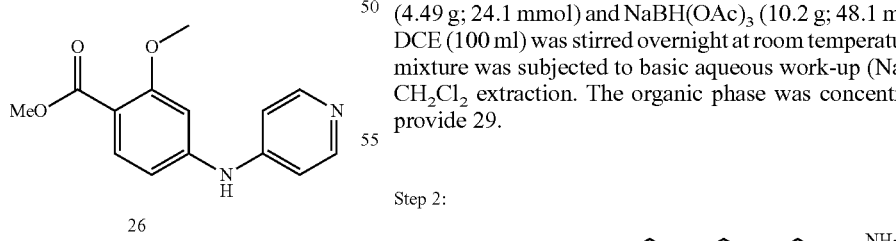

A mixture of aniline 25 (1.0 g; 5.5 mmol) and 4-bromopyridine hydrochloride (0.82 g; 4.2 mmol) in AcOH was stirred at reflux overnight. The mixture was concentrated under vacuum, and the residue was flash chromatographed (1% of 2.3M NH$_3$ in MeOH/CH$_2$Cl$_2$) to produce 0.052 g of compound 26.

Step 2:

26 → [structure 27]

Acid 27 was prepared from ester 26 through LiOH hydrolysis in acetone.

Acid 27 was converted into the title compound using the procedure of Example 1, Step 2. MH$^+$ 502

Example 11

Preparation of Compound 11A

[structure 11A]

Step 1:

[structure 28] → [structure 29]

A mixture of aldehyde 28 (5.33 g; 24.1 mmol) (prepared as described in U.S. Pat. No. 6,720,328), N—BOC-piperazine (4.49 g; 24.1 mmol) and NaBH(OAc)$_3$ (10.2 g; 48.1 mmol) in DCE (100 ml) was stirred overnight at room temperature. The mixture was subjected to basic aqueous work-up (NaOH)—CH$_2$Cl$_2$ extraction. The organic phase was concentrated to provide 29.

Step 2:

29 → [structure 30]

Crude 29 from step 1 was dissolved in 3M HCl in MeOH (200 ml) and the mixture was stirred at 60° C. for 4 h. The mixture was concentrated under vacuum, the residue was redissolved in MeOH, basified with NaOH, filtered through solid Na$_2$SO$_4$, and the filtrate was concentrated to provide 4.3 g of diamine 30 as a free base.

Step 3:

Compound 30 was converted into the title compound using the procedure of Example 1, Step 2. MH$^+$ 389

Example 12

Preparation of Compound 12A

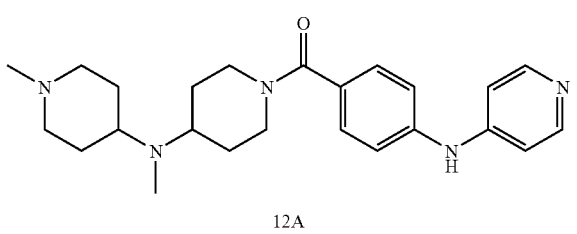

12A

Step 1:

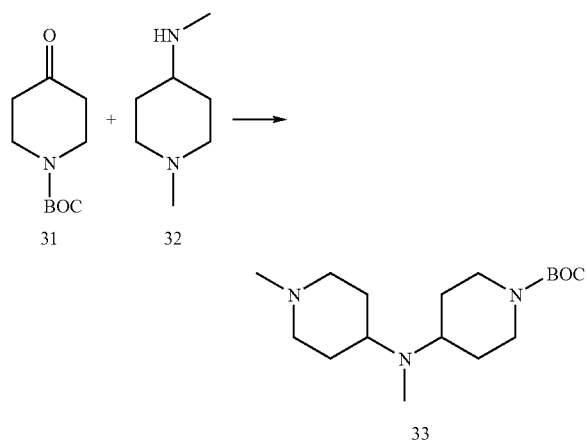

Compound 33 was prepared using the procedure of Example 11, Step 1.

Step 2:

Compound 33 was converted into the title compound using the procedures of Example 4, Step 2, followed by Example 1, Step 2. MH$^+$ 408

Example 13

Preparation of Compound 13A

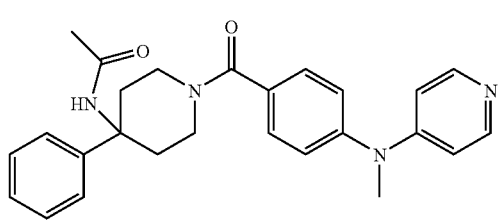

13A

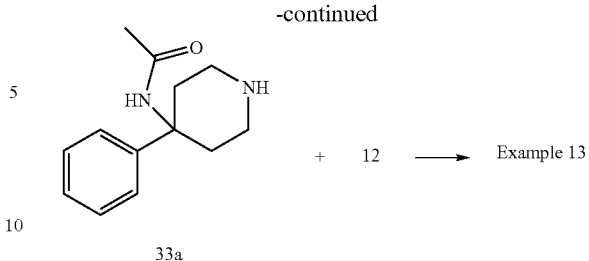

Compound 33a was prepared as described in *Bioorganic & Medicinal Chemistry Letters* 1993, 3, 925.

Compound 33a was converted into the title compound as described in Example 1, Step 2. MH$^+$ 429

Example 14

Preparation of Compound 14A

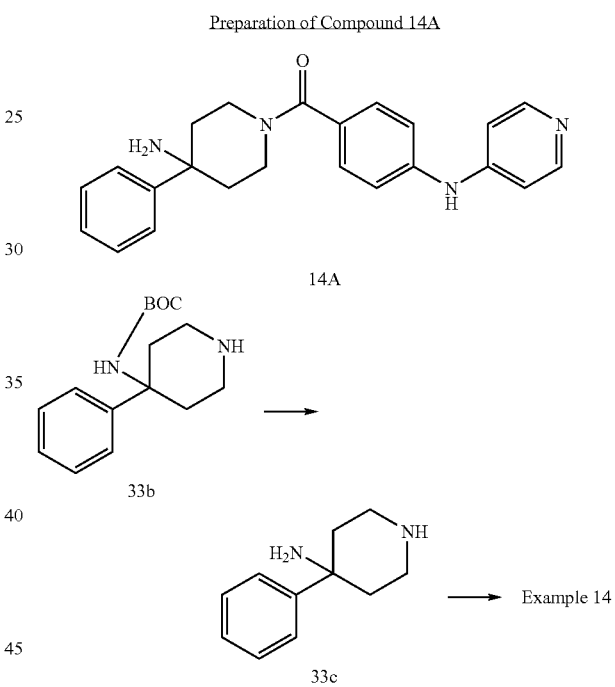

The preparation of compound 33b is described in U.S. Pat. No. 6,716,846. Compound 33c was obtained from 33b by using the procedure of Example 4, Step 2. Compound 33c was converted into the title compound through reaction with acid 23 in a procedure identical to Example 1, Step 2. MH$^+$ 373

Example 15

Preparation of Compound 15A

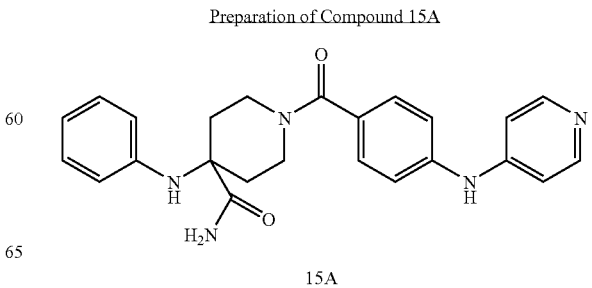

15A

Example 17

Preparation of Compound 17A

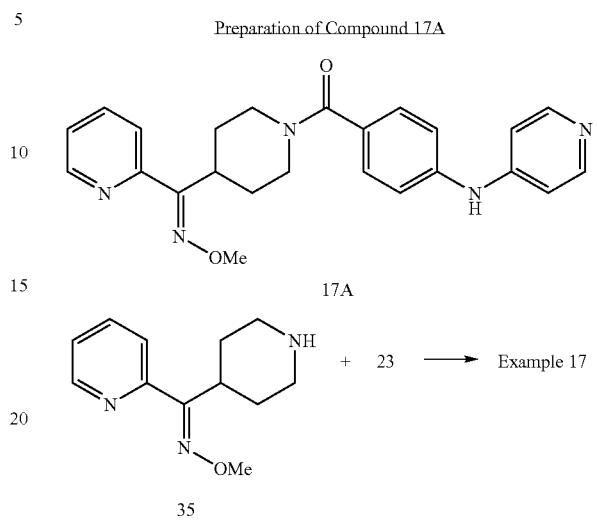

17A

Compound 35 was prepared as described in U.S. Pat. No. 6,720,328.

Compound 35 was reacted with compound 23 using the procedure of Example 1, Step 2, to obtain the title compound. MH+ 416.

Example 18

Preparation of Compound 18A

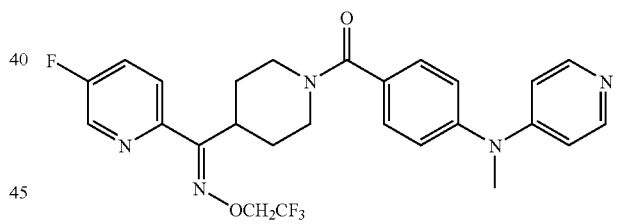

18A

Step 1:

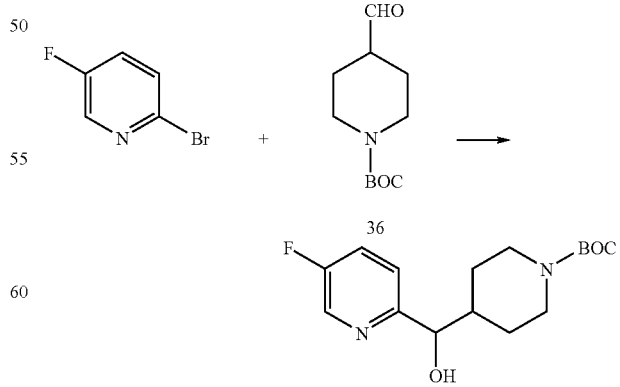

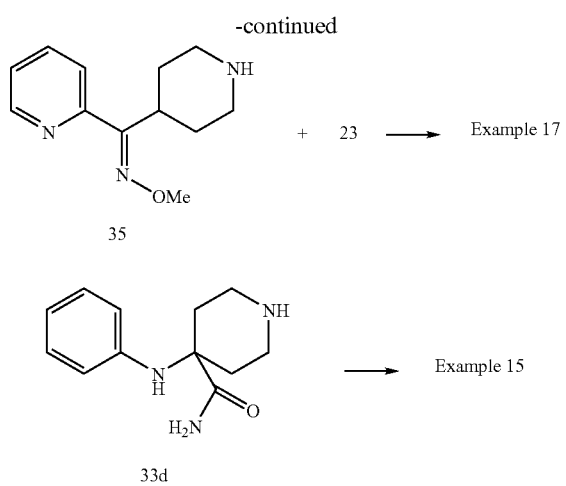

Compound 33d (purchased from Sigma-Aldrich rare chemical library) was converted into the title compound through reaction with acid 23 in a procedure identical to Example 1, Step 2. MH+ 416

Example 16

Preparation of Compound 16A

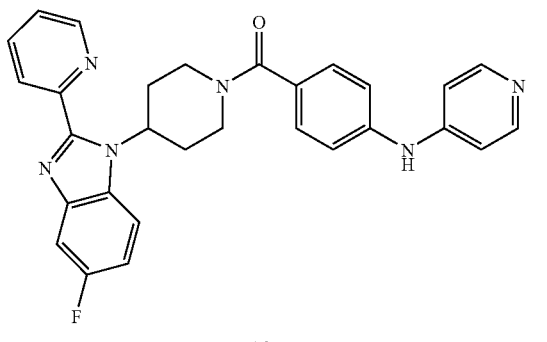

16A

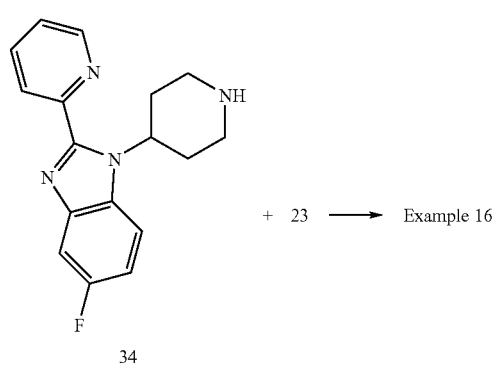

34

Compound 34 was prepared as described in US 2004/0097483.

Compound 34 was reacted with compound 23 using the procedure of Example 1, Step 2, to obtain the title compound. MH+ 493

A solution of 2-bromo-5-fluoropyridine (2.0 g, 11.4 mmol) in toluene (20 ml) was added slowly to a solution of n-BuLi (5.0 ml, 12.5 mmol) in toluene (80 ml), cooled to −78° C. and the mixture was stirred at −78° C. for 30 min. Then, a solution of aldehyde 36 (3.64 g, 17.0 mmol) in toluene (20 ml) was added and the reaction mixture was stirred at −78° C. for 2 h. It was quenched with AcOH at −78° C. and diluted with water. The product was extracted with CH₂Cl₂ and the organic layer was dried over Na₂SO₄. Purification by flash chromatography (0-1% 2N NH₃ in MeOH/CH₂Cl₂) provided 3.50 g (99%) of alcohol 37 as a yellowish oil.

Step 2:

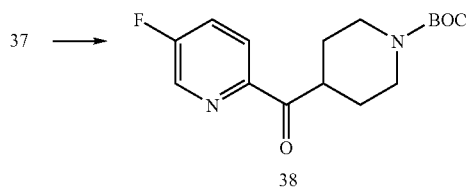

To a solution of alcohol 37 (9.0 g, 29.0 mmol) in CH₂Cl₂ (200 ml) was added saturated aqueous solution of NaHCO₃ (3.0 g, 35.6 mmol) and NaBr (0.15 g, 1.49 mmol). The mixture was cooled to 0° C. and TEMPO (0.05 g, 0.32 mmol) was added, followed by 0.7M (85 ml, 59.5 mmol) commercial bleach (NaOCl) in portions over 15 min. The reaction mixture was stirred at 0° C. for 30 min and then quenched with saturated aqueous Na₂S₂O₃ solution. The product was extracted with CH₂Cl₂ and the organic layer was dried over Na₂SO₄. Purification by flash chromatography (CH₂Cl₂) provided 6.31 g of 38 as a yellowish oil.

Step 3:

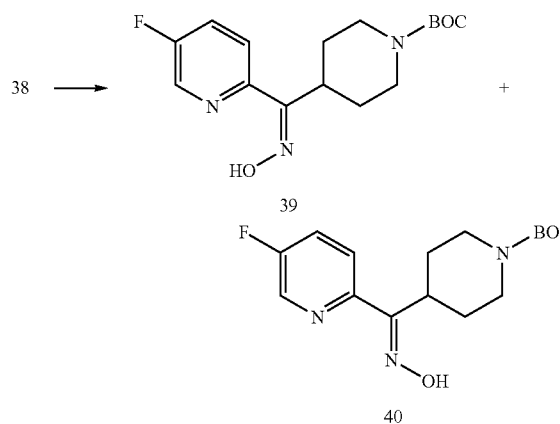

To the solution of ketone 38 (1.00 g; 3.24 mmol) in pyridine (6 ml) was added hydroxylamine hydrochloride (540 mg; 7.77 mmol). The mixture was heated at 80° C. overnight, cooled and concentrated under vacuum. The residue was flash chromatographed (1% 2.3M NH₃ in MeOH/CH₂Cl₂) to produce 385 mg of Z-oxime 39 and 553 mg of E-oxime 40.

Step 4:

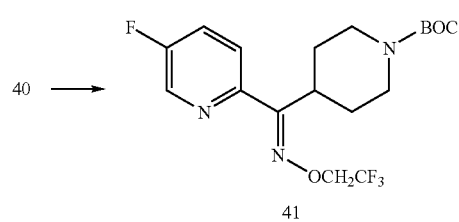

To a solution of oxime 40 (553 mg; 1.71 mmol) in a mixture of THF (16 ml) and DMF (30 ml) cooled to 0° C. was added KHMDS (1.02 g; 5.13 mmol) in portions. The reaction mixture was allowed to warm up and was stirred for 10 min at room temperature, after which 2,2,2-trifluoroethyl trifluoromethanesulfonate (1.19 g; 5.13 mmol) was added. The reaction mixture was stirred for 1 h. Water was added and the product was extracted with CH₂Cl₂. The organic phase was concentrated and the residue was flash chromatographed (2-4% EtOAc/CH₂Cl₂) to produce 438 mg of 41 as a yellow oil.

Step 5:

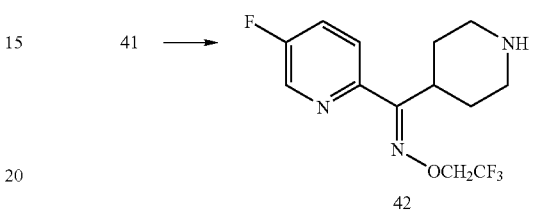

Compound 41 (438 mg; 1.08 mmol) was stirred in 20% TFA/CH₂Cl₂ for 5 h at room temperature. The mixture was concentrated under vacuum and the residue was partitioned between aqueous NaHCO₃ and CH₂Cl₂. The organic phase was separated and concentrated to produce 322 mg of free amine 42 as a yellow oil.

Step 6:

Compound 42 was reacted with compound 12 using the procedure of Example 1, Step 2, to obtain the title compound. MH⁺ 516.

Example 19

Preparation of Compound 19A

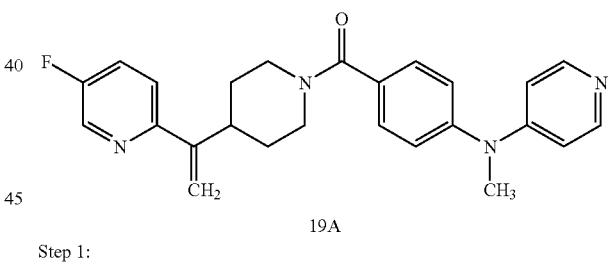

Step 1:

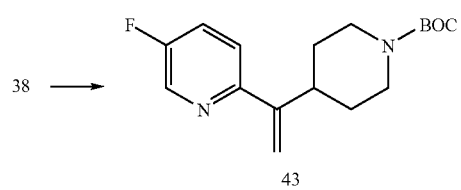

To a suspension of methyltriphenylphosphonium bromide (6.08 g, 17.0 mmol) in THF (60 ml), cooled to −78° C., was added n-BuLi (6.48 ml of 2.5M solution in hexanes; 16.2 mmol); the mixture was stirred at −78° C. for 30 min and then at 0° C. for 45 min. It was cooled back to −78° C. and a solution of ketone 38 (2.50 g, 8.1 mmol) in THF (20 ml) was added. The reaction mixture was stirred at −78° C. for 30 min and warmed up to room temperature. It was quenched with water, and the product was extracted with CH₂Cl₂. The organic layer was dried over Na₂SO₄ and purified by flash chromatography (1:9:10 EtOAc/hexanes/CH₂Cl₂) to provide 1.45 g of 43 as a yellow oil.

Step 2:

Compound 43 was converted into the title compound using procedures of Example 18, Step 5, followed by Example 1, Step 2. MH+ 417

Example 20

Preparation of Compound 20A

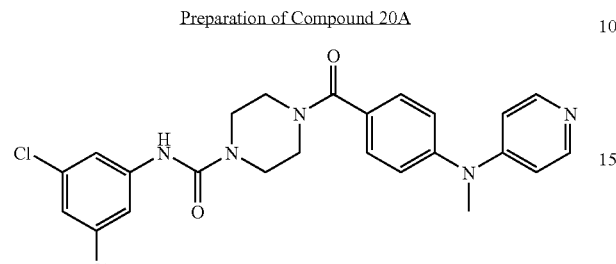

20A

Step 1:

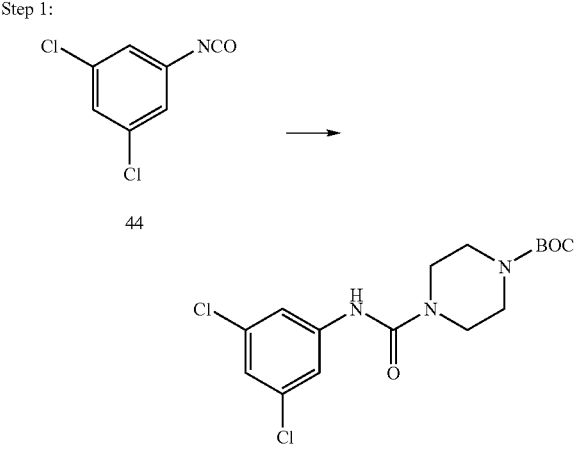

A solution of isocyanate 44 (5.60 g, 29.8 mmol), N—BOC-piperazine (5.60 g, 30.1 mmol) and Et₃N (4.2 ml, 30.1 mmol) in CH₂Cl₂ (200 ml) was stirred at room temperature for 1 h before treatment with 1N aqueous NaOH. The organic layer was washed with brine and dried over anhydrous MgSO₄. The drying agent was filtered and the filtrate was stripped of solvent under vacuum to obtain 11.0 g of compound 45, which was used directly without purification.

Step 2:

Compound 45 was converted into the title compound using procedures of Example 18, Step 5, followed by Example 1. Step 2. MH+ 484

Example 21

Preparation of Compound 21A

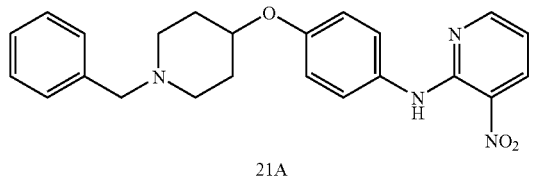

21A

Step 1:

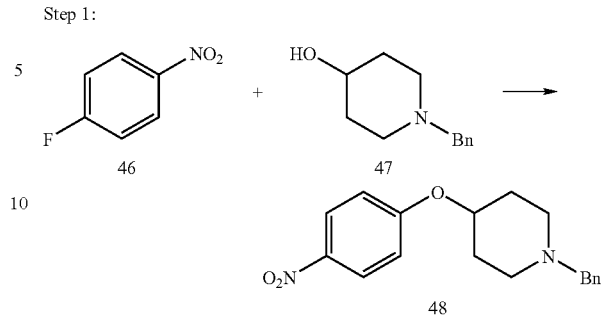

To a stirred suspension of compound 47 (20.1 g, 0.100 mol) in tert-butanol (120 ml) was added, portionwise, potassium tert-butoxide (9.5 g, 0.084 mol). The mixture was heated under reflux for 30 min, yielding a homogeneous solution which was cooled to 35° C., and to which was added compound 46 (12.7 g, 0.09 mol) in a single portion. An exothermic reaction raised the internal temperature to 68° C. When the exotherm had subsided, the mixture was heated to reflux for 30 min. Solvent was removed under vacuum, and the residue was treated with ice water, which resulted in formation of an insoluble fraction. Crude product 48 was isolated by filtration of the insoluble solid. Crude 48 (21 g, 0.0672 mol) was treated with a mixture of 2N HCl and EtOAc, and the resultant mixture was stirred at room temperature for 10 min. The insoluble material was filtered and washed thoroughly with water and EtOAc to obtain 18.1 g of the hydrochloride salt of compound 48, mp 287-289° C. The HCl salt was stirred in a mixture of 1N NaOH (150 ml) and CH₂Cl₂ (250 ml) until all solids dissolved. The organic phase was separated, washed with water and dried (anhydrous MgSO₄). The drying agent was filtered, and the filtrate was stripped of solvent under vacuum to obtain 15.7 g of the free base form of compound 48 as a beige solid.

Step 2:

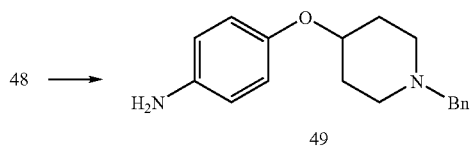

A solution of 9.0 g (28.8 mmol) of compound 48 in warm DMF (40 ml) was diluted with EtOH (120 ml). The solution was cooled to room temperature, and to it was added half a teaspoon of Raney nickel paste (50% water). The resultant mixture was hydrogenated at 35 psi until hydrogen uptake leveled off. The spent catalyst was filtered through a pad of celite, and the filtrate was concentrated under vacuum. The residue was partitioned between water and Et₂O-EtOAc (1:1). The organic extract was washed with water, dried over anhydrous MgSO₄ and filtered. The filtrate was concentrated under vacuum to obtain 7.8 g of compound 49 as syrup, which was sufficiently pure for use in next step.

Step 3:

A stirred mixture of compound 49 (3.5 g, 12.4 mmol), anhydrous K₂CO₃ (1.87 g, 13.5 mmol) and 2-chloro-3-nitropyridine (1.97 g, 12.4 mmol) in anhydrous toluene (50 ml) was heated under reflux for 18 h. TLC revealed a mixture of starting material and product. Therefore, additional quantities of 2-chloro-3-nitropyridine (0.5 g) and anhydrous K₂CO₃ (0.5 g) were introduced, and heating under reflux was continued for another 18 h. After cooling to room temperature, the mixture was treated with ice-water and extracted with toluene. Combined toluene extracts were washed successively with 0.5N aqueous NaOH and water and were then treated with 0.5N HCl (200 ml). The red precipitate which formed was filtered to obtain 3.3 g of the crude HCl salt of the title compound. The acidic aqueous phase was separated, washed with EtOAc and basified with 10% aqueous NaOH. The resultant red precipitate was filtered and washed with water to provide 1.3 g of the free base form of the title compound. A mixture of HCl salt (3.2 g) and free base (1.3 g) was partitioned between 0.5N NaOH and CH₂Cl₂. The organic phase was washed with water and dried (anhydrous MgSO₄). The drying agent was filtered, and the filtrate was concentrated under vacuum to obtain 4.5 g of the free base form of the title compound. MH⁺ 405

Example 22

Preparation of Compound 22A

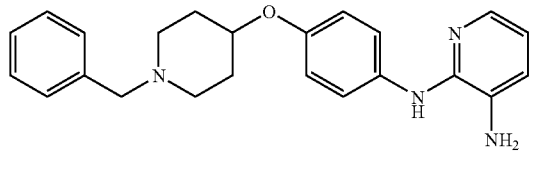

22A

A solution of 2.2 g (5.5 mmol) of Example 21 in warm DMF (30 ml) was diluted with EtOH (60 ml). The solution was cooled to room temperature, and to it was added half a teaspoon of Raney nickel paste (50% water). The resultant mixture was hydrogenated at 44 psi until hydrogen uptake leveled off. The spent catalyst was filtered through a pad of celite, and the filtrate was concentrated under vacuum. The residual oil was partitioned between water and EtOAc. The organic extract was washed with water, dried over anhydrous MgSO₄ and filtered. The filtrate was concentrated under vacuum to produce a solid that was triturated with hexane. Filtration yielded 1.58 g of title compound. MH⁺ 375

Example 23

Preparation of Compound 23A

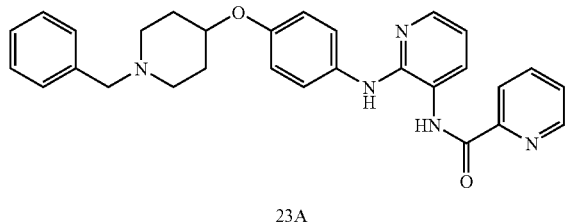

23A

To a stirred, ice-cooled solution of Example 22 (0.73 g, 1.95 mmol) and Et₃N (2.0 ml) in dry CH₂Cl₂ (30 ml) was added picolinoyl chloride hydrochloride (0.38 g, 2.15 mmol) in a few portions. Stirring at ~5° C. was maintained for 5 min, then continued at room temperature for 18 h. The reaction mixture was treated with ice water and the organic phase was separated and washed with water, dried over anhydrous MgSO₄, filtered and concentrated to a viscous residue, which contained significant unchanged starting material according to TLC. Therefore, this residue (0.85 g) was dissolved in dry CH₂Cl₂ (30 ml), and to this solution were added picolinoyl chloride hydrochloride (0.38 g, 2.15 mmol) and Et₃N (1 ml). The reaction solution was stirred at room temperature for 18 h. The reaction mixture was treated with water, and the organic phase was separated and washed with water, dried over anhydrous MgSO₄, filtered and concentrated to a viscous residue, which was purified by flash column chromatography on silica gel, eluting with CH₂Cl₂-MeOH (95:5) to obtain the title compound as a glass (810 mg). MH⁺ 480

Example 24

Preparation of Compound 24A

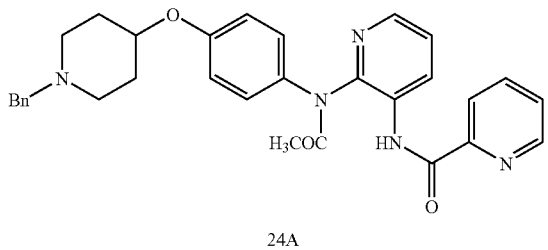

24A

A solution of Example 23 (260 mg, 0.54 mmol) in glacial AcOH (10 ml) was heated under reflux for 18 h, then was concentrated under vacuum to a viscous residue, which was partitioned between water and Et₂O-EtOAc (3:1). The aqueous phase was made basic with dilute aqueous NH₄OH and was extracted with EtOAc. Combined organic extracts were washed with water, dried (anhydrous MgSO₄) and filtered. The filtrate was concentrated in vacuo to obtain a viscous residue which was purified by flash column chromatography on silica gel, eluting with EtOAc-MeOH (95:5) to obtain the free base form of title compound as a glass (0.091 g).

To a solution of free base (91 mg, 0.174 mmol) in EtOAc was added a solution of maleic acid (20 mg; 0.172 mmol) in EtOAc. The resultant mixture was concentrated in vacuo to a small volume, diluted with Et₂O and allowed to stand at room temperature. Filtration of the resultant precipitate yielded 70 mg of the maleic acid salt of title compound as a beige solid. MH⁺ 522

Example 25

Preparation of Compound 25A

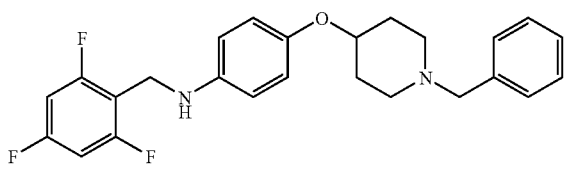

25A

To a stirred solution of compound 49 (0.720 g, 2.55 mmol) and 2,4,6-trifluorobenzaldehyde (0.407 g, 2.55 mmol) in anhydrous CH₂Cl₂ (15 ml) was added portionwise NaBH(Oac)₃ (1.62 g, 7.7 mmol). The reaction mixture was stirred at room temperature for 18 h and was then treated with water. The organic phase was separated and concentrated under vacuum to a viscous residue, which was partitioned between Et₂O and 1N aqueous NaOH. The organic extracts were washed with brine, dried (anhydrous MgSO₄) and filtered. The filtrate was concentrated in vacuo to obtain a viscous residue which was flash chromatographed on silica gel. Elution with CH₂Cl₂:EtOAc (1:1) yielded 0.72 g of the free base form of the title compound as a syrup.

To a solution of free base (630 mg, 1.48 mmol) in EtOAc was added a solution of maleic acid (172 mg; 1.48 mmol) in EtOAc. As the resultant mixture was cooled in an ice-water bath, a precipitate began to form. Filtration yielded 786 mg of the maleic acid salt of title compound as a white crystalline solid. MH⁺ 427

Example 26

Preparation of Compound 26A

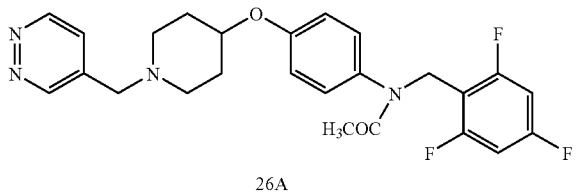

26A

Step 1:

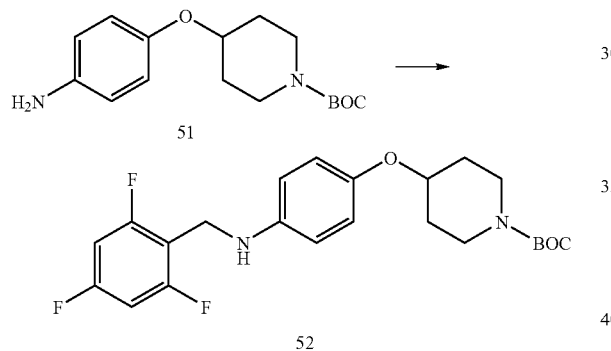

To a stirred solution of compound 51 (4.65 g, 15.9 mmol) and 2,4,6-trifluorobenzaldehyde (2.55 g, 15.9 mmol) in anhydrous CH₂Cl₂ (70 ml) was added portionwise over 2 min NaBH(OAc)₃ (10 g, 48 mmol). The reaction mixture was stirred at room temperature for 18 h and was then treated with water. The organic phase was separated and concentrated under vacuum to a syrup, which was flash chromatographed on silica gel. Elution with CH₂Cl₂:MeOH (99:1) yielded 5.55 g of compound 52 as a syrup.

Step 2:

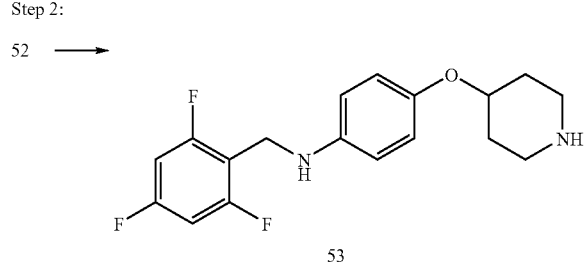

To a stirred solution of compound 52 (5.5 g, 12.6 mmol) in CH₂Cl₂ (6 ml) was added dropwise TFA (10 ml). The resultant solution was stirred at room temperature for 48 h. The reaction mixture was concentrated under vacuum. The viscous residue was partitioned between aqueous NaOH and CH₂Cl₂. Combined extracts were washed with brine and dried over anhydrous MgSO₄. The drying agent was filtered, and the filtrate was stripped of solvent under vacuum. The solid residue was triturated with hexanes to obtain 3.7 g of compound 53 as a solid.

Step 3:

To a stirred solution of compound 53 (0.200 g, 0.596 mmol) and pyridazine-4-carbaldehyde (see U.S. Pat. No. 6,720,328) (0.074 g; 0.68 mmol) in anhydrous CH₂Cl₂ (50 ml) was added NaBH(OAc)₃ (0.433 g, 2.0 mmol). The reaction mixture was stirred at room temperature for 18 h and was then concentrated in vacuo. The viscous residue was partitioned between water and EtOAc. The organic extract was washed with water, dried (anhydrous MgSO₄) and filtered. The filtrate was concentrated in vacuo to obtain the free base form of the title compound as a syrup which exhibited a single spot on TLC.

A portion (150 mg, 0.318 mmol) of free base was dissolved in EtOAc and the resultant solution mixed with a solution of maleic acid (40 mg; 0.345 mmol). Upon standing at room temperature, a precipitate began to form. The mixture was then cooled in an ice-water bath and filtered to obtain 59 mg of the maleic acid salt of title compound. MH⁺ 471

Example 27

Preparation of Compound 27A

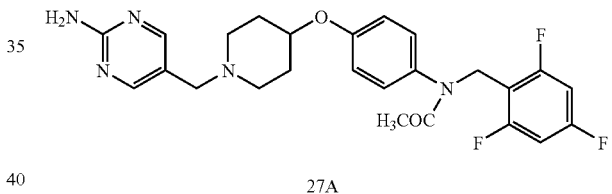

27A

The title compound was prepared using the procedure described in Example 26, except that in the last step, 2-aminopyrimidine-5-carbaldehyde (see U.S. Pat. No. 6,720,328) was used in place of pyridazine-4-carbaldehyde. MH⁺ 486

Example 28

Preparation of Compound 28A

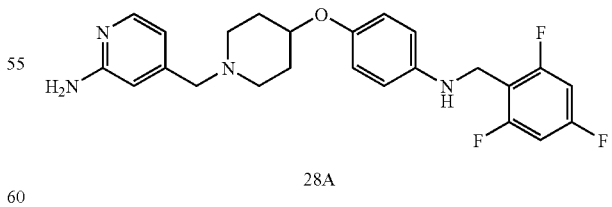

28A

To a stirred solution of compound 53 (200 mg, 0.596 mmol) and N—BOC-2-aminopyridine-4-carbaldehyde (see U.S. Pat. No. 6,720,328) (152 mg, 0.68 mmol) in anhydrous CH₂Cl₂ (50 ml) was added NaBH(OAc)₃ (433 mg, 2.0 mmol). The reaction mixture was stirred at room temperature for 48 h and was then treated with water. The organic phase was separated and concentrated to a solid residue, which was dissolved in EtOAc-Et$_2$O (1:1) and extracted with 2% aqueous maleic acid solution. Combined aqueous extracts were basified to pH 8 with 1N aqueous NaOH and extracted with EtOAc. The organic extracts were washed with brine, dried (anhydrous MgSO$_4$) and filtered. The filtrate was concentrated in vacuo to obtain a glass which was flash chromatographed on silica gel. Elution with CH$_2$Cl$_2$-7N methanolic ammonia (98:2) yielded 0.18 g of the title compound as a solid. MH$^+$ 443

Using the procedures, described above, compounds 29A-60A were prepared:

| Compound | Structure | MS (M + H) |
|---|---|---|
| 29A | 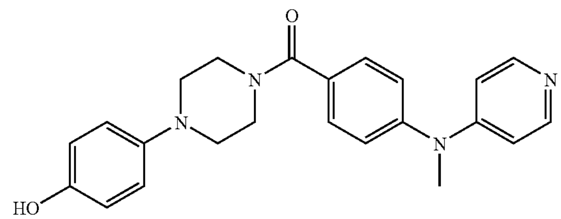 | 389 |
| 30A | 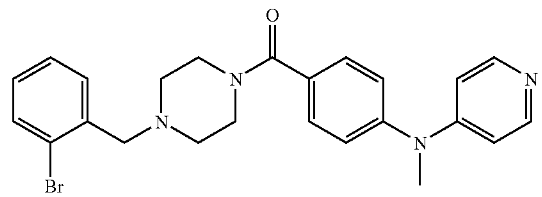 | 465 |
| 31A | 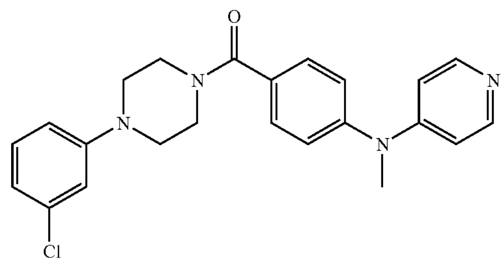 | 407 |
| 32A | 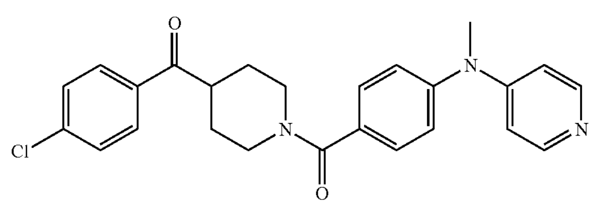 | 434 |
| 33A | 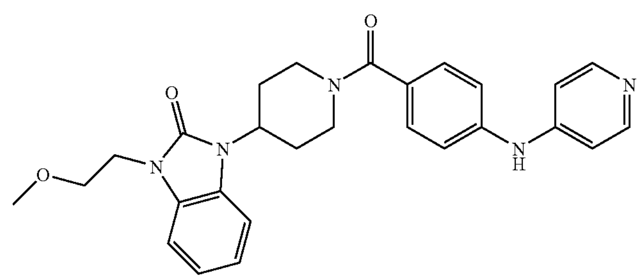 | 472 |
| 34A | 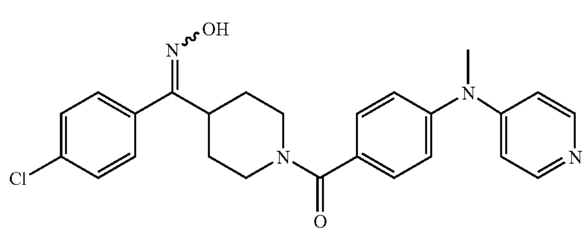 | 449 |

-continued

| Compound | Structure | MS (M + H) |
|---|---|---|
| 35A | 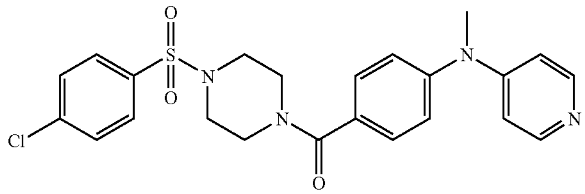 | 471 |
| 36A | 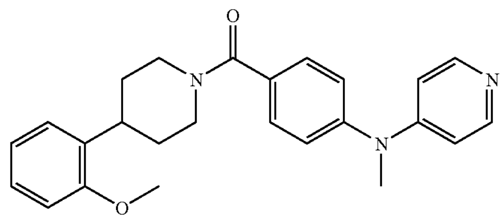 | 402 |
| 37A | 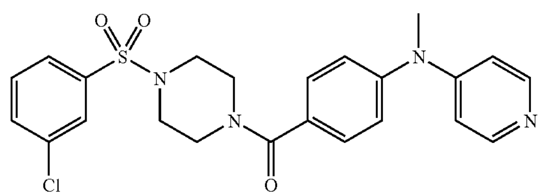 | 471 |
| 38A | 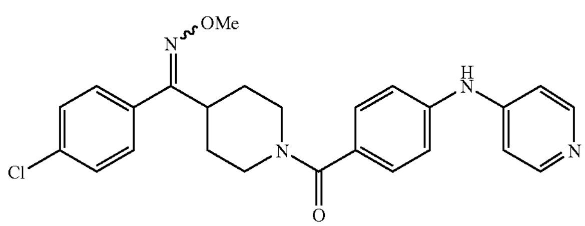 | 449 |
| 39A | 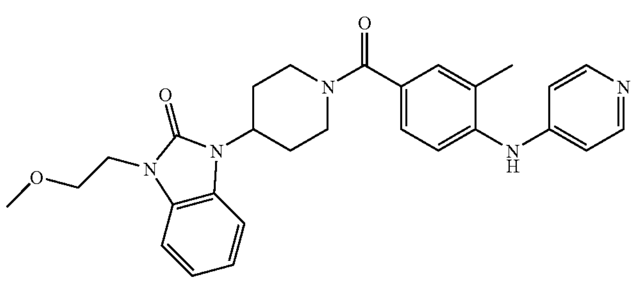 | 486 |
| 40A | 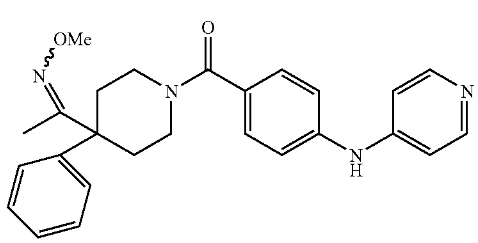 | 429 |

-continued

| Compound | Structure | MS (M + H) |
|---|---|---|
| 41A | 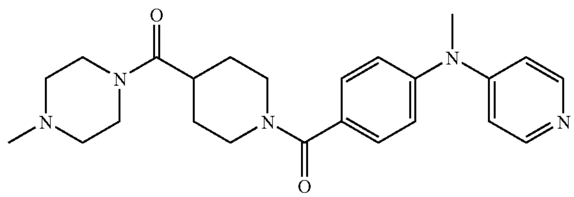 | 422 |
| 42A | 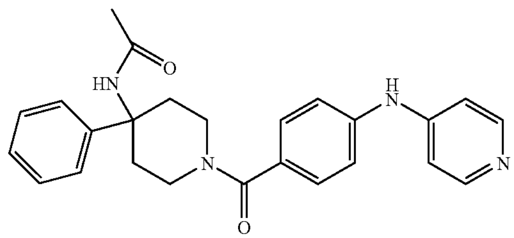 | 415 |
| 43A | 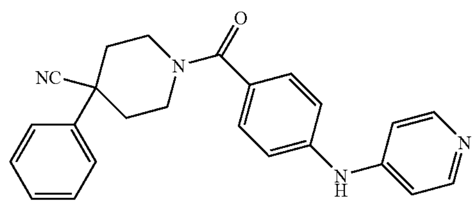 | 383 |
| 44A | 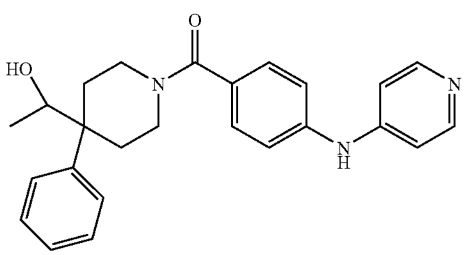 | 402 |
| 45A | 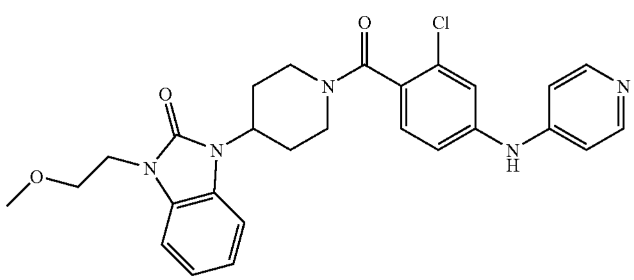 | 506 |
| 46A | 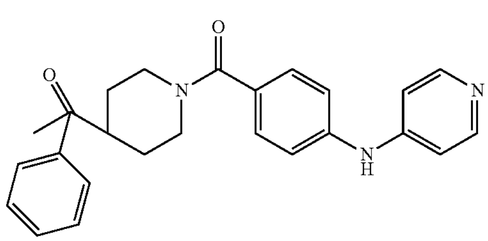 | 400 |

-continued

| Compound | Structure | MS (M + H) |
|---|---|---|
| 47A | 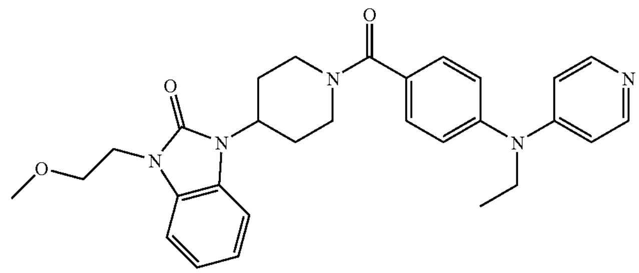 | 500 |
| 48A | 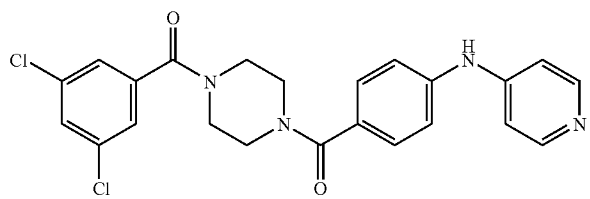 | 455 |
| 49A | 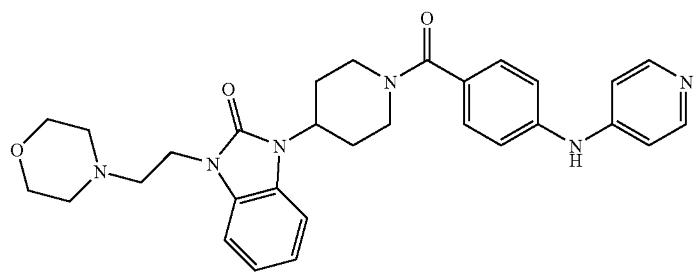 | 527 |
| 50A | 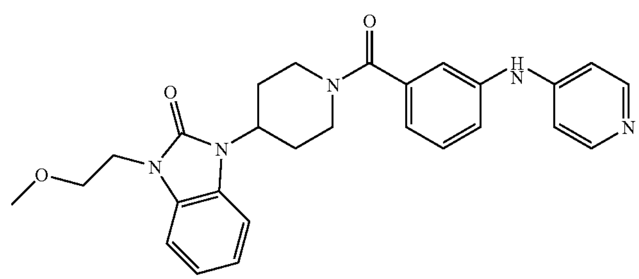 | 472 |
| 51A | 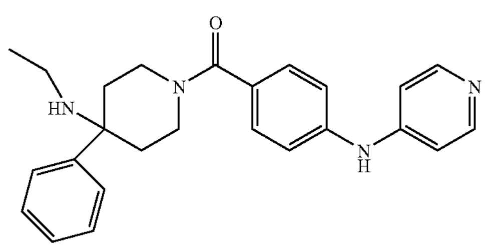 | 401 |
| 52A | 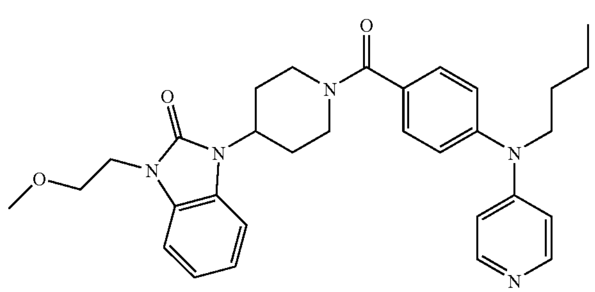 | 528 |

-continued

| Compound | Structure | MS (M + H) |
|---|---|---|
| 53A | 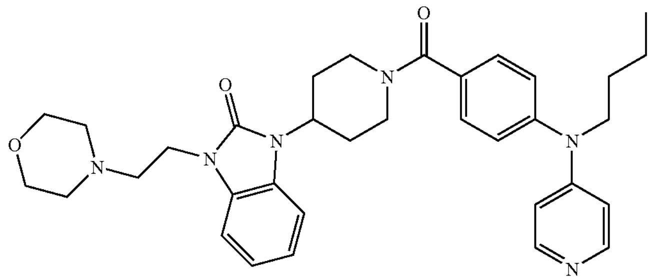 | 583 |
| 54A | 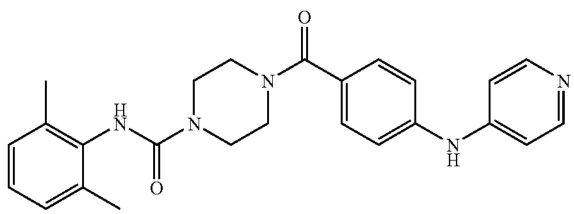 | 430 |
| 55A | 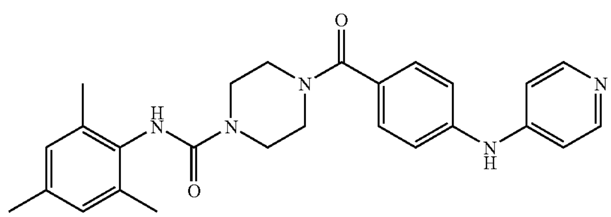 | 444 |
| 56A | 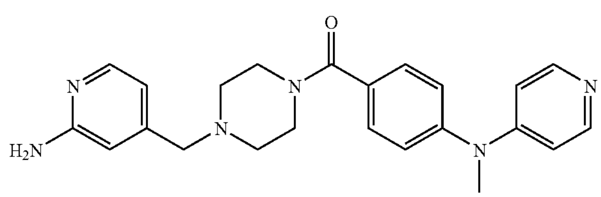 | 403 |
| 57A | 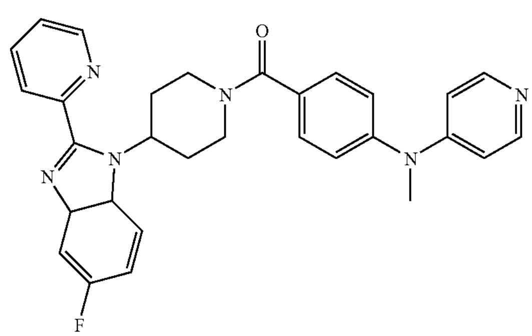 | 507 |

-continued
| Compound | Structure | MS (M + H) |
|---|---|---|
| 58A | 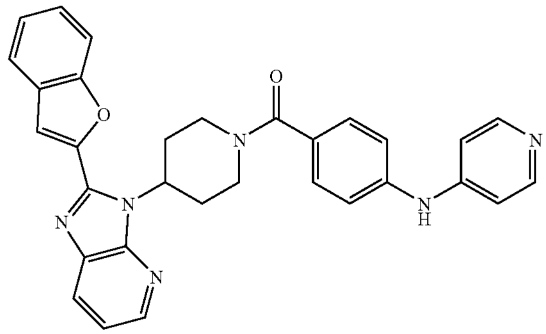 | 515 |
| 59A | 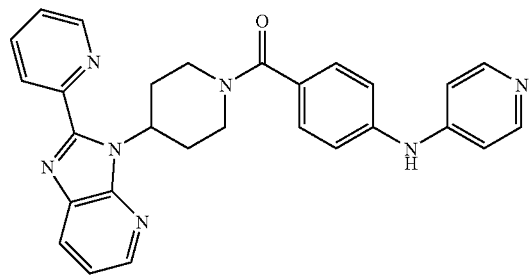 | 476 |
| 60A | 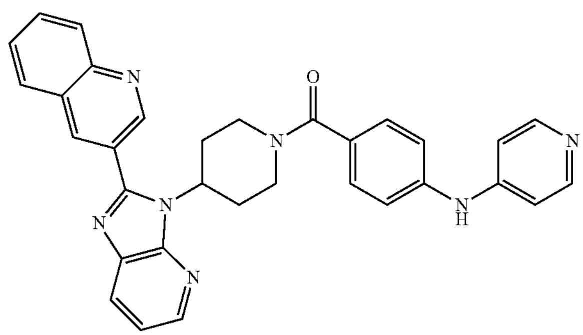 | 526 |
Example 29
Preparation of Compound 61A-158A
General Procedure:
Step 1:
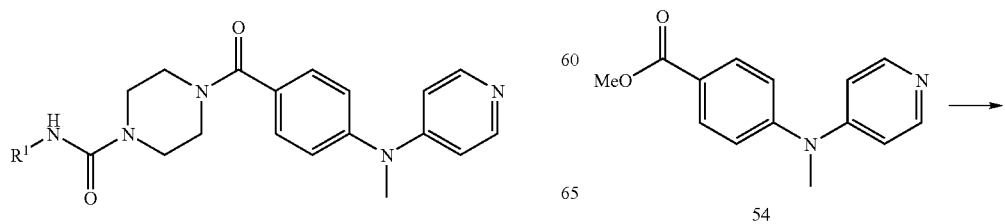

-continued

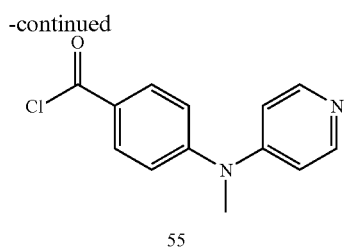

55

To a MeOH solution (20 ml) of ester 54 (1.6 g, 6.512 mmol) at 25° C. was added a 1M aqueous LiOH solution (7.16 mmol, 1.1 equiv). After stirring at 25° C. for 1 day, additional 1M aqueous LiOH solution (7.16 mmol, 1.1 equiv) was added and let stir overnight. The solvent was then removed in vacuo and the resultant solid dried under vacuum for 2 days.

The resultant solid was then suspended in $CH_2Cl_2$ (70 ml) and oxalyl chloride (25.05 mmol, 4 equiv) was added at 25° C. under $N_2$. After stirring overnight, additional oxalyl chloride (25.05 mmol, 4 equiv) was added and let stir for several days. DMF was added (1 drop) and the mixture was stirred at 25° C. for 2 days, then the solvent was removed in vacuo. Additional $CH_2Cl_2$ (50 ml) was added and the solvent was removed in vacuo. This was repeated two additional times to obtain 55.

Step 2:

55 ⟶

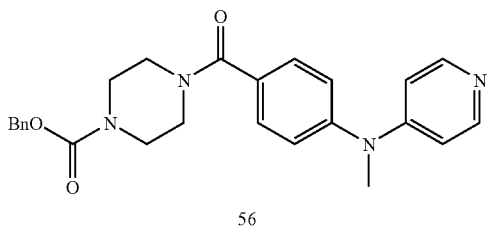

56

To a $CH_2Cl_2$ solution (50 ml) of 55 (6.512 mmol) was added $Et_3N$ (1.8 ml, 2 equiv) then CBZ-piperazine (7.16 mmol, 1.1 equiv) at 25° C. under $N_2$. The solution was stirred at 25° C. for 4 days, then 1N aqueous NaOH was added (50 ml), the products extracted with $CH_2Cl_2$, dried over $Na_2SO_4$, filtered, and dried in vacuo. The products were then purified by FLC ($CH_2Cl_2$-MeOH—$NH_4OH$ 97:3:0.5 to 92:8:0.5) to provide 56 contaminated with CBZ-piperazine. CBZ-piperazine was removed from 56 by dissolving the mixture in $CH_2Cl_2$ (100 ml) and then adding PS-Isocyanate resin (1.2 g). The mixture was stirred at 25° C. for 1 h then an additional 1.5 g of PS-Isocyanate resin added. After an additional 3 h, the products were filtered from the resin, washing with $CH_2Cl_2$, and the solvent was removed in vacuo to give 56 (1.51 g, 54% yield) as a yellow-white foam.

Step 3:

56 ⟶

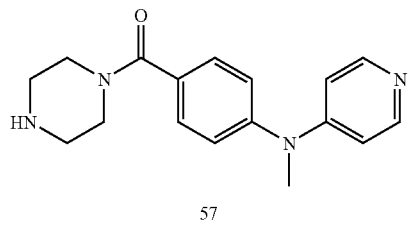

57

$H_2$ was bubbled into a MeOH suspension of 10% Pd on carbon (120.3 mg), 56 (1.19 g, 2.77 mmol) and conc. HCl (1.2 ml, 5 equiv) for 20 min at 25° C., then the mixture was stirred for 4 h under an $H_2$ atmosphere. After $N_2$ was bubbled through the solution for 20 min, the mixture was filtered through a Celite pad, eluting with MeOH, and the solvent was removed in vacuo. The products were partitioned between $CH_2Cl_2$ and 1N NaOH, the layers separated, and the aqueous layer back-extracted with $CH_2Cl_2$ (3×). The $CH_2Cl_2$ layers were then combined, dried over $Na_2SO_4$, filtered, and dried in vacuo. The products were then purified by FLC ($CH_2Cl_2$-MeOH—$NH_4OH$ 94:6:0.5 to 92:8:0.5) to provide 57 (834 mg, 100% yield).

Step 4:

A stock solution of 57 (1 ml, 0.0268 mmol) in $CH_2Cl_2$ was added to 104-fritted tubes in Bohdan Miniblocks. To each tube was added 1M stock solutions of the individual isocyanates ($R^1NCO$) in toluene (0.0.5 mmol, 2 equiv). The Miniblocks were sealed and shaken at 25° C. for 4 h. To each tube was added an additional 2 equiv. of the individual isocyanate and the Miniblocks were sealed and shaken at 25° C. for 4 h. A DCE solution of acetic anhydride (0.54 mmol, 20 equiv) was added to each tube and the blocks were shaken at 25° C. for 16 h. Amberlyst-15 resin (~0.10 g) was added to each tube and the Miniblocks were shaken at 25° C. for 2 h. The tubes were drained and the resin was washed three times each with $CH_2Cl_2$, then MeOH, shaking for 5 min each time, to remove unreacted reagents. Ammonia in MeOH (2N, 2 ml) was then added to each tube and the Miniblocks were shaken at 25° C. for 20 min. The MeOH filtrates were collected and the resin was again shaken with ammonia in MeOH (2N, 2 ml) at 25° C. for 20 min. The combined filtrates from each tube were then evaporated to dryness on a SpeedVac concentrator overnight. The resulting samples were evaluated by LCMS and were at least 70% pure.

Using the procedure described above, compounds 61A-158A were prepared:

| Compound | Structure | MS (M + H) |
|---|---|---|
| 61A | 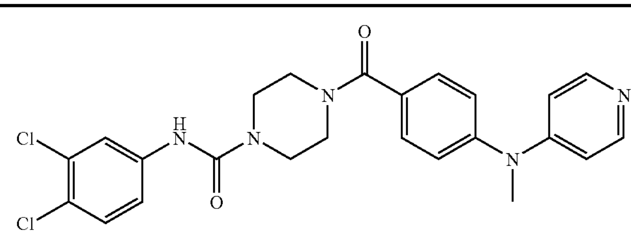 | 484 |

-continued

| Compound | Structure | MS (M + H) |
|---|---|---|
| 62A | 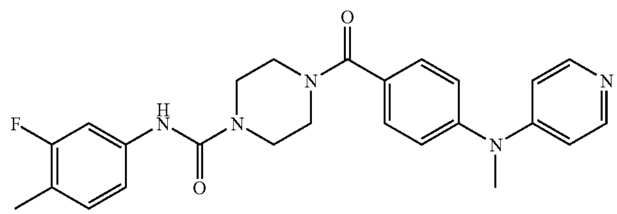 | 448 |
| 63A | 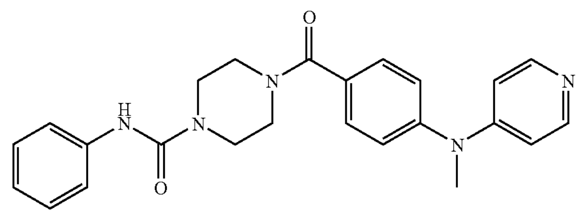 | 416 |
| 64A | 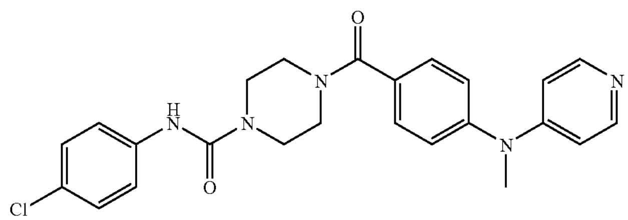 | 450 |
| 65A | 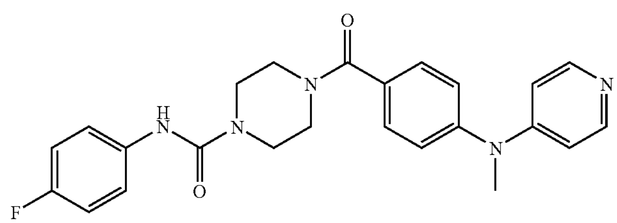 | 434 |
| 66A | 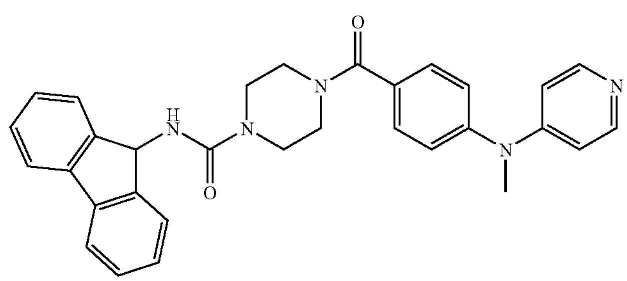 | 504 |
| 67A | 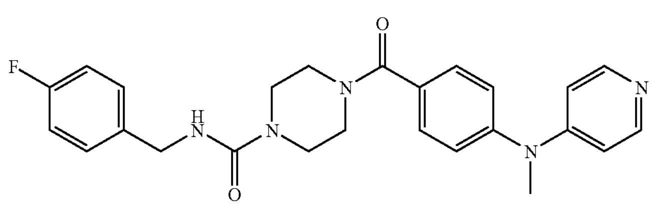 | 448 |
| 68A | 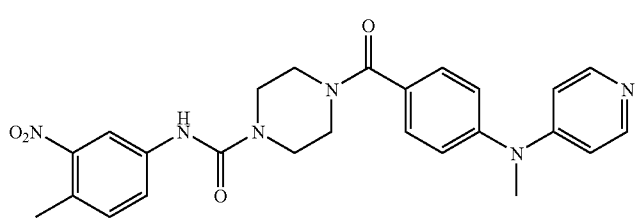 | 475 |

-continued

| Compound | Structure | MS (M + H) |
|---|---|---|
| 69A | ![structure] 3-CF3, 4-F phenyl urea piperazine benzoyl 4-(N-methyl-N-(pyridin-4-yl)amino)phenyl | 502 |
| 70A | (S)-1-phenylethyl urea piperazine benzoyl 4-(N-methyl-N-(pyridin-4-yl)amino)phenyl | 444 |
| 71A | 4-CF3 phenyl urea piperazine benzoyl 4-(N-methyl-N-(pyridin-4-yl)amino)phenyl | 484 |
| 72A | 2,3-dimethylphenyl urea piperazine benzoyl 4-(N-methyl-N-(pyridin-4-yl)amino)phenyl | 444 |
| 73A | 4-(methylthio)phenyl urea piperazine benzoyl 4-(N-methyl-N-(pyridin-4-yl)amino)phenyl | 462 |
| 74A | 3-cyanophenyl urea piperazine benzoyl 4-(N-methyl-N-(pyridin-4-yl)amino)phenyl | 441 |
| 75A | 2-CF3, 4-Cl phenyl urea piperazine benzoyl 4-(N-methyl-N-(pyridin-4-yl)amino)phenyl | 518 |

-continued

| Compound | Structure | MS (M + H) |
|---|---|---|
| 76A | 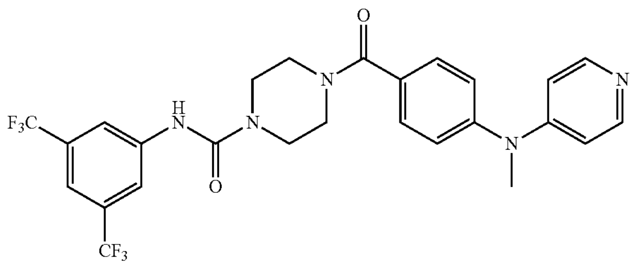 | 552 |
| 77A | 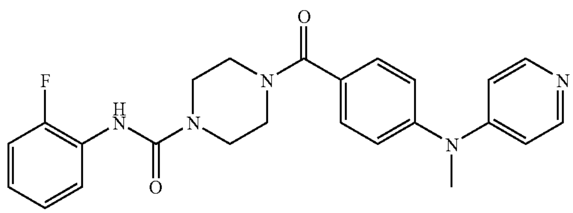 | 434 |
| 78A | 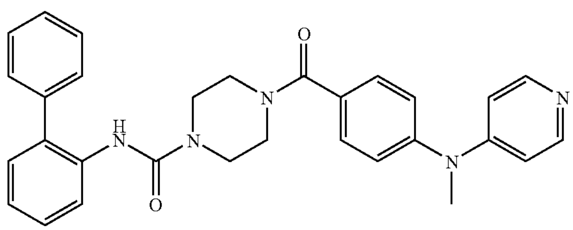 | 492 |
| 79A | 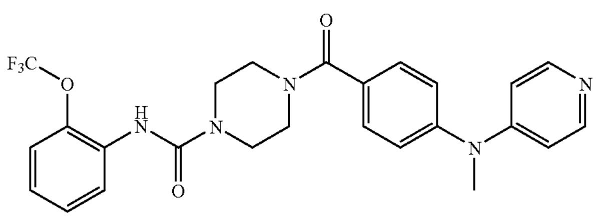 | 500 |
| 80A | 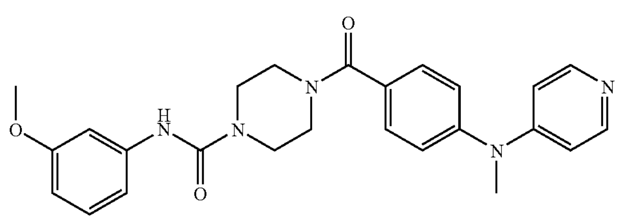 | 446 |
| 81A | 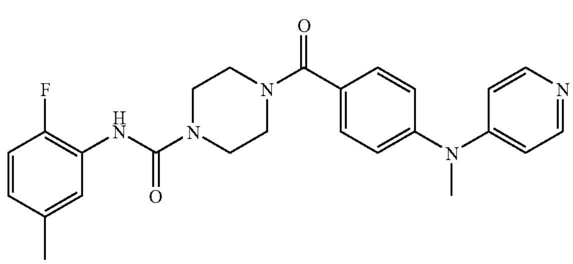 | 448 |

-continued

| Compound | Structure | MS (M + H) |
|---|---|---|
| 82A | 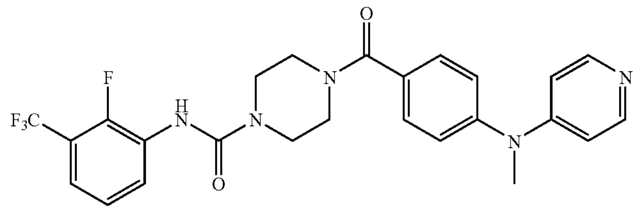 | 502 |
| 83A | 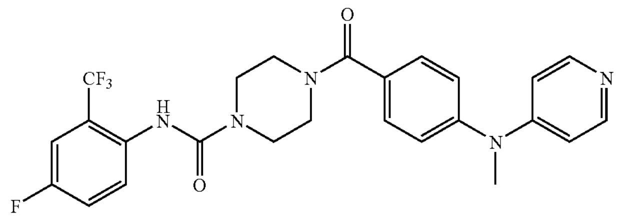 | 502 |
| 84A | 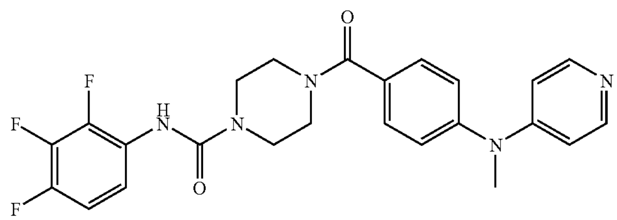 | 470 |
| 85A | 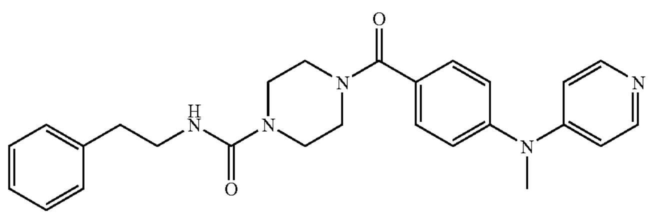 | 444 |
| 86A | 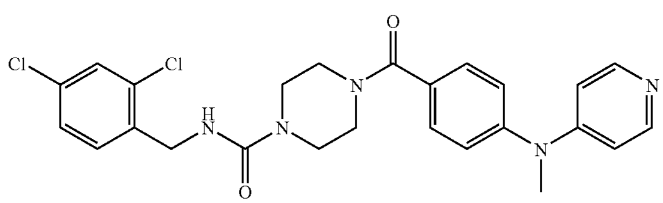 | 498 |
| 87A | 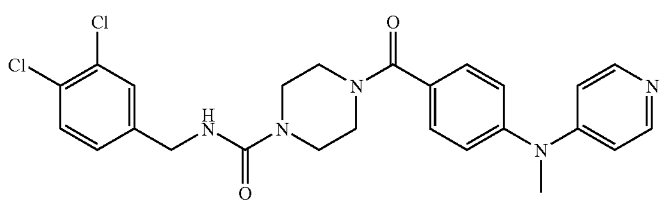 | 498 |
| 88A | 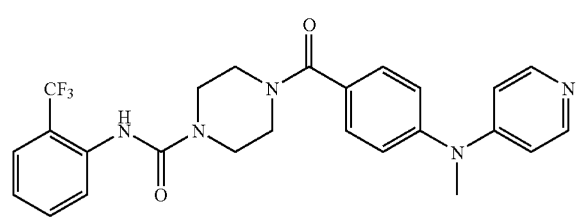 | 484 |

-continued

| Compound | Structure | MS (M + H) |
|---|---|---|
| 89A | 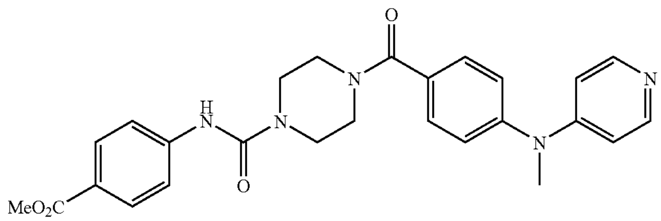 | 474 |
| 90A | 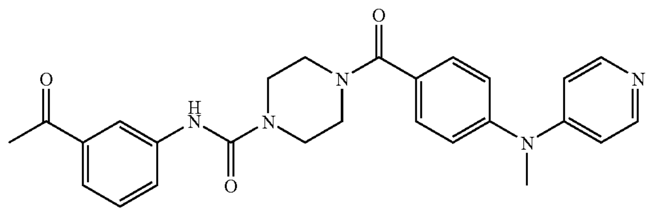 | 458 |
| 91A | 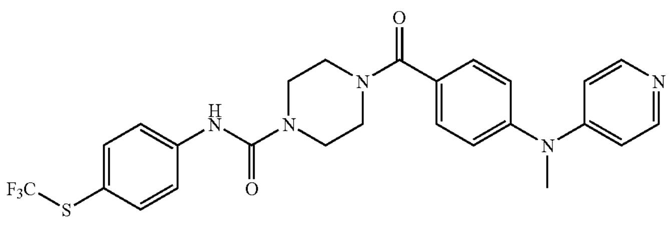 | 516 |
| 92A | 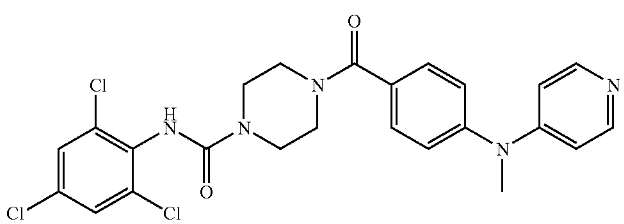 | 518 |
| 93A | 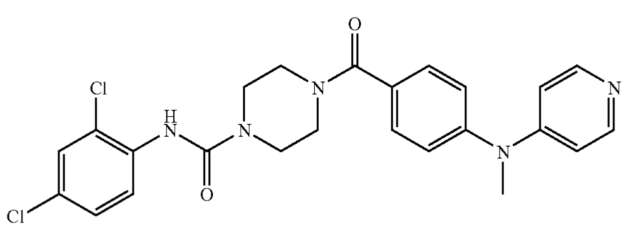 | 484 |
| 94A | 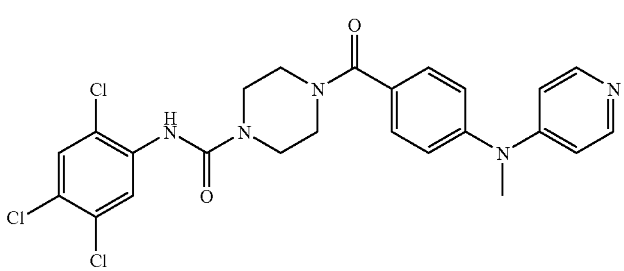 | 518 |

-continued

| Compound | Structure | MS (M + H) |
|---|---|---|
| 95A | 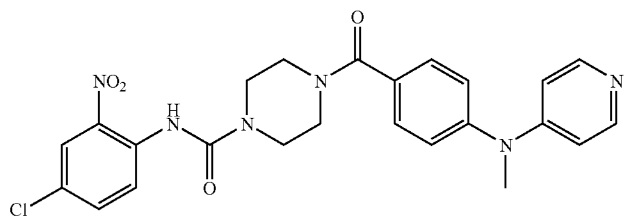 | 495 |
| 96A | 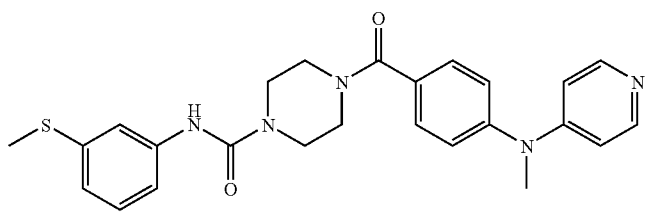 | 462 |
| 97A | 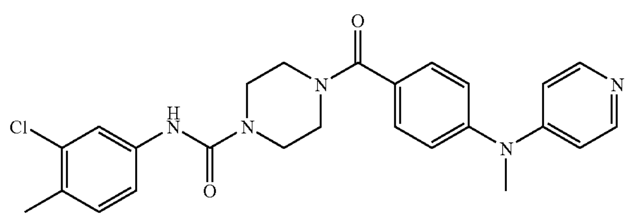 | 464 |
| 98A | 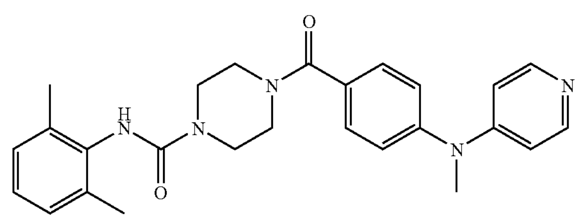 | 444 |
| 99A | 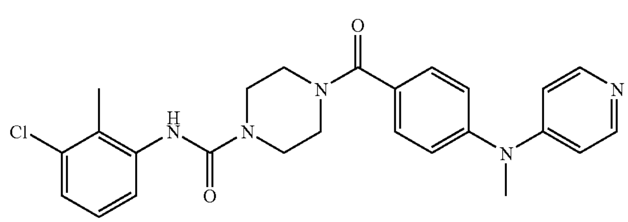 | 450 |
| 100A | 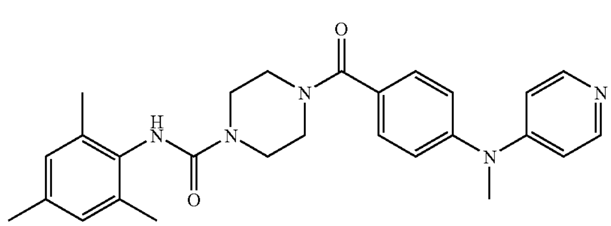 | 458 |

-continued
| Compound | Structure | MS (M + H) |
|---|---|---|
| 101A | 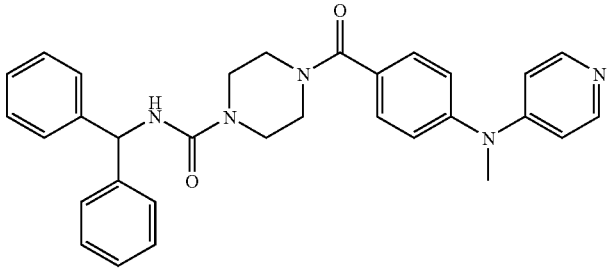 | 506 |
| 102A | 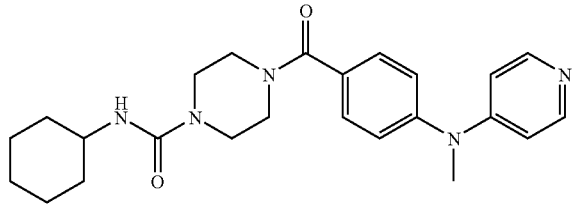 | 422 |
| 103A | 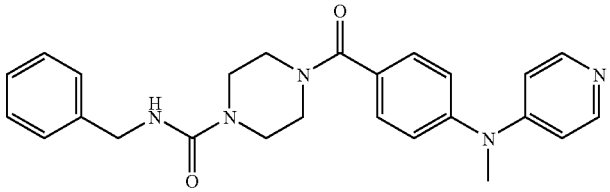 | 430 |
| 104A | 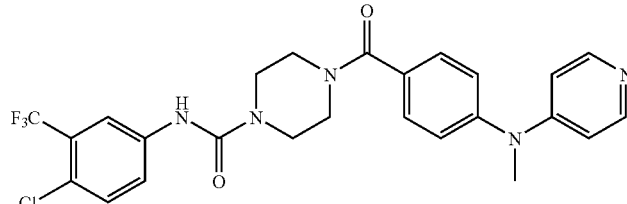 | 518 |
| 105A | 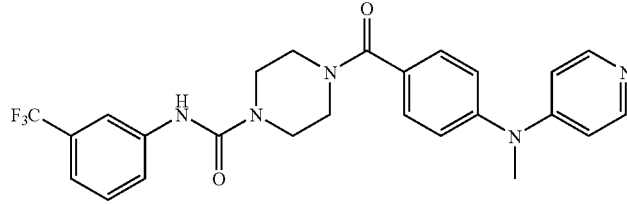 | 484 |
| 106A | 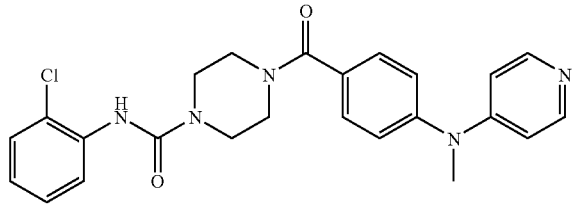 | 450 |
| 107A | 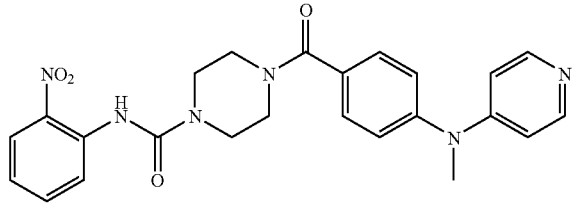 | 461 |

-continued

| Compound | Structure | MS (M + H) |
|---|---|---|
| 108A | 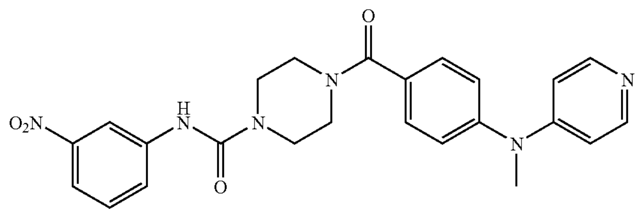 | 461 |
| 109A | 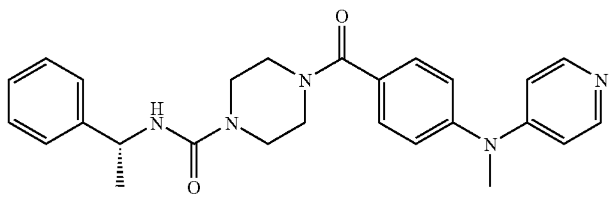 | 444 |
| 110A | 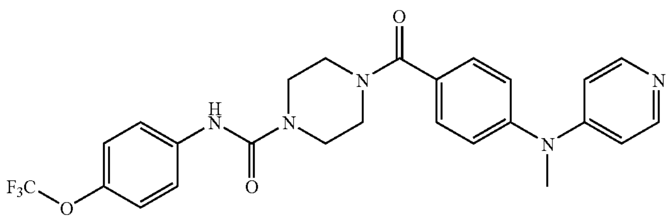 | 500 |
| 111A | 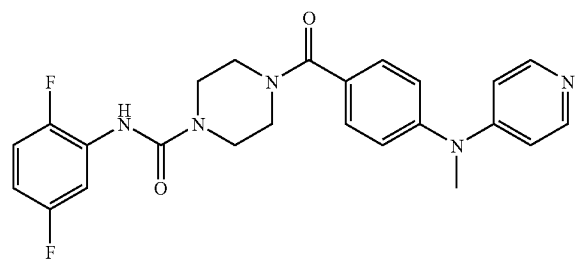 | 452 |
| 112A | 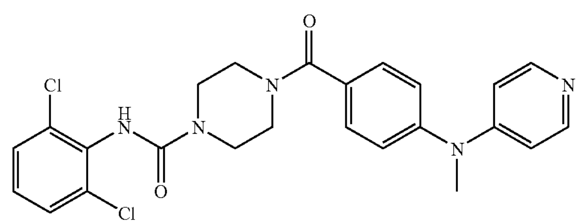 | 484 |
| 113A | 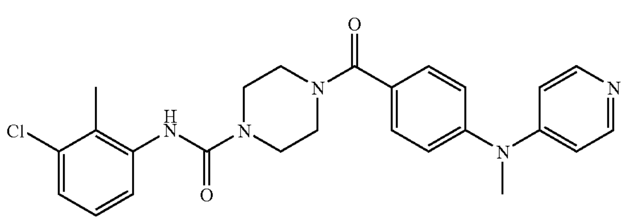 | 464 |
| 114A | 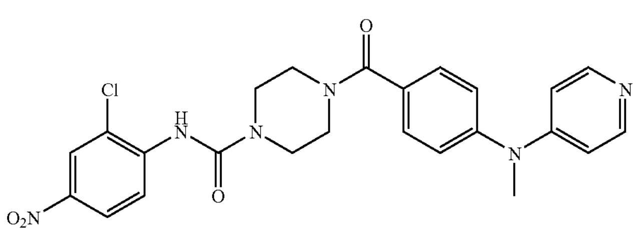 | 495 |

-continued

| Compound | Structure | MS (M + H) |
|---|---|---|
| 115A | 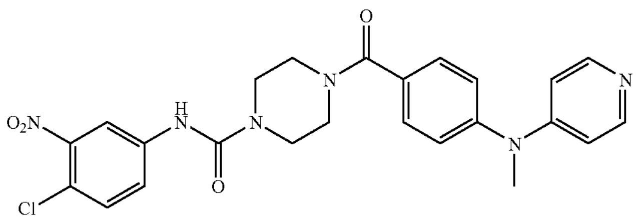 | 495 |
| 116A | 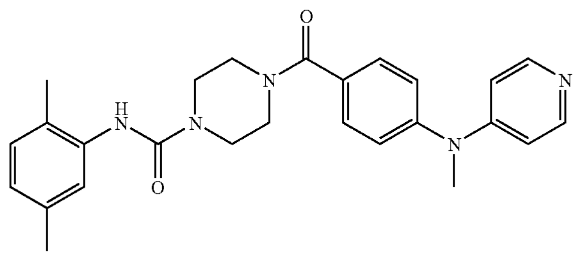 | 444 |
| 117A | 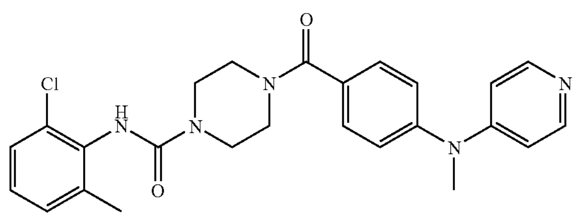 | 464 |
| 118A | 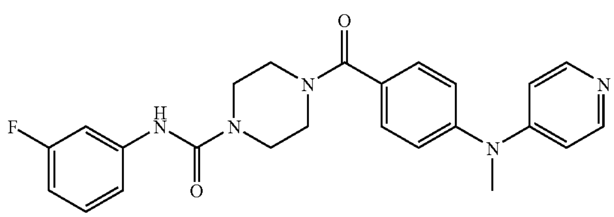 | 434 |
| 119A | 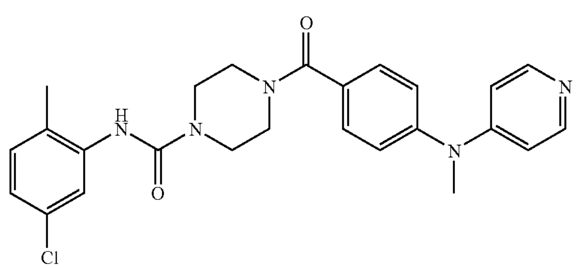 | 464 |
| 120A | 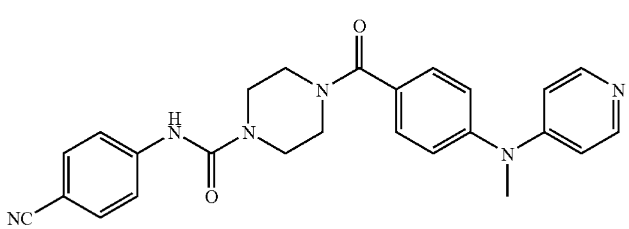 | 441 |

-continued

| Compound | Structure | MS (M + H) |
|---|---|---|
| 121A | 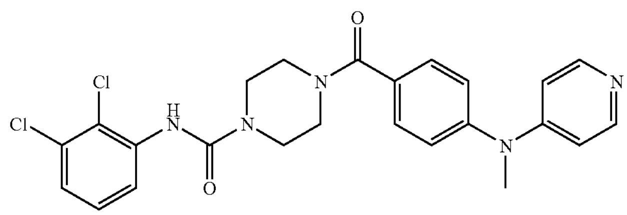 | 484 |
| 122A | 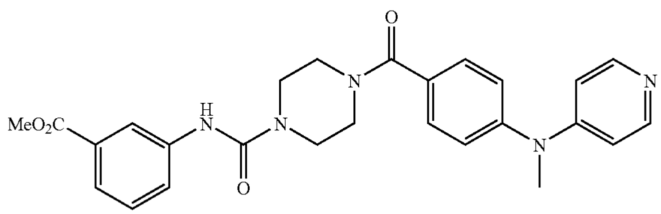 | 474 |
| 123A | 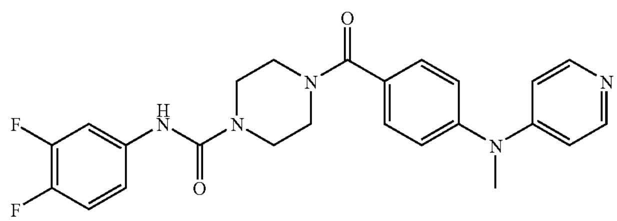 | 452 |
| 124A | 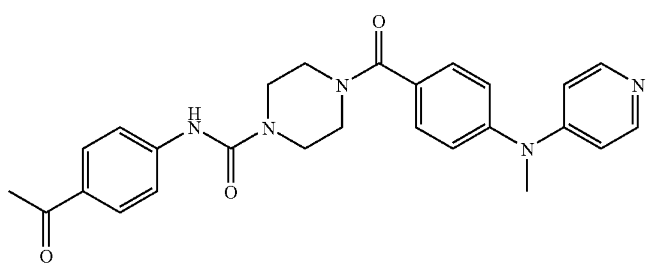 | 458 |
| 125A | 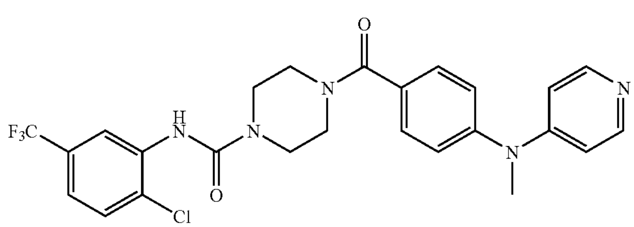 | 518 |
| 126A | 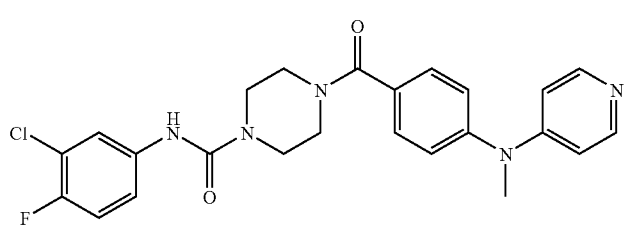 | 468 |

-continued

| Compound | Structure | MS (M + H) |
|---|---|---|
| 127A | 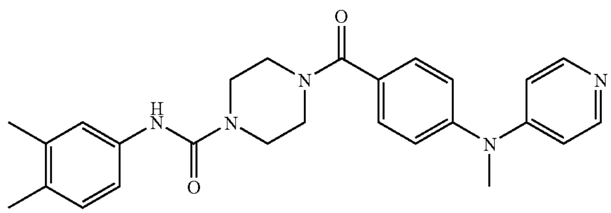 | 444 |
| 128A | 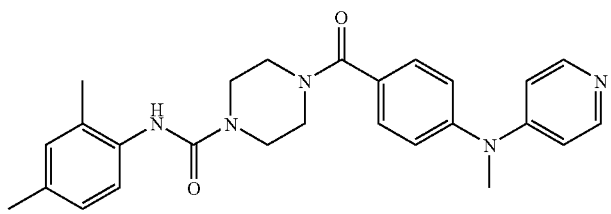 | 444 |
| 129A | 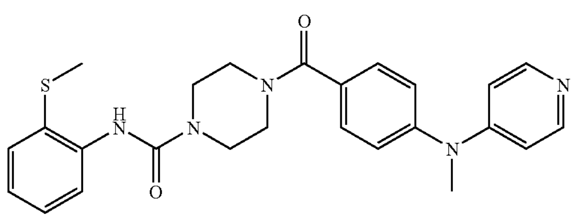 | 462 |
| 130A | 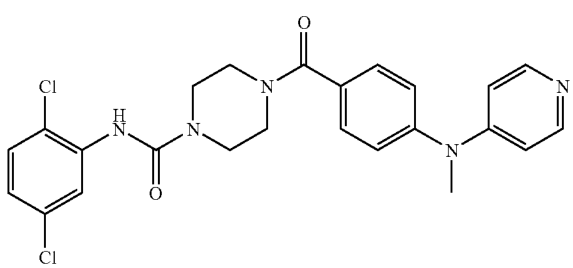 | 484 |
| 131A | 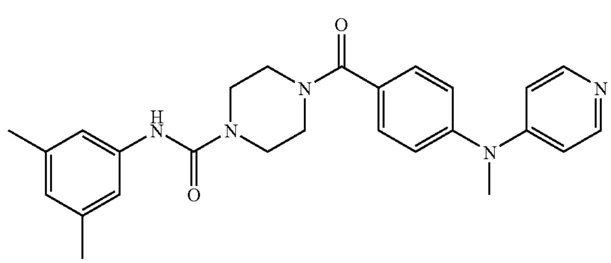 | 444 |
| 132A | 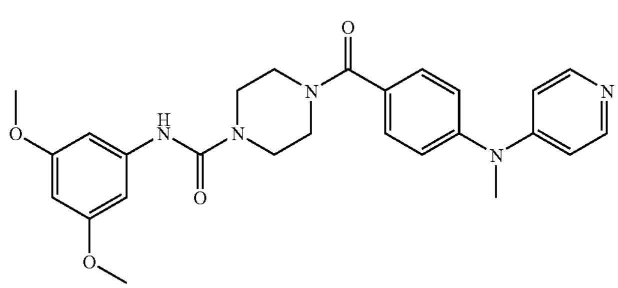 | 476 |

-continued

| Compound | Structure | MS (M + H) |
|---|---|---|
| 133A | 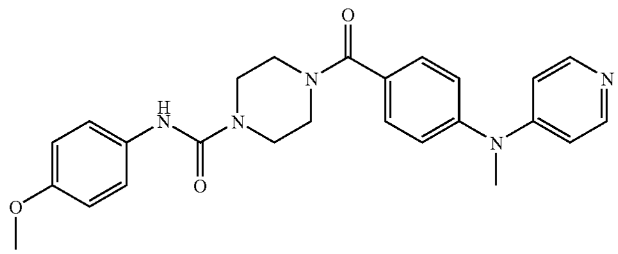 | 446 |
| 134A | 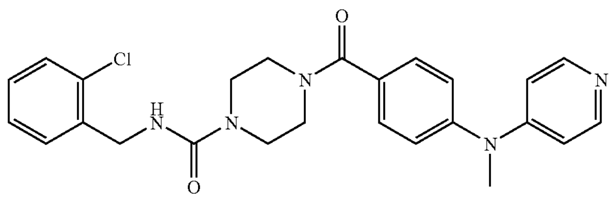 | 464 |
| 135A | 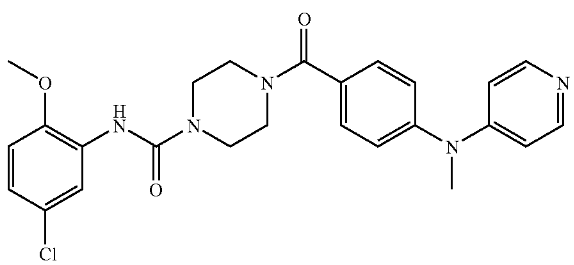 | 480 |
| 136A | 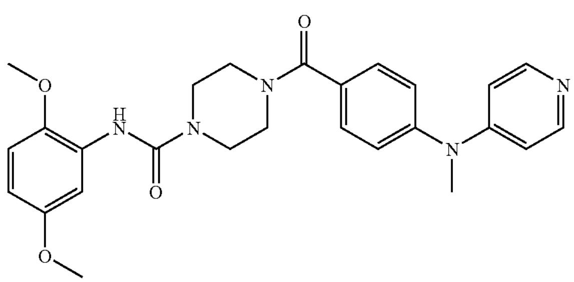 | 476 |
| 137A | 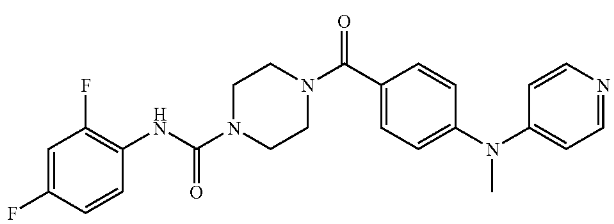 | 452 |
| 138A | 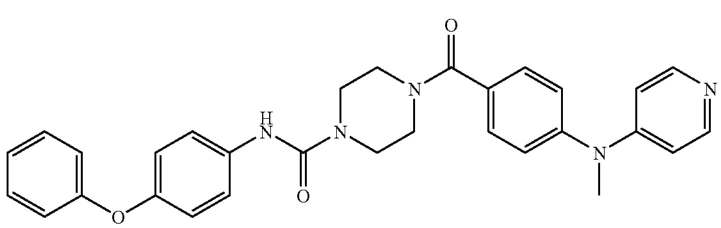 | 508 |

-continued

| Compound | Structure | MS (M + H) |
|---|---|---|
| 139A | 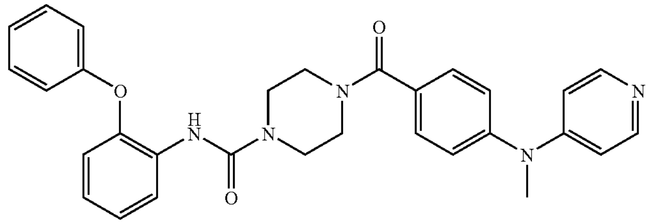 | 508 |
| 140A | 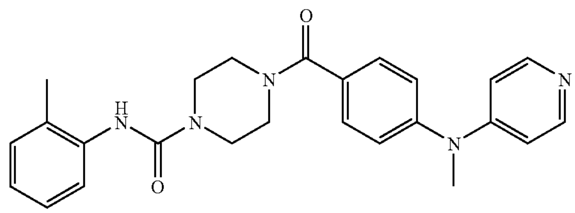 | 430 |
| 141A | 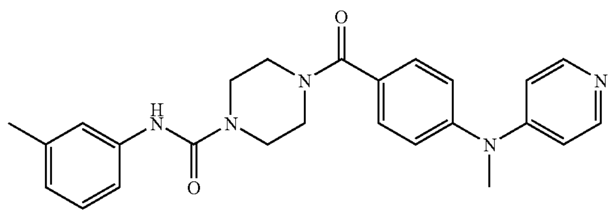 | 430 |
| 142A | 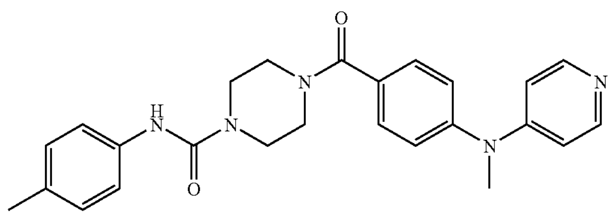 | 430 |
| 143A | 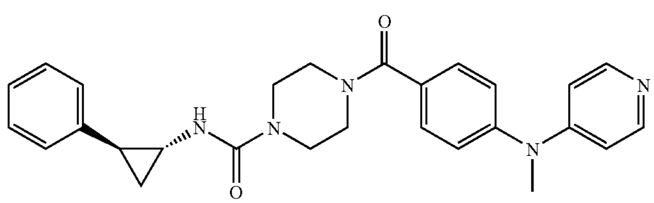 | 456 |
| 144A | 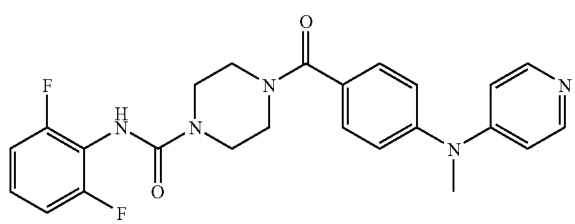 | 452 |
| 145A | 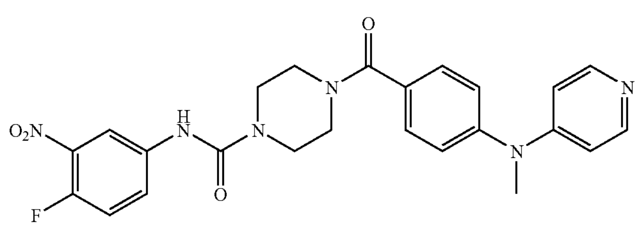 | 479 |

-continued

| Compound | Structure | MS (M + H) |
| --- | --- | --- |
| 146A | 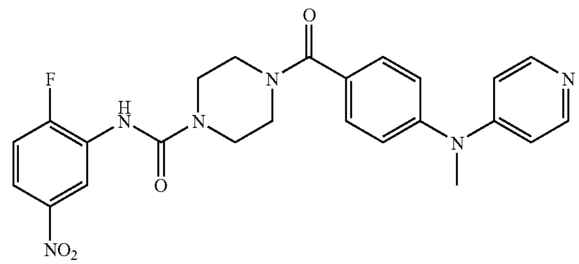 | 479 |
| 147A | 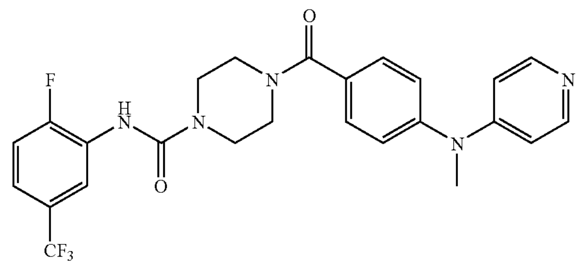 | 502 |
| 148A | 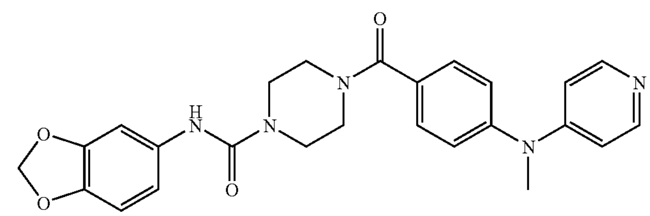 | 460 |
| 149A | 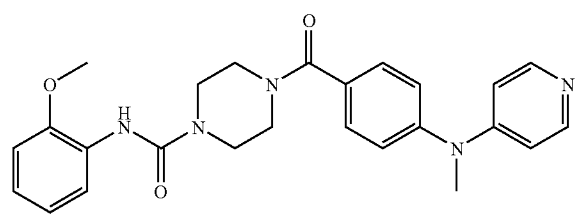 | 446 |
| 150A | 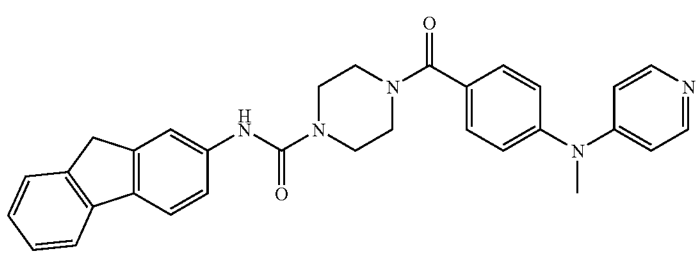 | 504 |
| 151A | 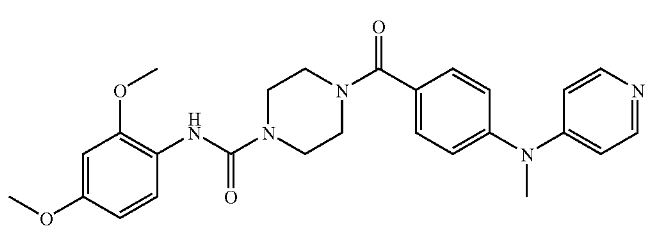 | 476 |

| Compound | Structure | MS (M + H) |
|---|---|---|
| 152A | 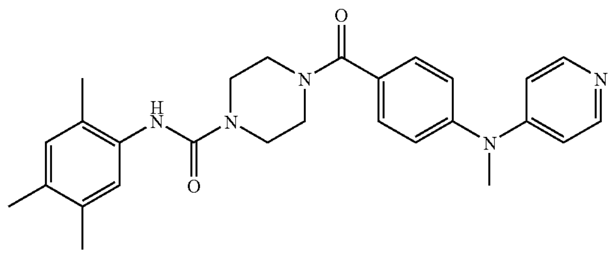 | 458 |
| 153A | 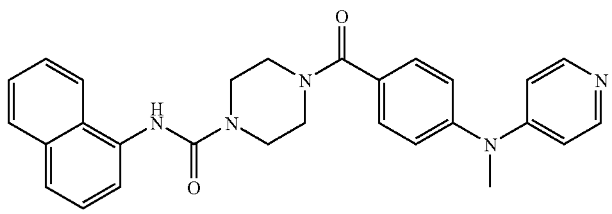 | 466 |
| 154A | 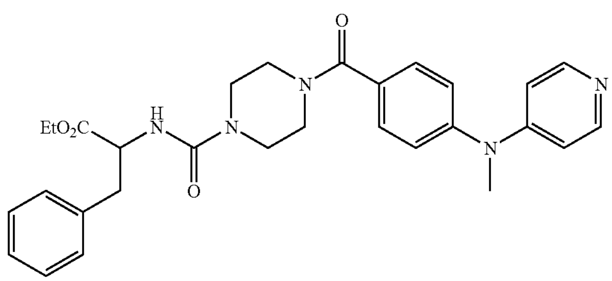 | 516 |
| 155A | 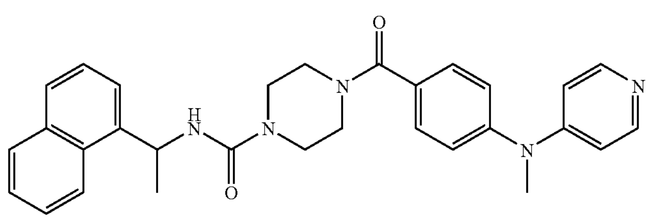 | 494 |
| 156A | 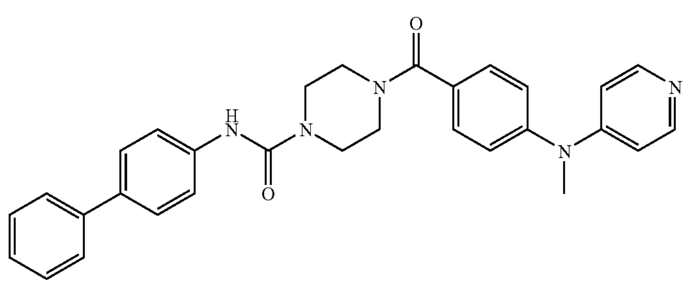 | 492 |
| 157A | 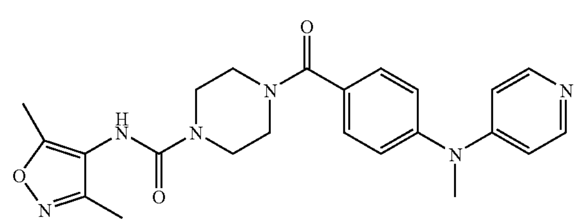 | 435 |

-continued

| Compound | Structure | MS (M + H) |
|---|---|---|
| 158A | 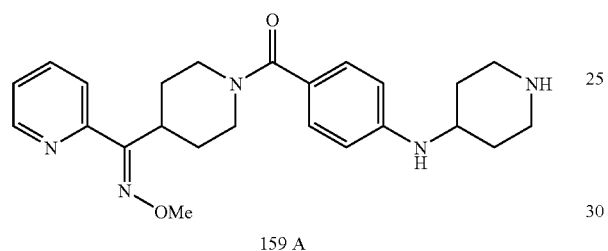 | 502 |

Example 30

Preparation of Compound 159A

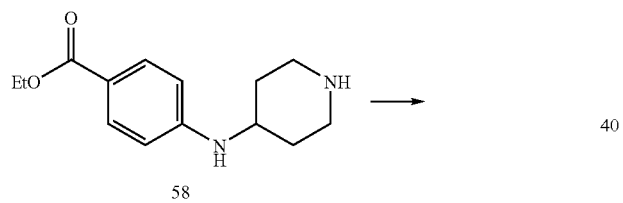

159 A

Step 1:

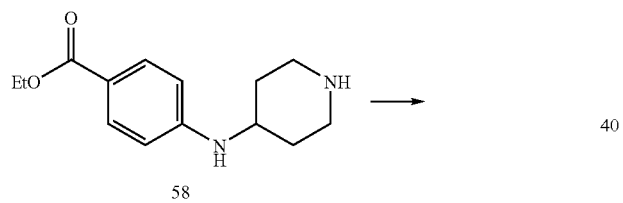

58

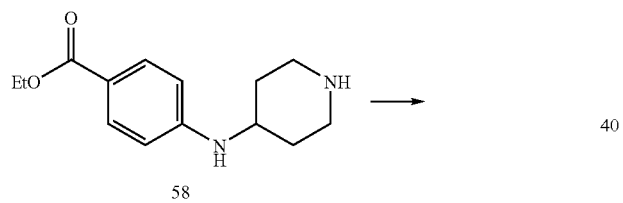

59

Di-tert-butyl dicarbonate (2.40 g, 11.0 mmol) was added to a stirred solution of 58 (2.09 g, 8.42 mmol) in tert-butanol (80 ml) at room temperature. The resulting mixture was heated at 60° C. for 16 h, then cooled to room temperature and the solvent was removed under vacuum. The residue was purified by column chromatography (EtOAc:Hexanes 1:5) to give 59 (2.899 g, 99%) as a white foam.

Step 2:

59 ⟶

-continued

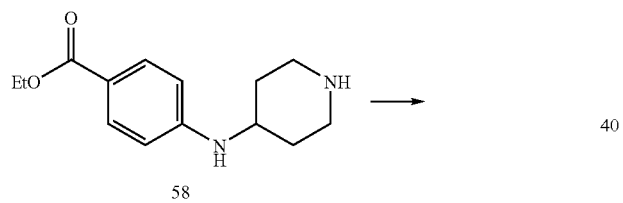

60

1N LiOH (5.44 ml, 5.44 mmol, 1.30 eq) was added to a stirred solution of 59 (1.58 g, 4.54 mmol) in MeOH (20 ml) at room temperature. The resulting mixture was stirred at 60° C. for 2.5 h, then the solvent was removed under vacuo and the resulting lithium carboxylate was dried under high vacuum for 24 h to give 60 (1.675 g, 100%) as a white solid which contained LiOH (0.3 eq) and was used without further purification.

Step 3:

Compound 60 was converted into the title compound using the procedure of Example 1, Step 2, followed by the procedure of Example 4, Step 2. MH⁺ 495

Example 131

Preparation of Compound 160A

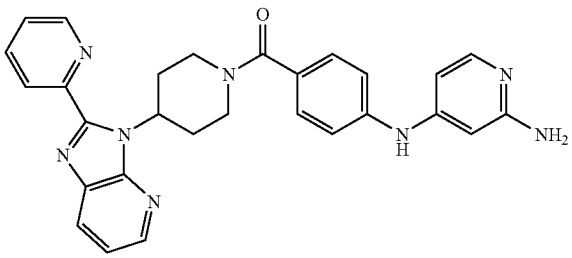

160A

Step 1

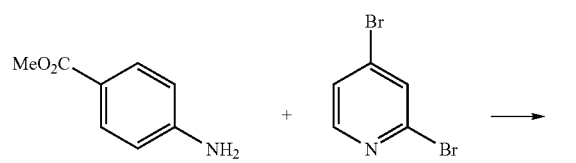

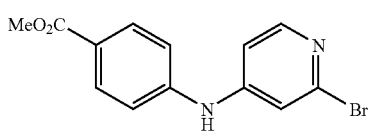

61

To a stirred solution of 2,4-dibromopyridinium hydrochloride (535 mg, 1.96 mmol) in 2,2,2-trifluoroethanol (5 mL) in a sealed tube, was added 4-aminobenzoic acid methyl ester (296 mg, 1.96 mmol, 1.0 eq). The resulting reaction was heated to 110° C. and allowed to stir at this temperature for 15 h. The reaction mixture was then was cooled to room temperature, concentrated in vacuo and the resulting residue was diluted with 10% aqueous $NH_3$ (150 mL) and DCM (150 mL) and the mixture was transferred to a separatory funnel. The aqueous layer was extracted with DCM (150 mL) and the combined organic phases were dried over $MgSO_4$ and concentrated in vacuo to provide a give a white solid residue which was purified using column chromatography (AcOEt: Hexane 0% to 50%) to provide compound 61 (308 mg, 51%) as a white solid. Note: The 2-isomer (72 mg, 12%) was also obtained as a less polar compound.

Step 2

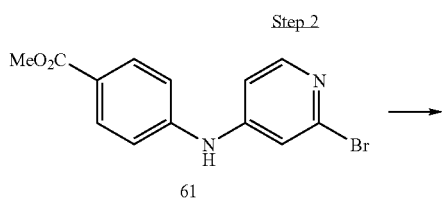

61

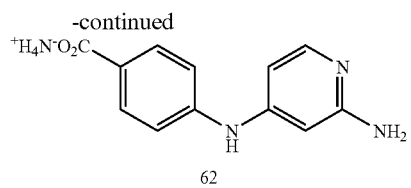

62

A bomb was charged with a solution of compound 61 (2.2 g, 7.16 mmol) in aqueous concentrated ammonia (75 mL) and the resulting mixture was heated to 210° C. and allowed to stir at this temperature for 20 h. The system was cooled to room temperature and the reaction mixture was concentrated in vacuo to provide the title compound (2.3 g) in vacuo as a white solid which was used in the next step without further purification.

Step 3

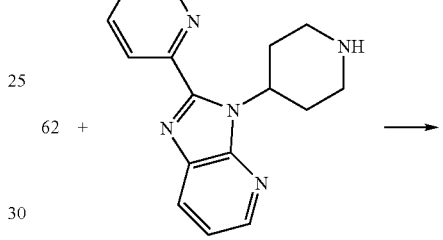

63

62 +

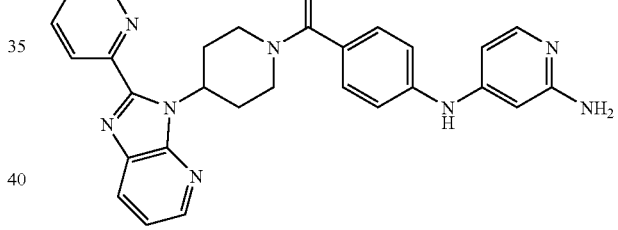

Compound 63 (prepared as describe in U.S. Patent Publication No. 2004/0097483) was reacted with compound 62 using the method set forth in Example 1, step 2 to obtain the title compound. $MH^+$ 491

Using procedures described above the following compounds were prepared:

| Example # | Structure | $(M + H)^+$ |
|---|---|---|
| 161A | 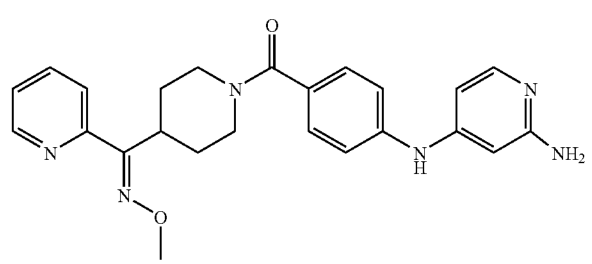 | 431 |

Example 32

H₃-Receptor Binding Assay

The source of the H₃ receptors in this experiment was guinea pig brain. Alternatively, the source of H₃ receptors was recombinant human receptor, expressed in HEK-293 (human embryonic kidney) cells.

The animals weighed 400-600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein, 5 μg in the case of recombinant human receptor) to the reaction tubes. The reaction was started by the addition of 3 nM [³H]R-α-methyl histamine (8.8 Ci/mmol) or 3 nM [³H]N^α-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Compounds of formula (I) have a $K_i$ within the range of about 3 to about 600 nM at the recombinant human H₃ receptor and from about 2 nM to about 2000 nM at the guinea pig brain receptor. The compound of Example 59 has a $K_i$ of 3 nM the recombinant human receptor assay, and the compound of Example 54 has a $K_i$ of 2 nM in the guinea pig receptor assay.

Example 33

Effects of the Compounds of the Invention on Diet-Induced Obesity in Mice

Lean mice (male, approx. 5 weeks of age, purchased from The Jackson Laboratory, Bar Harbor, Me.) were maintained in individual cages at 22° C. on a 12:12 hr light/dark cycle. The "treated" mice (N=12) were administered a Thiazole Derivative (10 mg/kg) by gavage once daily for four consecutive days. Control mice (N=12) were administered vehicle only, once daily for four days. Both control and treated mice were fed a high-fat diet from days 0 to 4 and body weight and food intake were monitored daily. The percent inhibition for weight gain and food intake was calculated by comparing the increase in weight gain and food intake in the treated mice to the increase in weight gain and food intake in the control mice.

Table 1 shows the effects of illustrative compounds of the invention on diet-induced obesity in mice. Compound numbers correspond to the compound numbering set forth in the specification.

TABLE 1

| Compound No. | Weight Gain Inhibition (%) | Food intake Inhibition (%) |
| --- | --- | --- |
| 57A | 17.0 | 2.5 |
| 59A | 21.0 | 1.1 |
| 160A | 33.0 | 18.3 |

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

A number of references have been cited, the entire disclosures of which have been incorporated herein in their entirety.

What is claimed is:

1. A compound which is selected from the group consisting of:

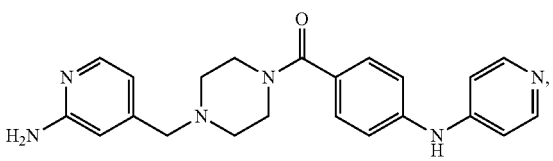

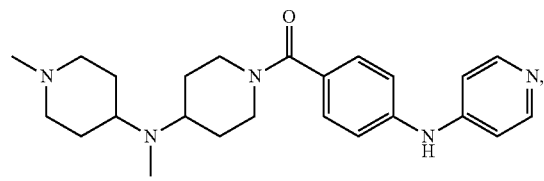

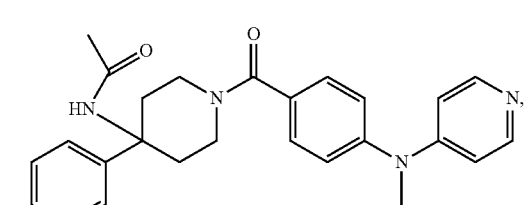

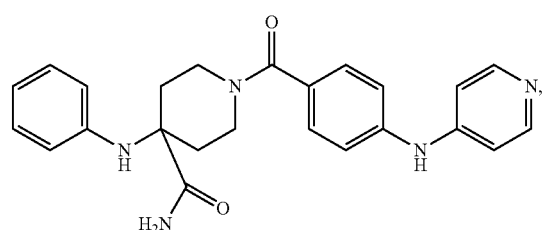

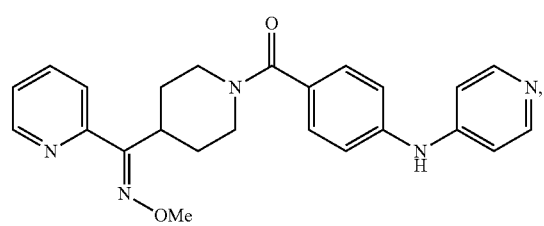

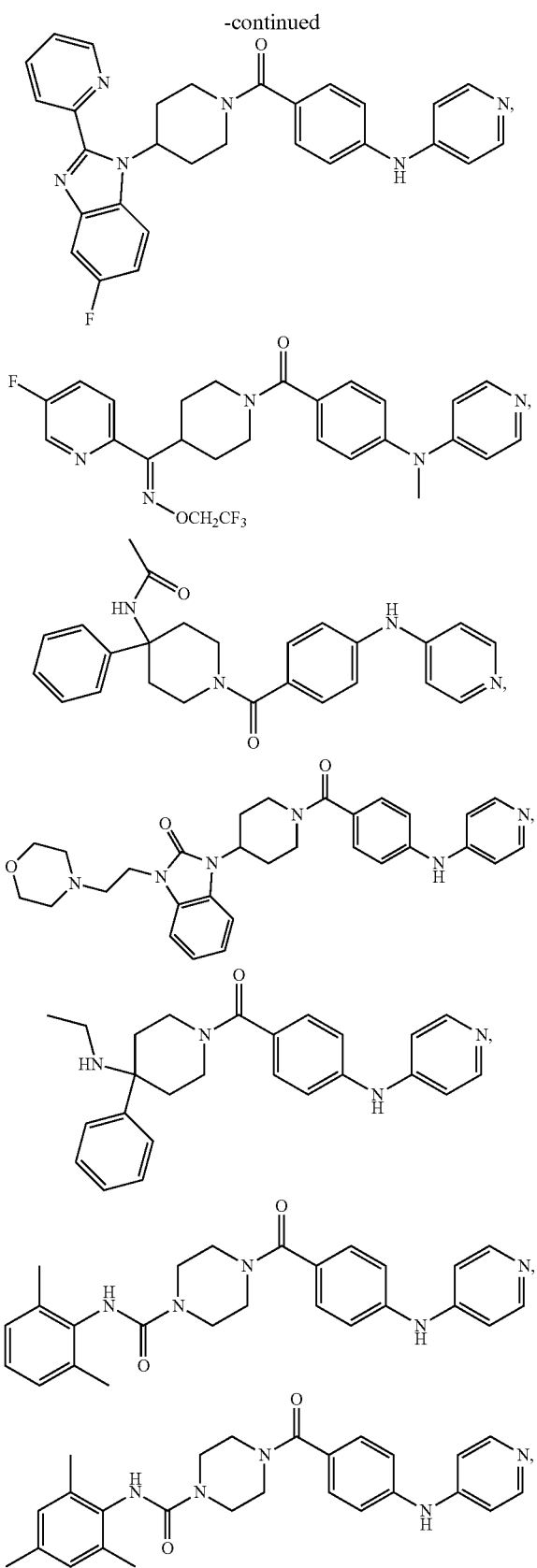
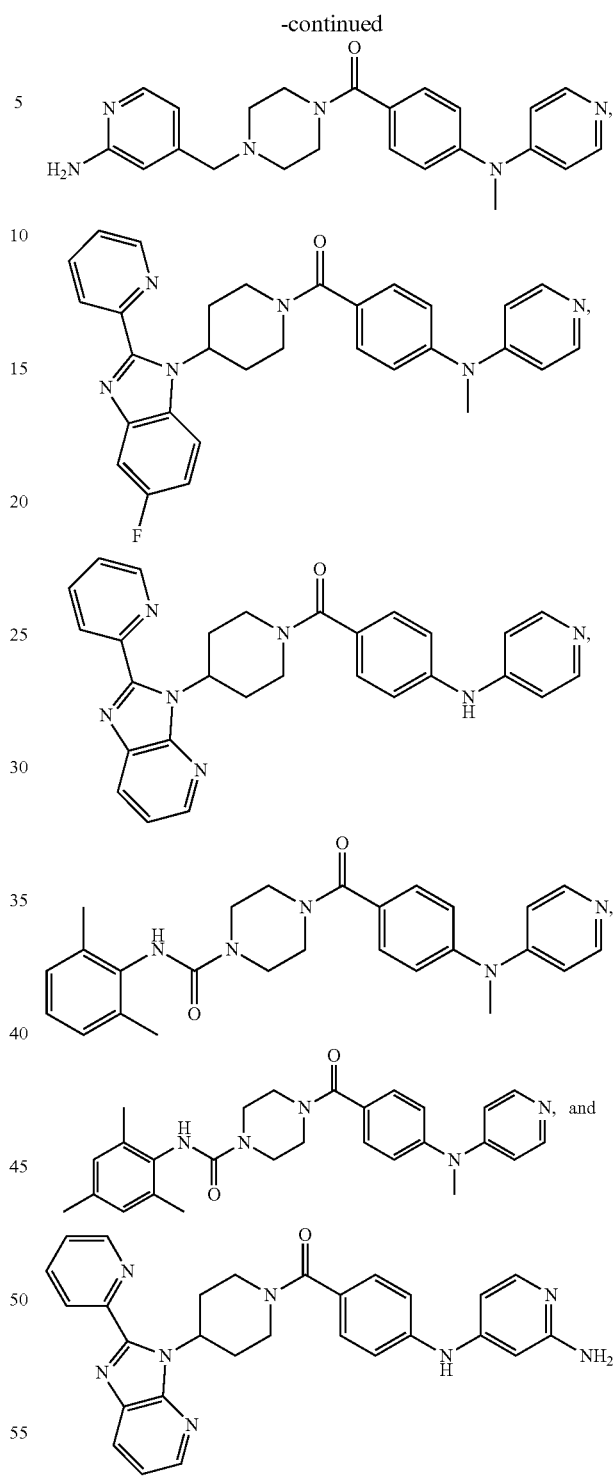
or a pharmaceutically acceptable salt thereof.
2. A pharmaceutical composition comprising the compound of claim 1, or a pharmaceutically acceptable salt thereof, and a pharmaceutically acceptable carrier.
* * * * *